US011149313B2

(12) United States Patent
Umansky et al.

(10) Patent No.: US 11,149,313 B2
(45) Date of Patent: Oct. 19, 2021

(54) METHODS OF USING MIRNAS FROM BODILY FLUIDS FOR DETECTION AND DIFFERENTIATION OF NEURODEGENERATIVE DISEASES

(71) Applicant: DIAMIR, LLC, Princeton, NJ (US)

(72) Inventors: Samuil R. Umansky, Princeton, NJ (US); Kira S. Sheinerman, New York, NY (US); Vladimir G. Tsivinsky, Sharon, MA (US)

(73) Assignee: DIAMIR, LLC, Princeton, NY (US)

( * ) Notice: Subject to any disclaimer, the term of this patent is extended or adjusted under 35 U.S.C. 154(b) by 19 days.

(21) Appl. No.: 16/086,881

(22) PCT Filed: Mar. 21, 2017

(86) PCT No.: PCT/US2017/023470
§ 371 (c)(1),
(2) Date: Sep. 20, 2018

(87) PCT Pub. No.: WO2017/165458
PCT Pub. Date: Sep. 28, 2017

(65) Prior Publication Data
US 2019/0093167 A1 Mar. 28, 2019

Related U.S. Application Data

(60) Provisional application No. 62/365,663, filed on Jul. 22, 2016, provisional application No. 62/310,979, filed on Mar. 21, 2016.

(51) Int. Cl.
C12Q 1/6883 (2018.01)

(52) U.S. Cl.
CPC ..... *C12Q 1/6883* (2013.01); *C12Q 2600/106* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 4,785,507 | A | 11/1988 | Miyazaki et al. |
|---|---|---|---|
| 4,829,304 | A | 5/1989 | Baird |
| 4,939,663 | A | 7/1990 | Baird |
| 7,653,509 | B2 | 1/2010 | Bagwell |
| 7,897,356 | B2 | 3/2011 | Klass et al. |
| 7,993,831 | B2 | 8/2011 | Latham et al. |
| 8,486,626 | B2 | 7/2013 | Umansky et al. |
| 8,632,967 | B2 | 1/2014 | Kuroda et al. |
| 8,648,017 | B2 | 2/2014 | Umansky et al. |
| 9,447,471 | B2 | 9/2016 | Qu et al. |
| 9,540,692 | B2 | 1/2017 | Xu |
| 9,605,315 | B2 | 3/2017 | Patel et al. |
| 9,611,511 | B2 | 4/2017 | Keller et al. |
| 9,708,667 | B2 | 7/2017 | Yanai et al. |
| 9,726,676 | B2 | 8/2017 | Grabe et al. |
| 9,790,554 | B2 | 10/2017 | Keller et al. |
| 9,803,242 | B2 | 10/2017 | Umansky et al. |
| 9,809,857 | B2 | 11/2017 | Wang |
| 9,933,440 | B2 | 4/2018 | Goetzl |
| 2007/0161004 | A1 | 7/2007 | Brown et al. |
| 2008/0020390 | A1 | 1/2008 | Mitchell et al. |
| 2008/0139801 | A1 | 6/2008 | Umansky et al. |
| 2008/0171667 | A1 | 7/2008 | Brown et al. |
| 2009/0004668 | A1 | 1/2009 | Chen et al. |
| 2009/0075258 | A1 | 3/2009 | Latham et al. |
| 2009/0081640 | A1 | 3/2009 | Umansky et al. |
| 2009/0176723 | A1 | 7/2009 | Brown et al. |
| 2010/0151480 | A1 | 6/2010 | Taylor et al. |
| 2010/0167937 | A1 | 7/2010 | Goldknopf et al. |
| 2010/0167948 | A1 | 7/2010 | Krichevsky et al. |
| 2010/0184046 | A1 | 7/2010 | Klass et al. |
| 2010/0196426 | A1 | 8/2010 | Skog et al. |
| 2010/0216139 | A1 | 8/2010 | Galas et al. |
| 2010/0227908 | A1 | 9/2010 | Cairns |
| 2010/0267804 | A1 | 10/2010 | Port et al. |
| 2010/0279292 | A1 | 11/2010 | Marsh et al. |
| 2010/0286044 | A1 | 11/2010 | Litman et al. |
| 2010/0323357 | A1 | 12/2010 | Nana-Sinkam et al. |
| 2011/0003704 | A1 | 1/2011 | Skog et al. |
| 2011/0053157 | A1 | 3/2011 | Skog et al. |
| 2011/0053158 | A1 | 3/2011 | Mambo et al. |
| 2011/0086348 | A1 | 4/2011 | Prasad et al. |
| 2011/0111976 | A1 | 5/2011 | Fare et al. |
| 2011/0117111 | A1 | 5/2011 | Kwon et al. |
| 2011/0117560 | A1 | 5/2011 | Spinale et al. |
| 2011/0143360 | A1 | 6/2011 | Kuroda et al. |
| 2011/0160285 | A1 | 6/2011 | Anderson et al. |

(Continued)

FOREIGN PATENT DOCUMENTS

| CN | 101942502 A | 1/2011 |
|---|---|---|
| CN | 101962685 A | 2/2011 |

(Continued)

OTHER PUBLICATIONS

Liu et al Clinical Immunology. 2004. 112: 225-230 (Year: 2004).*
Coleman, R. Drug Discovery Today. 2003. 8: 233-235 (Year: 2003).*
Heggard et al. International Journal of Cancer. May 4, 2011. 102. 130: 1378-1386 (Year: 2011).*
Communication (International Search Report and Written Opinion) issued by the International Searching Authority in International Patent Application No. PCT/US2017/023470 dated Jul. 31, 2017, 24 pages total.
Abdel-Salam, O.M.E. et al., "Drugs Used to Treat Parkinson's Disease, Present Status and Future Directions" CNS & Neurological Disorders—Drug Targets (2008) vol. 7, pp. 321-342.
Canadian Communication received for Canadian Patent Application No. 2,833,375, dated Dec. 9, 2019, 5 pages.

(Continued)

*Primary Examiner* — Carla J Myers
(74) *Attorney, Agent, or Firm* — Troutman Pepper Hamilton Sanders LLP

(57) ABSTRACT

The invention is directed to methods for diagnosis and differentiation of neurodegenerative diseases (NDs), by quantifying miRNAs in bodily fluids.

31 Claims, 19 Drawing Sheets

(56) References Cited

U.S. PATENT DOCUMENTS

| | | | |
|---|---|---|---|
| 2011/0160290 | A1 | 6/2011 | Tewari |
| 2012/0034608 | A1 | 2/2012 | Zhou et al. |
| 2012/0093936 | A1 | 4/2012 | Lindenberg et al. |
| 2012/0184599 | A1 | 7/2012 | Marcet et al. |
| 2012/0252693 | A1 | 10/2012 | Umansky et al. |
| 2012/0270746 | A1 | 10/2012 | Kuroda et al. |
| 2013/0012403 | A1* | 1/2013 | Hu ............... C12Q 1/6883 506/9 |
| 2013/0131194 | A1 | 5/2013 | Skog et al. |
| 2014/0120545 | A1 | 5/2014 | Umansky et al. |
| 2014/0170648 | A1 | 6/2014 | Kuroda et al. |
| 2014/0194319 | A1 | 7/2014 | Skog et al. |
| 2014/0194613 | A1 | 7/2014 | Skog et al. |
| 2014/0256562 | A1 | 9/2014 | Umansky et al. |
| 2014/0259192 | A1 | 9/2014 | Saarma et al. |
| 2014/0357507 | A1 | 12/2014 | Umansky et al. |
| 2015/0005365 | A1* | 1/2015 | Zakharenko ....... A61K 31/7105 514/44 A |
| 2016/0273043 | A1 | 9/2016 | Umansky et al. |
| 2017/0107575 | A1 | 4/2017 | Umansky et al. |
| 2017/0362656 | A1 | 12/2017 | Umansky et al. |

FOREIGN PATENT DOCUMENTS

| | | | |
|---|---|---|---|
| EP | 2699666 | B1 | 2/2014 |
| EP | 2699697 | A1 | 2/2014 |
| EP | 2496714 | B1 | 8/2016 |
| EP | 3071712 | A1 | 9/2016 |
| EP | 3118334 | A1 | 1/2017 |
| EP | 3133147 | A1 | 2/2017 |
| JP | 2010536372 | A | 12/2010 |
| JP | 2010538653 | A | 12/2010 |
| JP | 5624470 | B2 | 11/2014 |
| RU | 2367959 | C1 | 9/2009 |
| WO | 2005118806 | A2 | 12/2005 |
| WO | 2007073737 | A1 | 7/2007 |
| WO | 2008045505 | A2 | 4/2008 |
| WO | 2008153692 | A2 | 12/2008 |
| WO | 2009009457 | A1 | 1/2009 |
| WO | 2009012468 | A2 | 1/2009 |
| WO | 2009015357 | A1 | 1/2009 |
| WO | 2009025852 | A2 | 2/2009 |
| WO | 2009036236 | A1 | 3/2009 |
| WO | 2009070653 | A1 | 6/2009 |
| WO | 2009100029 | A1 | 8/2009 |
| WO | 2009114681 | A2 | 9/2009 |
| WO | 2009120877 | A2 | 10/2009 |
| WO | 2009132273 | A2 | 10/2009 |
| WO | 2009133915 | A1 | 11/2009 |
| WO | 2009143379 | A2 | 11/2009 |
| WO | 2009147519 | A1 | 12/2009 |
| WO | 2010054386 | A2 | 5/2010 |
| WO | 2010117829 | A2 | 10/2010 |
| WO | 2011015720 | A1 | 2/2011 |
| WO | 2011057003 | A2 | 5/2011 |
| WO | 2012145363 | A1 | 10/2012 |
| WO | 2012145409 | A1 | 10/2012 |
| WO | 2013036936 | A1 | 3/2013 |
| WO | 2015073972 | A1 | 5/2015 |
| WO | WO 2015/164431 | * | 10/2015 |
| WO | 2017120285 | A1 | 7/2017 |
| WO | 2017161256 | A1 | 9/2017 |
| WO | 2017165458 | A1 | 9/2017 |

OTHER PUBLICATIONS

Canadian Communication received for Canadian Patent Application No. 2,833,389, dated Nov. 22, 2019, 4 pages total.
Chinese Office Action dated Sep. 20, 2019, which issued during prosecution of Chinese Application No. 201480073413.0, 15 pages total.
Cloutier, F. et al., "MicroRNAs as Potential Circulating Biomarkers for Amyotrophic Lateral Sclerosis" Journal of Molecular Neuroscience (2014) vol. 56, No. 1, pp. 102-112.
European Communication (Extended European Search Report) received for European Application No. 17771018.3, dated Sep. 20, 2019, 9 pages total.
Gazewood, J.D. et al., "Parkinson Disease: An Update" American Family Physician (2013) vol. 87, No. 4, 7 pages total.
Japanese Office Action dated Aug. 13, 2019, which issued during prosecution of Japanese Application No. 2016-532043, 10 pages total.
Kansara, S. et al., "Early Diagnosis and Therapy of Parkinson's Disease: Can Disease Progression be Curbed?" J. Neural Transm. (2013) vol. 120, pp. 197-210.
Non-Final Office Action received for U.S. Appl. No. 15/037,559, dated Jun. 25, 2019, 34 pages.
Restriction Requirement received for U.S. Appl. No. 16/028,206, dated Dec. 13, 2019, 11 pages total.
Restriction Requirement received for U.S. Appl. No. 16/044,279, dated Oct. 8, 2019, 12 pages total.
Non-Final Office Action received for U.S. Appl. No. 16/044,279, dated Feb. 14, 2020, 61 pages total.
Osmanovic-Barilar, J. et al., "Evaluating the Role of Hormone Therapy in Postmenopausal Women with Alzheimer's Disease" Drugs Aging (2016) vol. 33, pp. 787-808.
Harman, D., "Alzheimer's Disease: Role of Aging in Pathogenesis" Annals New York Academy of Sciences (2002) vol. 959, pp. 384-395.
Final Office Action received for U.S. Appl. No. 15/037,559, dated Feb. 27, 2020, 17 pages.
Stem-loop Sequence hsa-mir-335 Accession No. MI0000816, Available online at: <http://www.mirbase.org/cgi-bin/mirna_entry.pl?acc=MI0000291>, 4 pages total.
Stem-loop Sequence hsa-mir-491 Accession No. MI0003126, Available online at: <http://www.mirbase.org/cgi-bin/mirna_entry.pl?acc=MI0003126>, 3 pages total.
Schymick, J. C. et al., "Expanding the Genetics of Amyotrophic Lateral Sclerosis and Frontotemporal Dementia" Alzheimer's Research & Therapy (2012) vol. 4, No. 30, 6 pages total.
Alzforum: Networking for a Cure, "Genetics Tie ALS into the Frontotemporal Dementia Spectrum" (2018) Available online at: <https://www.alzforum.org/news/research-news/genetics-tie-als-frontotemporal-dementia-spectrum>, 5 pages total.
Final Office Action received for U.S. Appl. No. 13/508,262, dated Jul. 30, 2013, 10 pages.
Final Office Action received for U.S. Appl. No. 14/112,684, dated Apr. 28, 2016, 19 pages.
Final Office Action received for U.S. Appl. No. 14/112,765, dated Oct. 9, 2015, 18 pages.
Final Office Action received for U.S. Appl. No. 15/037,559, dated Apr. 18, 2018, 26 pages.
Geekiyanage, H. et al., "Blood serum miRNA: Non-invasive biomarkers for Alzheimer's disease" Exp Neurol. (2011) vol. 235, pp. 491-496, ePub Dec. 1, 2011.
Gene Cards entry for MIR146A, retrieved from https://www.genecards.org/cgi-bin/carddisp.pl?gene=MIR146A&Keywords=mir146 on Apr. 14, 2018, 11 pages total.
Gillardon, F. et al. "MicroRNA and proteome expression profiling in early-symptomatic α-synuclein(A30P)-transgenic mice" Proteomics Clinical Application (2008) vol. 2, No. 5, pp. 697-705.
Goetz, C.G. "The History of Parkinson's Disease: Early Clinical Descriptions and Neurological Therapies" Cold Spring Harbor Perspect Med. (2011) vol. 1, a008862.
Griffiths-Jones, S. et al., "miRBase: microRNA sequences, targets and gene nomenclature" Nucleic Acids Research (2006) vol. 34, Database issue: D140-D144.
Hebert, S.S. et al. "Alterations of the microRNA network cause neurodegenerative disease" Trends in Neurosciences (2009) vol. 32, No. 4, pp. 199-206.
Hebert, S.S. et al., "Loss of microRNA cluster miR-29a/b-1 in sporadic Alzheimer's disease correlates with increased BACEI/beta-secretase expression" Proc Natl Acad Sci USA (2008) vol. 105, pp. 6415-6420.

(56) References Cited

OTHER PUBLICATIONS

Henriksen, K. et al., "The future of blood-based biomarkers for Alzheimer's disease" Alzheimer's & Dementia (2014) vol. 10, pp. 115-131.
Hua, D. et al., "A Catalogue of Glioblastoma and Brain MicroRNAs Identified by Deep Sequencing" OMICS A Journal of Integrative Biology (2012) vol. 16, No. 12, pp. 690-699.
Hua, Y-J. et al., "Identification and target prediction of miRNAs specifically expressed in rat neural tissue" BMC Genomics (2009) vol. 10, pp. 214-225.
Hunter, M.P. et al., "Detection of microRNA Expression in Human Peripheral Blood Microvesicles" PLoS ONE (2008) vol. 3, No. 11, e3694.
International Preliminary Report on Patentability for International Appl. No. PCT/US2010/055495, dated May 8, 2012, 15 pages total.
International Preliminary Report on Patentability issued in PCT/US2012/034098 dated Oct. 22, 2013, 15 pages total.
International Preliminary Report on Patentability received for PCT Patent Application No. PCT/US2012/034025, dated Oct. 31, 2013, 9 pages.
International Preliminary Report on Patentability received for PCT Patent Application No. PCT/US2014/065959, dated May 24, 2016, 15 pages.
International Preliminary Report on Patentability received for PCT Patent Application No. PCT/US2017/012258, dated Jul. 10, 2018, 12 pages.
International Search Report and Written Opinion for International Appl. No. PCT/US2010/055495, dated Jun. 6, 2011, 20 pages total.
International Search Report and Written Opinion of the International Searching Authority for International Application No. PCT/US2012/034025, dated Sep. 28, 2012, 14 pages total.
International Search Report and Written Opinion of the International Searching Authority for International Application No. PCT/US2012/034098, dated Jul. 17, 2012, 16 pages total.
International Search Report and Written Opinion of the International Searching Authority dated Apr. 28, 2015 issued during prosecution of International Application No. PCT/US2014/065959, 17 pages total.
International Search Report and Written Opinion of the International Searching Authority dated May 8, 2017 issued during prosecution of International Application No. PCT/US2017/012258, 14 pages total.
International Search Report for International Application No. PCT/US2017/23470, dated Jul. 31, 2017, 24 pages total.
Issler, O. et al., "Determining the Role of MicroRNAs in Psychiatric Disorders" Nature Reviews Neuroscience (2015) vol. 16, pp. 201-212.
Japanese Office Action issued in Japanese Patent Application No. 2014-506501 dated Mar. 16, 2016 (and English-language translation thereof), 15 pages.
Japanese Office Action issued in Japanese Patent Application No. 2014-506516 dated Apr. 4, 2016 (and English-language translation thereof), 20 pages.
Japanese Office Action issued in Japanese Patent Application No. 2014-506516 dated Mar. 1, 2017, 10 pages total.
Ji, X. et al., "Plasma miR-208 as a Biomarker of Myocardial Injury" Clinical Chemistry (2009) vol. 55, No. 11, pp. 1944-1949.
Kemppainen, et al., "MicroRNAs as biomarkers in blood and other biofluids, poster 2010?" [Retrieved from the Internet Sep. 8, 2012: <http://www.asuragen.comipdfs/postersibiomarkers.pdf>].
Koirala S. et al., "Pruning an Axon Piece by Piece" Neuron (2004) vol. 44, pp. 578-580.
Kosaka, N. et al., "Circulating microRNA in body fluid: a new potential biomarker for cancer diagnosis and prognosis" Cancer Sci. (2010) vol. 101, pp. 2087-2092.
Kosaka, N. et al., "Secretory Mechanisms and Intercellular Transfer of MicroRNAs in Living Cells" J Biol Chem. (2010) vol. 285, No. 23, pp. 17442-17452.
Kroh, E.M. et al., "Analysis of Circulating MircoRNA Biomarkers in Plasma and Serum Using Quantitative Reverse Transcription-PCR (qRT-PCR)" Methods (2010) vol. 50, pp. 298-301.
Kye, M.J. et al., "Somatodendritic microRNAs identified by laser capture and multiplex RT-PCR" RNA (2007) vol. 13, pp. 1224-1234.
Landgraf, P., "A Mammalian microRNA Expression Atlas Based on Small RNA Library Sequencing" Cell (2007) vol. 129, No. 7, pp. 1401-1414.
Laterza, O.F. et al., "Plasma MicroRNAs as Diagnostically Sensitive and Specific Biomarkers of Tissue Injury" Clinical Chemistry (2009) vol. 55, No. 11, pp. 1-7.
Lee, E.J. et al., "Systematic evaluation of microRNA processing patterns in tissues, cell lines, and tumors" RNA (2008) vol. 14, pp. 35-42.
Liang, Y. et al., "Characterization of microRNA expression profiles in normal human tissues" BMC Genomics (2007) vol. 8, pp. 166-185.
Liang, Y. "An expression meta-analysis of predicated microRNA targets identifies a diagnostic signature for lung cancer" BMC Med. Genomics (2008) vol. 1, No. 61, pp. 1-16.
Lin, A-L. et al., "Multimodal MRI Neuroimaging Biomarkers for Cognitive Normal Adults, Amnestic Mild Cognitive Impairment, and Alzheimer's Disease" Neurology Research International vol. 2012, Article ID 907409, 17 pages.
Lindner, K. et al. "Circulating microRNAs: emerging biomarkers for diagnosis and prognosis in patients with gastrointestinal cancers" Clinical Science (2015) vol. 128, pp. 1-15.
Liu, D-Z. et al., "Brain and blood microRNA expression profiling of ischemic stroke, intracerebral hemorrhage, and kainate seizures" J Cereb Blood Flow Metab., advance online publication (2009) doi:10.1038/jcbfm.2009, vol. 186, pp. 1-12.
Liu, R. et al., "A Five-microRNA Signature Identified from Genome-wide Serum microRNA Expression Profiling Serves as A Fingerprint for Gastric Cancer Diagnosis" European Journal of Cancer (2011) vol. 47, pp. 784-791.
Lodes, M. J. et al., "Detection of Cancer with Serum miRNAs on an Oligonucleotide Microarray" PLoS ONE (2009) vol. 4, No. 7, e6229.
Londin, E. et al., "Analysis of 13 cell types reveals evidence for the expression of numerous novel primate- and tissue-specific microRNAs" Proc. Natl. Acad. Sci. USA (2015) EII06-EII15.
Low, L.K. et al., "Axon pruning: an essential step underlying the developmental plasticity of neuronal connections" Phil Trans R Soc B. (2006) vol. 361, pp. 1531-1544.
Lugli, G. et al., "Expression of microRNAs and their precursors in synaptic fractions of adult mouse forebrain" Journal of Neurochemistry (2008) vol. 106, pp. 650-661.
Lugli, G. et al., "File S2. Entire list of measured human, rat and mouse microRNAs by microarray after filtering and normalization" Journal of Neurochemistry (2008) vol. 106.
Maes, O. C. et al. "Methodology for Discovery of Alzheimer's Disease Blood-Based Biomarkers" J Gerontol A Biol Sci Med Sci. (2009) vol. 64A, pp. 636-645.
Maes, O. C. et al., "MicroRNA: Implications for Alzheimer Disease and other Human CNS Disorders" Current Genomics (2009) vol. 10, pp. 154-168.
Mapstone, M. et al., "Plasma phospholipids identify antecedent memory impairment in older adults" Nature Medicine (2013) vol. 20, No. 4, pp. 415-418.
Mature Sequence hsa-miR-127-3p, Available online at: <http://www.mirbase.org/cgi-bin/mature.pl?mature_acc=MIMAT0000446>, 1 page.
McDonald, J.S. et al., "Analysis of circulating microRNA: pre analytical and analytical challenges" Clin Chem. (2011) vol. 57, pp. 833-840.
McKhann, G.M. et al., "The diagnosis of dementia due to Alzheimer's disease: Recommendations from National Institute on Aging—Alzheimer's Association workgroups on diagnostic guidelines for Alzheimer's disease" Alzheimer's Dement. (2011) vol. 7, pp. 263-269.
Mestdagh, P. et al., "High-throughput Stem-loop RT-qPCR miRNA Expression Profiling Using Minute Amounts of Input RNA" Nucleic Acids Research (2008) vol. 36, No. 21, 8 pages.

(56) References Cited

OTHER PUBLICATIONS

Meyer, S.U. et al., "Normalization Strategies for MircoRNA Profiling Experiments: A 'Normal' Way to a Hidden Layer of Complexity?" Biotechnol. Lett. (2010) vol. 32, pp. 1777-1788.
Miller, G., "Alzheimer's biomarker initiative hits its stride" Science (2009) vol. 326, pp. 386-389.
MirVana PARIS Kit Instructions Ambion, Life Technologies (2011) 36 pages total.
Mitchell, P.S. et al., "Circulating microRNAs as stable blood-based markers for cancer detection" Proc Natl Acad Sci USA (2008) vol. 105, pp. 10513-10518.
Miyachi, M. et al. "Circulating muscle-specific microRNA, miR-206, as a potential diagnostic marker for rhabdomyosarcoma" Biochem. Biophys. Res. Commun. (2010), vol. 400, pp. 89-93.
Murayama, S. et al., "The Pathology of Alzheimer's Disease" Clinician (2006) No. 553, pp. 15-19.
Natera-Naranjo, O. et al., "Identification and quantitative analyses of microRNAs located in the distal axons of sympathetic neurons" RNA (2010) vol. 16, pp. 1516-1529.
Non-Final Office Action received for U.S. Appl. No. 13/508,262, dated Mar. 7, 2013, 12 pages.
Non-Final Office Action received for U.S. Appl. No. 14/112,684, dated Jul. 9, 2015, 23 pages.
Non-Final Office Action received for U.S. Appl. No. 14/112,765, dated Apr. 28, 2015, 15 pages.
Non-Final Office Action received for U.S. Appl. No. 15/037,559, dated Jul. 27, 2017, 14 pages.
Non-Final Office Action received for U.S. Appl. No. 15/390,110, dated Jan. 31, 2018, 19 pages.
Non-Final Office Action received for U.S. Appl. No. 15/606,747, dated Jun. 1, 2018, 60 pages.
Olsen, L. et al., "MicroRNAs Show Mutually Exclusive Expression Patterns in the Brain of Adult Male Rats" PLoS ONE (2009) vol. 4, No. 10, e7225.
Peltier, H.J. et al., "Normalization of microRNA expression levels in quantitative RT-PCR assays: identification of suitable reference RNA targets in normal and cancerous human solid tissues" RNA (2008) vol. 14, pp. 844-852.
Petersen, R.C. et al., "Prevalence of Mild Cognitive Impairment is Higher in Men" The Mayo Clinic Study of Aging, Neurology (2010) vol. 75, pp. 889-897.
Pogue, A.I. et al., "Micro RNA-125b (miRNA-125b) Function in Astrogliosis and Glial Cell Proliferation" Neuroscience Letters (2010) vol. 476, pp. 18-22.
Ray, S. et al., "Classification and prediction of clinical Alzheimer's diagnosis based on plasma signaling proteins" Nat Med. (2007) vol. 13, pp. 1359-1362.
Satoh, J-i., "Molecular network of microRNA targets in Alzheimer's disease brains" Exp Neurol. (2012) vol. 235, pp. 436-446, ePub Sep. 16, 2011.
Satoh, J-i., "MicroRNAs and Their Therapeutic Potential for Human Diseases: Aberrant MicroRNA Expression in Alzheimer's Disease Brain" J Pharmacol Sci. (2010) vol. 114, pp. 269-275.
Schipper, H.M. et al., "MicroRNA expression in Alzheimer blood mononuclear cells" Gene Regul. Syst. Bio. (2007) vol. 1, pp. 263-274.
Schmand, B. et al., "Value of Neurophysiological Tests, Neuroimaging, and Biomarkers for Diagnosing Alzheimer's Disease in Younger and Older Age Cohorts" J Am Geriatr Soc. (2001) vol. 59, pp. 1705-1710.
Schratt, G. M. et al., "A brain-specific microRNA regulates dendritic spine development" Nature (2006) vol. 439, pp. 283-289.
Schratt, G., "microRNAs at the synapse" Nature Reviews Neuroscience (2009) vol. 10, pp. 842-849.
Sempere, L. F. et al., "Expression profiling of mammalian microRNAs uncovers a subset of brain-expressed microRNAs with possible roles in murine and human neuronal differentiation" Genome Biology (2004) vol. 5, No. R13, pp. R13.1-R13.11.
Sheinerman, K.S. et al.,"Plasma microRNA biomarkers for detection of mild cognitive impairment" AGING (2012) vol. 4, No. 9, pp. 590-605.
Sheinerman, K.S. et al., "Analysis of organ-enriched micro-RNAs in plasma as an approach to development of Universal Screening Test: feasibility study" Journal of Translational Medicine (2013) vol. 11, No. 304.
Sheinerman, K.S. et al., "Circulating cell-free microRNA as biomarkers for screening, diagnosis, and monitoring of neurode-generative diseases and other neurologic pathologies" Front.Cell.Neurosci. (2013) vol. 7, Art. 150, pp. 1-10.
Sheinerman, K.S. et al., "Early detection of neurodegenerative diseases" Cell Cycle (2013) vol. 12, No. 1.
Sheinerman, K.S. et al., "Plasma microRNA biomarkers for detection of mild cognitive impairment: biomarker validation study" AGING (2012) vol. 4, No. 9, pp. 17-18, 560-605.
Sheinerman, K.S. et al., Universal screening test based on analysis of circulating organ-enriched microRNAs: a novel approach to diagnostic screening, Expert Rev. Mol. Diagn. (2015) vol. 15, No. 3, pp. 329-338.
Shingara, J. et al. "An optimized isolation and labeling platform for accurate microRNA expression profiling" RNA (2005) vol. 11, pp. 1461-1470.
Skog, J. et al., "Glioblastoma microvesicles transport RNA and proteins that promote tumour growth and provide diagnostic biomarkers" Nat Cell Biol. (2008) vol. 10, No. 12, pp. 1470-1476.
Sperling, R.A. et al., "Toward Defining the Preclinical Stages of Alzheimer's Disease: Recommendations from the National Institute on Aging and the Alzheimer's Association Workgroup" Alzheimer's & Dementia (2011) pp. 1-13.
Sperling, R.A. et al., "The diagnosis of dementia due to Alzheimer's disease: Recommendations from National Institute on Aging—Alzheimer's Association workgroups on diagnostic guidelines for Alzheimer's disease" Alzheimer's Dement. (2011) vol. 7, pp. 280-292.
Supplementary Figures and Tables from Peltier et al. (RNA (2008) 14, pp. 844-852).
Veerla, S. et al. "MiRNA expression in urothelial carcinomas: important roles of miR-10a, miR-222, miR-125b, miR-7 and miR452 for lung stage and metastasis, and frequent homozygous losses of miR-31" International Journal of Cancer (2009), vol. 124, pp. 2236-2242.
Vlaminck, I. et al., "Circulating Cell-Free DNA Enables Noninvasive Diagnosis of Heart Transplant Rejection" Science Translational Medicine (2014) vol. 6, No. 241, pp. 1-19.
Wang, G-K. et al., "Circulating microRNA: a novel potential biomarker for early diagnosis of acute myocardial infarction in humans" European Heart Journal (2010) vol. 31, Issue 6, pp. 659-666.
Wang, K. et al., "Circulating microRNAs, potential biomarkers fordrug-induced liver injury" Proc Natl Acad Sci USA (2009) vol. 106, No. 11, pp. 4402-4407.
Wang, W-X. et al., "The Expression of MicroRNA miR-107 Decreases Early in Alzheimer's Disease and May Accelerate Disease Progression through Regulation of β-Site Amyloid Precursor Protein-Cleaving Enzyme 1" The Journal of Neuroscience (2008) vol. 28, pp. 1213-1223.
Wang, X., "A PCR-based Platform for microRNA Expression Profiling Studies" RNA (2009) vol. 15, pp. 716-723.
Chinese Office Action dated Mar. 26, 2019, which issued during prosecution of Chinese Application No. 201480073413.0, 8 pages total.
Chinese Office Action dated Mar. 25, 2019, which issued during prosecution of Chinese Application No. 201610344816.5, 13 pages total.
Final Office Action received for U.S. Appl. No. 15/606,747, dated Dec. 26, 2018, 40 pages.
Non-Final Office Action received for U.S. Appl. No. 15/390,110, dated Sep. 25, 2018, 30 pages.
Adachi, T. et al., Plasma MicroRNA 499 as a Biomarker of Acute Myocardial Infarction, Clinical Chemistry, vol. 56, No. 7, pp. 1183-1185, 2010.

(56) References Cited

OTHER PUBLICATIONS

Albert, M.S. et al., "The diagnosis of mild cognitive impairment due to Alzheimer's disease: Recommendations from National Institute on Aging—Alzheimer's Association workgroup" Alzheimer's & Dementia (2011) vol. 7, pp. 270-279.
Australia Patent Examination Report No. 1 issued in Australian Patent Application No. 2012245580 dated Aug. 30, 2016, 3 pages.
Australia Patent Examination Report No. 1 issued in Australian Patent Application No. 2012245628 dated Jun. 8, 2016, 6 pages.
Australia Patent Examination Report No. 2 issued in Australian Patent Application No. 2012245580 dated Jun. 2, 2017, 4 pages.
Backes, C. et al., "A dictionary on microRNAs and their putative target pathways" Nucleic Acids Research (2010) vol. 38, pp. 4476-4486.
Bak, M. et al., "MicroRNA expression in the adult mouse central nervous system" RNA. (2008) vol. 14, No. 3, pp. 432-444.
Bartel, D.P., "MicroRNAs: target recognition and regulatory functions" Cell (2009) vol. 136, pp. 215-233.
Bishop, D.L. et al., "Axon branch removal at developing synapses by axosome shedding" Neuron (2004) vol. 44, pp. 651-661.
Boeri, M. et al., "MicroRNA Signatures in Tissues and Plasma Predict Development and Prognosis of Computed Tomography Detected Lung Cancer" PNAS (2011) vol. 108, No. 9, pp. 3713-3718.
Braak, H. et al., "Neuropathological staging of Alzheimer's related changes" Acta Neuropathol (1991) vol. 82, pp. 239-259.
Brase, J. C. et al., "Circulating miRNAs are correlated with tumor progression in prostate cancer" International Journal of Cancer (2011) vol. 128, No. 3, pp. 608-616.
Brase, J. C. et al., "Serum microRNAs as non-invasive biomarkers for cancer" Molecular Cancer (2010) vol. 9, pp. 306-315.
Bredesen, D., "mCiRNA—Synaptic Crystal Ball?" AGING (2012) vol. 4, No. 11, pp. 732-733.
Canadian Communication received for Canadian Patent Application No. 2,780,222, dated Jan. 18, 2018, 5 pages.
Canadian Communication received for Canadian Patent Application No. 2,780,222, dated Nov. 18, 2016, 4 pages.
Canadian Communication received for Canadian Patent Application No. 2,833,375, dated Nov. 24, 2017, 7 pages.
Canadian Communication received for Canadian Patent Application No. 2,833,389, dated Nov. 21, 2017, 4 pages.
Charras, G. T. et al., "Life and times of a cellular bleb" Biophys J. (2008) vol. 94, No. 5, pp. 1836-1853.
Chen, X., "Characterization of microRNAs in serum: a novel class of biomarkers for diagnosis of cancer and other diseases" Cell Research (2008) vol. 18, pp. 997-1006.
Chim, S.S.C. et al., "Detection and Characterization of Placental MicroRNAs in Maternal Plasma" Clinical Chemistry (2008) vol. 54, No. 3, pp. 482-490.
Chinese Communication received for Chinese Patent Application No. 201280030048.6, dated Aug. 5, 2014.
Chinese Office Action dated Aug. 15, 2016, which issued during prosecution of Chinese Application No. 201280030033.X, 8 pages total.
Chinese Office Action dated Aug. 5, 2015, which issued during prosecution of Chinese Application No. 201280030048.6, 27 pages total.
Chinese Office Action dated Jul. 23, 2014, which issued during prosecution of Chinese Application No. 201280030033.X, 12 pages total.
Chinese Office Action dated Jun. 2, 2015, which issued during prosecution of Chinese Application No. 201280030033.X, 12 pages total.
Chinese Office Action dated Mar. 26, 2015, which issued during prosecution of Chinese Application No. 201280030048.6, 10 pages total.
Chinese Office Action dated Nov. 24, 2015, which issued during prosecution of Chinese Application No. 201280030033.X, 10 pages total.
Cogswell, J. P. et al., "Identification of miRNA Changes in Alzheimer's Disease Brain and CSF Yields Putative Biomarkers and Insights into Disease Pathways" Journal of Alzheimer's Disease (2008) vol. 14, pp. 27-41.
Delrieu, J. et al., "Managing Cognitive Dysfunction through the Continuum of Alzheimer's Disease" CNS Drugs (2011) vol. 25, No. 3, pp. 213-226.
Eaton, B.A. et al., "Synapse disassembly" Genes Dev. (2003) vol. 17, pp. 2075-2082.
Edbauer, D. et al., "Regulation of synaptic structure and function by FMRP-associated microRNAs miR-125b and miR-132" Neuron (2010) vol. 65, No. 3, pp. 373-384.
Emery, V., "Alzheimer disease: are we intervening too late?" J Neural Transm. (2011) vol. 118, No. 9, pp. 1361-1378.
European Communication (extended European search report) dated Feb. 27, 2018, which issued during prosecution of European Application No. 17207859.4, 9 pages total.
European Communication dated Nov. 15, 2016, which issued during prosecution of European Application No. 16 185 046.6, 12 pages total.
European Communication (Extended European Search Report) dated Jun. 9, 2017, which issued during prosecution of European Application No. 14862355.6, 9 pages total.
European Communication pursuant to Article 94(3) EPC dated Aug. 21, 2014, which issued during prosecution of European Application No. 10 779 376.2, 6 pages total.
European Communication pursuant to Article 94(3) EPC dated Dec. 8, 2016, which issued during prosecution of European Application No. 12 773 705.4, 4 pages total.
European Communication pursuant to Article 94(3) EPC dated Jan. 5, 2016, which issued during prosecution of European Application No. 12 773 705.4, 6 pages total.
European Communication pursuant to Article 94(3) EPC dated Jun. 25, 2015, which issued during prosecution of European Application No. 12 774 179.1, 4 pages total.
European Communication pursuant to Article 94(3) EPC dated May 24, 2013, which issued during prosecution of European Application No. 10 779 376.2, 11 pages total.
European Communication pursuant to Article 94(3) EPC dated Nov. 6, 2015, which issued during prosecution of European Application No. 10 779 376.2, 7 pages total.
European Communication pursuant to Article 94(3) EPC received for European Patent Application No. 14862355.6, dated Mar. 20, 2018, 5 pages.
European Communication pursuant to Rules 161(2) and 162 EPC dated Nov. 26, 2013, which issued during prosecution of European Application No. 12 774 179.1, 3 pages total.
European Communication pursuant to Rules 70(2) and 70a(2) EPC received for European Application No. 12 774 179.1, dated Nov. 18, 2014, 1 page.
European Communication received for European Patent Application No. 12773705.4, dated Sep. 16, 2014, 6 pages.
European Extended Search Report issued in European Application No. EP16 192 259.6; dated Jan. 24, 2017, 8 pages.
European Search Report dated Jan. 26, 2015, which issued during prosecution of European Application No. 12 773 705.4, 12 pages total.
European Search Report dated Oct. 30, 2014, which issued during prosecution of European Application No. 12 774 179.1, 7 pages total.
Fackler, O.T., et al., "Cell motility through plasma membrane blebbing" J Cell Biol. (2008) vol. 181, No. 6, pp. 879-884.
Weber, J.A. et al., "The microRNA spectrum in 12 body fluids" Clin. Chem. (2010) vol. 56, pp. 1733-1741.
Wu, Q. et al., "Next-Generation Sequencing of MicroRNAs for Breast Cancer Detection" Journal of Biomedicine and Biotechnology (2011) vol. 2011, Article ID 597145, 7 pages total.
Xu, S. et al. "MicroRNA (miRNA) transcriptome of mouse retina and identification of a sensory organ-specific miRNA cluster" Journal of Biological Chemistry (2007) vol. 282, p. 25053-25066.

(56) References Cited

OTHER PUBLICATIONS

Yoo, M.S. et al., "Oxidative Stress Regulated Genes in Nigral Dopaminergic Neuronal Cells: Correlation with the Known Pathology in Parkinson's Disease" Molecular Brain Research (2003) vol. 110, pp. 76-84.

Yoshiyama, Y. et al., "Synapse Loss and Microglial Activation Precede Tangles in P301S Tauopathy Mouse Model" Neuron (2007) vol. 53, pp. 337-351.

Zampetaki, A. et al., "Plasma microRNA Profiling Reveals Loss of Endothelial MiR-126 and Other microRNAs in Type 2 Diabetes" Circulation Research (2010) vol. 107, pp. 810-817.

Zhao, H. et al., "A Pilot Study of Circulating miRNAs as Potential Biomarkers of Early Stage Breast Cancer" PLoS ONE (2010) vol. 5, No. 10, 12 pages total.

Communication (International Preliminary Report on Patentability) issued by the International Searching Authority in International Patent Application No. PCT/US2017/023470 dated Jul. 31, 2017, 20 pages total.

Canadian Communication received for Canadian Patent Application No. 2,780,222 dated Jan. 28, 2019, 5 pages total.

Canadian Communication received for Canadian Patent Application No. 2,833,375, dated Oct. 12, 2018, 7 pages total.

Canadian Communication received for Canadian Patent Application No. 2,833,389, dated Oct. 18, 2018, 3 pages total.

European Communication (Article 94(3) EPC) received for European Application No. 14862355.6, dated Jan. 22, 2019, 8 pages total.

Japanese Communication (First Office Action) received for Japanese Patent Application No. 2017-174778, dated Nov. 16, 2018, 21 pages total.

Japanese Communication received for Japanese Patent Application No. 2016-532043, dated Oct. 2, 2018, 17 pages total.

Sheinerman, K.S. et al., "Circulating Brain-Enriched MicroRNAs as Novel Biomarkers for Detection and Differentiation of Neurodegenerative Diseases" Alzheimer's Research & Therapy (2017) vol. 9, No. 89, 13 pages total.

Ashrafi, A. et al., "Leukocyte Telomere Length is Unrelated to Cognitive Performance Among Non-Demented and Demented Persons: An Examination of Long Life Family Study Participants" Journal of International Neuropsychological Society (2020) 12 pages total.

Urdinguio, R.G. et al., "Disrupted microRNA Expression Caused by Mecp2 Loss in a Mouse Model of Rett Syndrome" Epigenetics (2010) vol. 5, Issue 7, pp. 656-663.

Non-Final Office Action received for U.S. Appl. No. 16/028,206, dated May 21, 2020, 22 pages total.

Canadian Communication received for Canadian Patent Application No. 2,780,222, dated May 21, 2020, 6 pages total.

Japanese Communication received for Japanese Patent Application No. 2016-532043, dated May 28, 2020, 15 pages total.

Chinese Office Action dated Jul. 3, 2020, which issued during prosecution of Chinese Application No. 201610344816.5, 10 pages total.

Canadian Communication received for Canadian Patent Application No. 2,833,375, dated Dec. 15, 2020, 5 pages.

Canadian Communication received for Canadian Patent Application No. 2,931,082, dated Jan. 29, 2021, 4 pages.

Final Office Action received for U.S. Appl. No. 16/086,881, dated Dec. 14, 2020, 29 pages total.

Japanese Communication received for Japanese Patent Application No. 2016-532043, dated Nov. 20, 2020, 13 pages total.

Canadian Communication received for Canadian Patent Application No. 2,833,389, dated Oct. 5, 2020, 3 pages total.

Chinese Communication received for Chinese Patent Application No. 201610344816.5, dated Feb. 5, 2021, 4 pages total.

European Communication (Communication pursuant, to Article 94(3) EPC) received for European Application No. 17771018.3, dated Oct. 9, 2020, 6 pages total.

Non-Final Office Action received for U.S. Appl. No. 15/037,559, dated Sep. 30, 2020, 23 pages.

\* cited by examiner

| # | miR-134 / miR-370 | miR-134 / miR-433 | miR-134 / miR-127-3p | miR-134 / miR-451 | miR-134 / miR-410 | miR-134 / miR-382 | miR-134 / miR-323-3p | miR-335-5p / miR-370 | miR-335-5p / miR-433 |
|---|---|---|---|---|---|---|---|---|---|
| SE | 0.66 | 0.69 | 0.79 | 0.48 | 0.9 | 0.62 | 0.72 | 0.72 | 0.62 |
| SP | 0.83 | 0.83 | 0.73 | 0.93 | 0.57 | 0.87 | 0.7 | 0.8 | 0.87 |
| AC | 0.75 | 0.76 | 0.76 | 0.71 | 0.73 | 0.75 | 0.71 | 0.76 | 0.75 |
| AU | 0.83 | 0.82 | 0.79 | 0.7 | 0.79 | 0.83 | 0.73 | 0.8 | 0.79 |
| PV | 1.60E-05 | 4.40E-05 | 3.10E-04 | 1.20E-02 | 2.40E-04 | 3.20E-05 | 3.60E-03 | 1.70E-04 | 2.20E-04 |

| # | miR-335-5p / miR-127-3p | miR-335-5p / miR-451 | miR-335-5p / miR-9 | miR-335-5p / miR-7 | miR-335-5p / miR-128a | miR-335-5p / miR-491-5p | miR-335-5p / miR-16 | miR-135a / miR-370 | miR-135a / miR-433 |
|---|---|---|---|---|---|---|---|---|---|
| SE | 0.83 | 0.52 | 0.76 | 0.76 | 0.76 | 0.9 | 0.52 | 0.41 | 0.86 |
| SP | 0.73 | 0.9 | 0.73 | 0.73 | 0.77 | 0.53 | 0.93 | 0.9 | 0.57 |
| AC | 0.78 | 0.71 | 0.75 | 0.75 | 0.76 | 0.71 | 0.73 | 0.66 | 0.71 |
| AU | 0.8 | 0.74 | 0.79 | 0.75 | 0.8 | 0.72 | 0.71 | 0.74 | 0.76 |
| PV | 2.00E-04 | 2.60E-03 | 3.00E-04 | 2.00E-03 | 2.20E-04 | 8.80E-03 | 8.50E-03 | 2.90E-03 | 8.90E-04 |

| # | miR-135a / miR-127-3p | miR-135a / miR-451 | miR-135a / miR-9 | miR-132 / miR-370 | miR-132 / miR-433 | miR-132 / miR-127-3p | miR-132 / miR-451 | miR-132 / miR-9 | miR-132 / miR-7 | miR-132 / miR-128a | miR-874 / miR-370 | miR-874 / miR-433 |
|---|---|---|---|---|---|---|---|---|---|---|---|---|
| SE | 0.62 | 0.62 | 0.69 | 0.66 | 0.76 | 0.69 | 0.62 | 0.76 | 0.66 | 0.55 | 0.79 | 0.59 |
| SP | 0.77 | 0.77 | 0.77 | 0.77 | 0.7 | 0.7 | 0.8 | 0.77 | 0.7 | 0.87 | 0.5 | 0.77 |
| AC | 0.69 | 0.69 | 0.73 | 0.71 | 0.73 | 0.69 | 0.71 | 0.76 | 0.68 | 0.71 | 0.64 | 0.68 |
| AU | 0.74 | 0.72 | 0.74 | 0.75 | 0.77 | 0.76 | 0.72 | 0.78 | 0.71 | 0.76 | 0.71 | 0.72 |
| PV | 2.70E-03 | 8.60E-03 | 2.60E-03 | 1.60E-03 | 9.20E-04 | 1.30E-03 | 9.80E-03 | 6.20E-04 | 1.10E-02 | 1.40E-03 | 8.60E-03 | 6.60E-03 |

FIGURE 1A

| # | miR-16 / miR-451 | miR-125b / miR-433 | miR-491-5p / miR-370 | miR-491-5p / miR-433 | miR-491-5p / miR-127-3p | miR-491-5p / miR-451 | miR-128a / miR-370 | miR-128a / miR-433 | miR-128a / miR-127-3p | miR-323-3p / miR-370 | miR-323-3p / miR-433 | miR-323-3p / miR-127-3p |
|---|---|---|---|---|---|---|---|---|---|---|---|---|
| SE | 0.62 | 0.72 | 0.72 | 0.72 | 0.69 | 0.59 | 0.48 | 0.79 | 0.52 | 0.93 | 0.79 | 0.72 |
| SP | 0.83 | 0.63 | 0.73 | 0.63 | 0.67 | 0.83 | 0.83 | 0.57 | 0.8 | 0.6 | 0.83 | 0.83 |
| AC | 0.73 | 0.68 | 0.73 | 0.68 | 0.68 | 0.71 | 0.66 | 0.68 | 0.66 | 0.76 | 0.81 | 0.78 |
| AU | 0.76 | 0.7 | 0.74 | 0.73 | 0.71 | 0.71 | 0.72 | 0.73 | 0.71 | 0.85 | 0.88 | 0.83 |
| PV | 2.20E-03 | 2.30E-02 | 3.70E-03 | 5.00E-03 | 1.20E-02 | 1.80E-02 | 8.60E-03 | 4.00E-03 | 8.80E-03 | 1.20E-05 | 1.90E-06 | 2.90E-05 |

| # | miR-382 / miR-370 | miR-382 / miR-433 | miR-382 / miR-127-3p | miR-410 / miR-370 | miR-410 / miR-433 | miR-410 / miR-127-3p | CHECKED |
|---|---|---|---|---|---|---|---|
| SE | 0.76 | 0.86 | 0.59 | 0.66 | 0.76 | 0.69 | 0.76 |
| SP | 0.67 | 0.73 | 0.83 | 0.77 | 0.7 | 0.73 | 0.9 |
| AC | 0.71 | 0.8 | 0.71 | 0.71 | 0.73 | 0.71 | 0.83 |
| AU | 0.74 | 0.8 | 0.73 | 0.77 | 0.78 | 0.76 | 0.93 |
| PV | 2.30E-03 | 2.10E-04 | 4.70E-03 | 9.20E-04 | 5.10E-04 | 1.20E-03 | 5.80E-09 |

FIGURE 1A (CONTINUED)

| # | miR-134 / miR-127-3p | miR-134 / miR-370 | miR-134 / miR-433 | miR-134 / miR-9 | miR-134 / miR-323-3p | miR-134 / miR-382 | miR-134 / miR-128a | miR-134 / miR-410 | miR-132 / miR-127-3p |
|---|---|---|---|---|---|---|---|---|---|
| SE | 0.88 | 0.94 | 0.94 | 0.69 | 0.88 | 0.75 | 0.88 | 0.69 | 0.88 |
| SP | 0.71 | 0.64 | 0.71 | 0.93 | 0.64 | 0.93 | 0.71 | 0.86 | 0.71 |
| AC | 0.8 | 0.8 | 0.83 | 0.8 | 0.77 | 0.83 | 0.8 | 0.77 | 0.8 |
| AU | 0.85 | 0.85 | 0.83 | 0.85 | 0.81 | 0.92 | 0.84 | 0.85 | 0.87 |
| PV | 1.90E-03 | 1.90E-03 | 3.40E-03 | 3.70E-03 | 1.10E-02 | 3.80E-05 | 8.60E-03 | 3.40E-03 | 1.20E-03 |

| # | miR-132 / miR-370 | miR-132 / miR-433 | miR-132 / miR-9 | miR-132 / miR-491-5p | miR-132 / miR-7 | miR-132 / miR-128a | miR-335-5p / miR-127-3p | miR-335-5p / miR-370 | miR-335-5p / miR-433 |
|---|---|---|---|---|---|---|---|---|---|
| SE | 0.69 | 0.88 | 0.94 | 0.75 | 0.75 | 0.81 | 0.81 | 0.69 | 0.63 |
| SP | 0.86 | 0.79 | 1 | 0.79 | 0.86 | 0.86 | 0.86 | 0.86 | 0.93 |
| AC | 0.77 | 0.83 | 0.97 | 0.77 | 0.8 | 0.83 | 0.83 | 0.77 | 0.77 |
| AU | 0.85 | 0.84 | 0.97 | 0.84 | 0.87 | 0.92 | 0.89 | 0.85 | 0.85 |
| PV | 1.90E-03 | 3.00E-03 | 2.60E-06 | 5.60E-03 | 2.50E-03 | 1.30E-04 | 1.30E-03 | 2.30E-03 | 2.20E-03 |

| # | miR-335-5p / miR-491-5p | miR-335-5p / miR-7 | miR-335-5p / miR-128a | miR-125b / miR-451 | miR-135a / miR-9 | miR-874 / miR-9 | miR-410 / miR-127-3p | miR-410 / miR-433 | miR-128a / miR-9 | miR-382 / miR-433 | miR-323-3p / miR-127-3p | miR-323-3p / miR-370 | miR-323-3p / miR-433 |
|---|---|---|---|---|---|---|---|---|---|---|---|---|---|
| SE | 0.88 | 0.75 | 0.88 | 0.81 | 0.75 | 0.75 | 1 | 0.81 | 0.69 | 0.88 | 0.88 | 0.88 | 0.81 |
| SP | 0.79 | 0.86 | 0.86 | 0.79 | 0.86 | 0.71 | 0.5 | 0.79 | 0.93 | 0.71 | 0.79 | 0.71 | 0.86 |
| AC | 0.83 | 0.8 | 0.87 | 0.8 | 0.8 | 0.73 | 0.77 | 0.8 | 0.8 | 0.8 | 0.83 | 0.8 | 0.83 |
| AU | 0.86 | 0.85 | 0.93 | 0.83 | 0.87 | 0.8 | 0.81 | 0.87 | 0.84 | 0.81 | 0.86 | 0.84 | 0.88 |
| PV | 1.40E-03 | 2.30E-03 | 1.60E-04 | 5.90E-03 | 6.30E-04 | 1.10E-02 | 6.30E-03 | 3.40E-03 | 3.40E-03 | 1.20E-02 | 1.00E-03 | 2.20E-03 | 1.00E-03 |

FIGURE 1B

| # | miR-135a / miR-433 | miR-135a / miR-370 | miR-135a / miR-127-3p | miR-135a / miR-125b | miR-134 / miR-433 | miR-134 / miR-370 | miR-134 / miR-127-3p | miR-134 / miR-410 | miR-134 / miR-382 |
|---|---|---|---|---|---|---|---|---|---|
| SE | 0.46 | 0.38 | 0.54 | 0.77 | 0.62 | 0.62 | 0.62 | 0.92 | 0.62 |
| SP | 0.94 | 0.94 | 0.88 | 0.63 | 0.88 | 0.88 | 0.81 | 0.56 | 0.75 |
| AC | 0.72 | 0.69 | 0.72 | 0.69 | 0.76 | 0.76 | 0.72 | 0.72 | 0.69 |
| AU | 0.81 | 0.78 | 0.77 | 0.75 | 0.81 | 0.84 | 0.77 | 0.77 | 0.76 |
| PV | 5.80E-03 | 1.40E-02 | 1.80E-02 | 3.00E-02 | 5.80E-03 | 3.80E-03 | 2.40E-02 | 1.30E-02 | 3.00E-02 |

| # | miR-335-5p / miR-433 | miR-335-5p / miR-370 | miR-335-5p / miR-127-3p | miR-491-5p / miR-433 | miR-491-5p / miR-370 | miR-491-5p / miR-125b | miR-128a / miR-433 | miR-128a / miR-370 | miR-323-3p / miR-433 |
|---|---|---|---|---|---|---|---|---|---|
| SE | 0.85 | 0.77 | 0.85 | 0.62 | 0.62 | 0.62 | 0.69 | 0.62 | 0.69 |
| SP | 0.75 | 0.75 | 0.63 | 0.81 | 0.75 | 0.81 | 0.75 | 0.75 | 0.88 |
| AC | 0.79 | 0.76 | 0.72 | 0.72 | 0.69 | 0.72 | 0.72 | 0.69 | 0.79 |
| AU | 0.81 | 0.8 | 0.78 | 0.79 | 0.77 | 0.75 | 0.78 | 0.75 | 0.9 |
| PV | 8.60E-03 | 1.30E-02 | 1.80E-02 | 1.60E-02 | 2.20E-02 | 6.50E-02 | 2.00E-02 | 2.80E-02 | 5.40E-04 |

| # | miR-323-3p / miR-370 | miR-323-3p / miR-127-3p | miR-382 / miR-433 | miR-382 / miR-370 |
|---|---|---|---|---|
| SE | 0.69 | 0.85 | 0.85 | 0.54 |
| SP | 0.88 | 0.88 | 0.75 | 0.94 |
| AC | 0.79 | 0.86 | 0.79 | 0.76 |
| AU | 0.87 | 0.85 | 0.84 | 0.77 |
| PV | 1.30E-03 | 2.70E-03 | 4.50E-03 | 2.30E-02 |

FIGURE 1C

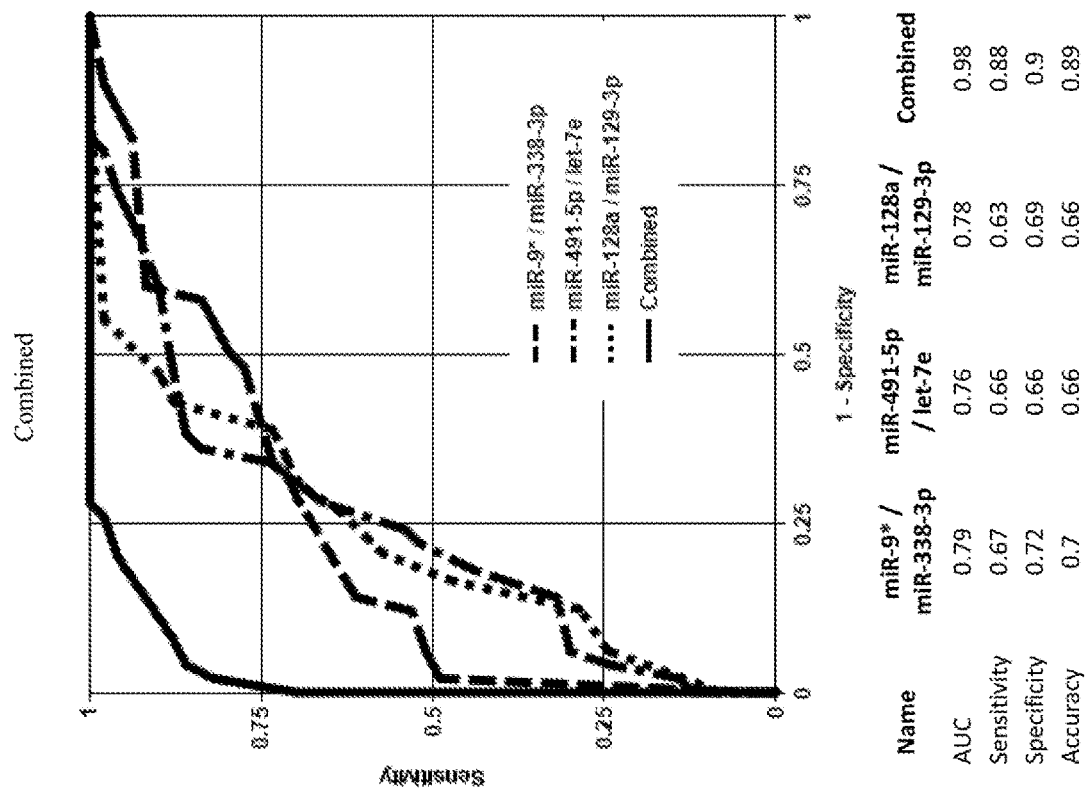

METHODS OF USING MIRNAS FROM BODILY FLUIDS FOR DETECTION AND DIFFERENTIATION OF NEURODEGENERATIVE DISEASES

CROSS-REFERENCE TO RELATED APPLICATIONS

This application is a U.S. National Phase application under 35 U.S.C. § 371 of International Patent Application No. PCT/US2017/023470, filed on Mar. 21, 2017, which claims priority from U.S. Provisional Application Ser. No. 62/310,979 filed on Mar. 21, 2016, and U.S. Provisional Application Ser. No. 62/365,663, filed on Jul. 22, 2016, all of which applications are incorporated herein by reference in their entireties.

STATEMENT AS TO FEDERALLY SPONSORED RESEARCH

This invention was made with government support under Grant No. AG044860 awarded by National Institutes of Health. The government has certain rights in the invention.

TECHNICAL FIELD OF THE INVENTION

The present invention is directed to methods for early detection, diagnosis, differentiation from each other, progression and treatment monitoring of various neurodegenerative diseases (NDs) by quantifying miRNAs in bodily fluids.

BACKGROUND OF THE INVENTION

Neurodegenerative diseases (NDs) are a large group of pathologies caused by metabolic changes in brain cells, loss of synapses and other compartments of neurons, and finally neuronal death (*Neurodegenerative diseases: From Molecular Concepts to Therapeutic Targets*. Editors: R. von Bernhardi, N.C. Inestrosa, Nova Publishers, 2008; *Neurodegenerative diseases: Clinical aspects, Molecular Genetics and Biomarkers*. Editors: D. Galimberti, E. Scarpini, Springer, 2014). This group of diseases includes Mild Cognitive Impairment (MCI), Alzheimer's disease (AD), Lewy Body dementia, Parkinson's disease (PD), Huntington's disease (HD), frontotemporal dementia (FTD), progressive supranuclear palsy (PSP), vascular dementia, multiple sclerosis (MS), amyotrophic lateral sclerosis (ALS), prion diseases, different ataxias, and others. Due to the increased lifespan, NDs become very common in developed countries. There are about 6 and 0.5 million people living with AD and PD, respectively, and 70-80 million people are in the risk group in the US only. Mechanisms of development of various NDs are not well understood although many underlying processes have been described. Drug development and successful treatment of NDs are significantly complicated by the absence of effective methods for their early diagnosis and monitoring. Development of effective diagnostic methods is further complicated by the strong brain potential to compensate for a long time the dysfunction and loss of neurons. This results in late clinical manifestation of disease symptoms when treatment cannot be very successful due to serious morphologic changes in the brain including the massive loss of neurons. Thus, diagnostic methods which are able to detect early events in ND development are particularly desirable.

NDs are characterized by neuronal death in different disease-specific areas of the brain. However, the neuronal loss is a relatively late event, typically following synaptic dysfunction, synaptic loss, neurite retraction, and the appearance of other abnormalities such as axonal transport defects (Bredesen, Molecular Neurodegeneration 2009, 4:27; Siskova et al., Am J Pathol. 2009, 175(4):1610-21; Kielar et al., Hum Mol Genet. 2009, 18(21):4066-4080; Nimmrich and Ebert, Rev Neurosci. 2009, 20:1-12; Bellizzi et al., J Neuroimmune Pharmacol. 2006, 1:20-31; Milnerwood and Raymond, J Physiol. 2007, 585:817-831; Waataja et al., J Neurochem. 2008, 104:364-375; Fuhrmann et al., J Neurosci. 2007, 27:6224-6233; Yoshiyama et al., Neuron. 2007, 53:337-351; Wishart et al., J Neuropathol Exp Neurol. 2006, 65:733-739; Gylys et al., Neurochem Int. 2004; 44:125-131; Conforti et al., Trends Neurosci. 2007, 30:159-166; Baloyannis et al., J Neurol Sci. 2006, 248:35-41; Diaz-Hernandez et al., FASEB J. 2009, 23:1893-1906; Spampanato et al., Neuroscience 2008, 157:606-620; Wade et al., Brain Res. 2008, 1188:61-68; Centonze et al., J Neurosci. 2009, 29:3442-3452; Wegner et al., Neurology. 2006, 67:960-967; Dupuis and Loeffler, Curr Opin Pharmacol. 2009, 9:341-346; Revuelta, et al. Am J Alzheimers Dis Other Demen 2008 23: 97-102). Numerous studies are devoted to description of axon destruction with shedding of membrane-enclosed "axosomes", axon, dendrite and spine pruning, and disassembly of synapses (Goda, Davis, Neuron 2003, 40:243-264; Eaton, Davis, Genes Development, 2003, 17:2075-2082; Koiral, Ko, Neuron, 2004, 44:578-580; Bishop et al., Neuron, 2004, 44:651-661; Low, Cheng, Phil. Trans. R. Soc. B 2006 361, 1531-1544).

Alzheimer's disease (AD) is characterized by neuronal death in several disease-specific areas of the brain, such as hippocampus and cortex. However, the neuronal loss is a relatively late event in the disease progression that typically is preceded by synaptic dysfunction, synaptic loss, neurite retraction, and the appearance of other abnormalities such as axonal transport defects. The first symptomatic stage of Alzheimer's disease that is manifested by mild clinical symptoms is Mild Cognitive Impairment (MCI), which is usually defined as an intermediate state between normal aging and dementia (DeCarli, Lancet Neurol., 2003, 2:15-21; Stephan et al., Alzheimer's Res Therapy, 2009, 1:1-9; Apostolova et al., Human Brain Mapping, 2010, 31:786-797). On average, MCI patients convert to dementia at a rate of 10-15% annually (Petersen et al., Arch Neurol. 2001, 58:1985-1992; Apostolova et al., Human Brain Mapping, 2010, 31:786-797). However, currently the MCI outcome is not reliably predictable. First, up to 40% of MCI patients revert to normal status (Larrieu et al., Neurology, 2002, 59:1594-1599; Brooks, Loewenstein, Alzheimer's Res Therapy, 2010, 2:28-36), and autopsy studies demonstrate that a substantial percentage of MCI patients do not have evidence of AD pathology (Jicha et al., Arch Neurol, 2006, 63:674-681; Khan, Alkon, Neurobiol. Aging, 2010, 31:889-900). Second, about 20% of MCI patients who convert to dementia are diagnosed not with AD but other neurodegenerative diseases, such as vascular, Lewy body, Huntington, Parkinson, and other dementias (Jicha et al., Arch Neurol, 2006, 63:674-681; Stephan et al., Alzheimer's Res Therapy, 2009, 1:1-9). Third, disease progression varies for AD patients from slow to intermediate and rapid (Doody et al., Alzheimer's Res Therapy, 2010, 2:2-10). Even clinically MCI is not a homogeneous pathology and can be described as two conditions, with amnestic symptoms (aMCI) and without amnestic symptoms (Dlugaj et al., Dement Geriatr Cogn Disord., 2010, 30:362-373; Brooks, Loewenstein, Alzheimer's Res Therapy, 2010, 2:28-36). Some publications have demonstrated that aMCI converts to dementia much more often and is a better predictor of AD (Mariani et al., J Alzheimer's Dis., 2007, 12:23-35; Luck et al., Psychiatr Prax., 2008, 35:331-336; Koivunen et al., Neurology, 2011, 76:1085-1099). However, other authors have not found significant difference in the conversion rate for two MCI forms (Rountree et al., Dement Geriatr Cogn Disord., 2007, 24:476-482).

As mentioned above, due to effective compensatory mechanisms in the brain, the decrease of cognitive function is usually registered when a disease is in the middle or even late stages and fewer treatments are available. New imaging techniques which are becoming increasingly popular (e.g., positron emission tomography (PET), computed tomography (CT), magnetic resonance imaging (MRI), multiphoton imaging, etc.) although helpful currently are not sufficiently sensitive and specific for detecting the early stage of a disease before major morphological changes occur (Mucke, Nature, 2009, 461:895-897; Mistur et al., J. Clin. Neurol., 2009, 5:153-166; Miller, Science, 2009, 326:386-389; Perrin et al. Nature, 2009, 461: 916-922). Analysis of various proteins in the cerebrospinal fluid (CSF) is another approach for early ND diagnosis (Meyer et al., Arch Neurol. 2010, 67:949-956; Chen-Plotkin A., Neuron 2014, 84: 594-607; Sacesario G M and Bernandini S. Crit. Rev. Clin. Lab. Sci. 2015, 52: 314-326) but these methods are too invasive and expensive to be widely used.

Thus, there is still a great need in the art to develop methods for diagnosis and diseases and treatment monitoring of NDs and other neurological disorders. It is also important that ND progression usually leads to pathology expansion to new brain areas. This results in difficulties of differential diagnosis of various NNDs in clinical practice. Besides, two NDs in one patient is not a rare event, which additionally complicates diagnostics of pathology and its treatments.

Recently, the present inventors have proposed a new approach for early detection of NDs based on analysis of circulating cell-free miRNA in bodily fluids (Sheinerman et al. Aging (Albany N.Y.). 2012; 4: 590-605; Sheinerman and Umansky. Cell Cycle. 2013; 12: 1-2; Sheinerman and Umansky. Front Cell Neurosci. 2013; 7: 150; Sheinerman et al. Aging (Albany N.Y.). 2012; 5: 925-938; International Pat. Publ. Nos. WO2012/145363 and WO2011/057003).

MicroRNAs (miRNAs) are a class of non-coding RNAs whose final product is an approximately 22 nt functional RNA molecule. They play important roles in the regulation of target genes by binding to complementary regions of messenger transcripts to repress their translation or regulate degradation (Griffiths-Jones Nucleic Acids Research. 2006; 34, Database issue: D140-D144; Cloonan N., Bioassay. 2015, 37: 379-388; Chou-Hung et al. Nucleic Acids Research. 2016, 44: 239-247). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al. Nature. 2008; 455:64; Selbach et al. Nature. 2008; 455:58; Ambros. Nature. 2004; 431: 350-355; Bartel. Cell. 2004; 116: 281-297; Cullen. Virus Research. 2004; 102: 3-9; He et al. Nat. Rev. Genet. 2004; 5: 522-531; and Ying et al. Gene. 2004; 342: 25-28). There are other classes of less characterized small RNAs (Kim. Mol. Cells. 2005; 19: 1-15; Leung Y Y. Et al. Nucleic Acids Res. 2016, 44: 216-222).

Many of miRNAs are specific to or over-expressed in certain organs/tissues/cells (see, e.g., Hua et al. BMC Genomics. 2009; 10:214; Liang et al. BMC Genomics. 2007; 8:166; Landgraf et al. Cell. 2007; 129:1401-1414; Lee et al. RNA. 2008; 14:35-42) and in different brain areas, such as hippocampus, midbrain, frontal cortex, pituitary gland, and in different cell types, such as neurons and glial cells (Sempere et al. Genome Biol. 2004; 5: R13; Deo et al. Dev. Din. 2006; 235:2538-2548; Bak et al. RNA. 2008; 14: 432-444; Trivedi and Ramakrishna Int. J. Neurosci. 2009; 119: 1995-2016; Weng et al. Biomed. Res. 2011; 32: 135-141; He et al. Neuron. 2012; 73: 35-48; ZiatsMN and Rennert O M. Mol Psychiatry. 2014, 19: 848-852; Hamilton D E et al. Physiol. Genomics. 2014, 46: 290-301).

Some miRNAs, including those that are cell-specific, are enriched in certain cellular compartments, particularly in axons, dendrites and synapses (see, e.g., Schratt et al. Nature. 2006; 439:283-289; Lugli et al. J. Neurochem. 2008; 106:650-661; Bicker and Schratt. J. Cell. Mol. Med. 2008; 12:1466-1476; Smalheiser and Lugli. Neuromolecular Med. 2009; 11:133-140; Rajasethupathy. Neuron. 2009; 63:714-716; Kye. RNA. 2007; 13:1224-1234; Yu et al. Exp Cell Res. 2008; 314:2618-2633; Cougot et al. J. Neurosci. 2008; 28:13793-13804; Kawahara. Brain Nerve. 2008. 60:1437-1444; Schratt G. Rev Neurosci. 2009; 10:842-849; Pichardo-Casas et al. Brain Research. 2012; 1436:20-33).

An approach based on analysis of cell/tissue-specific miRNAs in bodily fluids was proposed for detection of in vivo cell death (U.S. Patent Pub. No 20090081640). Such technique was successfully used for detection of acute cell death after tissue injury, including neuronal death after stroke (Liu et al., Journal of Cerebral Blood Flow & Metabolism 2010, 30:92-101; Laterza et al., Clin Chem. 2009, 55:1977-1983). While this technique may allow the detection of neuronal cell death, it does not provide an opportunity for early diagnosis of neurodegeneration and other neurological disorders prior to massive neuronal death.

Expression and concentrations of miRNAs are regulated by various physiological and pathological signals. Changes in expression of some miRNAs were found in neurons of Parkinson's, Alzheimer's and other neurodegenerative disease patients (Hebert and De Strooper. Trends Neurosci. 2009; 32:199-206; Saba et al. PLoS One. 2008; 3:e3652; Kocerha et al. Neuromolecular Med. 2009; 11:162-172; Sethi and Lukiw. Neurosci Lett. 2009; 459:100-104; Zeng; Mol Pharmacol. 2009; 75:259-264; Cogswell et al. Journal of Alzheimer's disease. 2008; 14: 27-41; Schaefer et al. J. Exp. Med. 2007; 204:1553-1558; Hebert. Proc. Natl. Acad. Sci. USA. 2008; 105:6415-6420; Wang et al. J. Neurosci. 2008; 28:1213-1223; Nelson et al. Brain Pathol. 2008; 18:130-138; Lukiw. Neuroreport. 2007; 18:297-300).

For the use of miRNA in diagnostics, it is also important that miRNA secretion varies depending on cellular physiology (Palma et al. Nucleic Acids Res. 2012; 40:9125-9138; Pigati et al. PLoS One. 2010; 5: e13515). In addition to miRNA release into extracellular space and subsequent appearance in the bodily fluids due to cell death, miRNA appear in circulation due to blebbing of apoptotic bodies, budding and shedding of microvesicles, active secretion in the form of exosomes and of miRNA complexes with proteins (AGO2, NPM1 and others) and high density lipoproteins (HDL) (reviews: Sun et al. Clin. Chem. Lab. Med. 2012; 50: 2121-2126; Zandberga et al. Genes Chromosomes Cancer. 2013; 52: 356-369). All these forms of cell-free miRNA are highly stable in the bloodstream and other bodily fluids. The secretion of miRNA is selective and can be significantly changed by various pathological processes.

For example, changes in the spectrum of miRNA secreted in exosomes from prion-infected neuronal cells, as compared to uninfected cells, have been demonstrated (Belingham et al. Nucleic Acids Res. 2012; 40: 10937-10949).

Two approaches are widely used for searching miRNA biomarkers of various diseases in bodily fluids:

1. Measurement of hundreds of different miRNA in a bodily fluid from patients with a pathology of interest and from control subjects using miRNA array or next generation sequencing (NGS) (Qin et al. Cancer Inform. 2013; 12: 83-101). While this approach allows to analyze a huge numbers of various miRNA, currently the miRNA array-based and sequencing techniques are not sufficiently sensitive to detect many miRNA whose concentration in bodily fluids is relatively low. As a consequence, most of the miRNA detectable in bodily fluids by arrays and NGS are ubiquitous miRNA expressed in all or many tissues, and many of them derive from blood cells (Pritchard et al. Cancer Prev. Res. (Phila). 2012; 5:492-497; Leidner and Thompson. PLoS One. 2013; 8: 57841). The detection of changes in the concentrations of such ubiquitous miRNA in patients with one pathology does not mean that the same miRNA cannot be involved in other diseases of different organs. Many miRNA are associated with a particular pathology type, such as cancer, inflammation, hypoxia, etc., and changes in their concentration in bodily fluids can be associated with diseases of different organs. For example, changes of miR-155 concentrations were found in the bloodstream of patients with breast, esophageal, lung, pancreatic cancers and lymphomas (Blair and Yan. DNA Cell Biol. 2012; 31 Suppl. 1: S49-61; Xie et al. Bioinformatics. 2013; 29: 638-644). Level of miR-21 increases in plasma/serum of patients with osteosarcoma, bladder, esophageal, gastric, lung, breast, colorectal cancers, neck squamous cell carcinoma and other tumors (Blair and Yan. DNA Cell Biol. 2012; 31 Suppl. 1: S49-61; Farazi et al. J. Pathol. 2011; 223: 102-115; Xie et al, Bioinformatics. 2013; 29: 638-644). It follows that the potential biomarkers found by miRNA arrays should be also tested in other pathologies, not only in healthy control subjects.

2. The second approach is based on analysis of disease-specific miRNAs identified by comparison of miRNAs isolated from pathologic and normal tissue, organ or cell type. Here, subsequent to identification of disease-specific miRNAs (e.g., by an array followed by RT-PCR), their presence in bodily fluids is analyzed. In this strategy, since a limited number of circulating miRNAs is tested, the use of individual RT-PCR is possible which allows to increase sensitivity and reproducibility of the analysis. However, in many cases when this method was applied, no correlation was detected between miRNA concentration and pathology-induced changes in the tissue and in bodily fluids (Boeri et al., Proc. Natl. Acad. Sci. USA. 2011; 108: 3713-3718; Cuk et al. Int. J. Cancer. 2013; 132: 1602-1612).

The present invention is based on realization that since neurite destruction and synapse loss as well as some metabolic events precede neuronal death in the course of development of NDs and other neurological disorders, methods based on detection of those phenomena could be used for earlier disease diagnosis than the ones based on detecting cell death. In addition, due to expansion of pathological processes to new brain regions during ND progression, this phenomenon can be used for disease and treatment monitoring.

SUMMARY OF THE INVENTION

There is a great need in the art in sensitive methods of early detection of NDs such as Alzheimer's disease (AD) (including its asymptomatic (pre-MCI) and Mild Cognitive Impairment (MCI) stages), Parkinson's disease (PD), frontotemporal dementia (FTD), progressive supranuclear palsy (PSP), amyotrophic lateral sclerosis (ALS), and others. The present invention addresses this and other needs by providing novel highly sensitive and noninvasive or minimally invasive diagnostic methods based on quantification of small RNAs in bodily fluids.

In one aspect, the invention provides a method for detecting a neurodegenerative disorder in a subject, which method comprises:

a) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNAs measured in steps (a) and (b);

d) optionally comparing the ratio of the levels of the miRNAs calculated in step (c) with a corresponding control ratio, and e) optionally (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio.

In one aspect, the invention provides a method for detecting a neurodegenerative disorder in a subject, which method comprises:

f) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

g) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

h) calculating the ratio of the levels of the miRNAs measured in steps (a) and (b);

i) comparing the ratio of the levels of the miRNAs calculated in step (c) with a corresponding control ratio, and j) (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio.

In one embodiment, the method further comprises refining the diagnosis by the following steps, which steps can be performed simultaneously or sequentially with each other and/or with the steps (d)-(e) of the above method:

k) comparing the ratio of the levels of the miRNAs calculated in step (c) with the standard range of ratios of said miRNAs characteristic of another neurodegenerative disorder ("a second neurodegenerative disorder"), and l) (i) excluding the diagnosis of the second neurodegenerative disorder in the subject if the ratio of the levels of the miRNAs calculated in step (c) does not fall within the standard range of ratios of said miRNAs characteristic of the second neurodegenerative disorder, or (ii) not excluding the diagnosis of the second neurodegenerative disorder in the subject if the ratio of the levels of the miRNAs calculated in step (c) falls within the standard range of ratios of said miRNAs characteristic of the second neurodegenerative disorder.

In one embodiment of any of the above methods, step (c) involves (1) calculating using a suitably programmed processor, the ratio of the levels of the miRNAs measured in steps (a) and (b);

(2) calculating, by the processor and based on the ratio determined in step (c)(1), a first probability based on a first predefined probability distribution curve, wherein the first predefined probability distribution curve corresponds to the neurodegenerative disorder;

(3) calculating, by the processor and based on the ratio determined in step (c)(1), a second probability based on a second predefined probability distribution curve, wherein the second predefined probability distribution curve corresponds to a matched control (e.g., matched by gender and/or age and/or race, etc.) or another pathology;

step (d) involves determining, by the processor, a difference between the first probability calculated in step (c)(2) and the second probability calculated in step (c)(3), and step (e) involves (i) identifying, by the processor, the subject as being afflicted with the neurodegenerative disorder when the difference between the first probability and the second probability calculated in step (d) is positive or (ii) identifying the subject as not being afflicted with the neurodegenerative disorder when the difference between the first probability and the second probability calculated in step (d) is negative.

In another aspect, the invention provides a method for treating a neurodegenerative disorder in a subject, which method comprises:

a) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio, and f) administering a therapeutic or preventive treatment to the subject.

In another aspect, the invention provides a method for treating a neurodegenerative disorder in a subject, which method comprises:

a) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNAs measured in steps (a) and (b);

d) comparing the ratio of the levels of the miRNAs calculated in step (c) with a corresponding control ratio;

e) (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio, and f) administering a therapeutic or preventive treatment to the subject.

In yet another aspect, the invention provides a method for selecting subjects for enrollment in a clinical trial involving treatment of a neurodegenerative disorder, which method comprises:

a) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio, and f) recruiting the subject in a clinical trial.

In yet another aspect, the invention provides a method for selecting subjects for enrollment in a clinical trial involving treatment of a neurodegenerative disorder, which method comprises:

a) measuring the level of a first brain-enriched miRNA (e.g., synapse and/or neurite miRNA) in a bodily fluid sample collected from the subject, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNAs measured in steps (a) and (b);

d) comparing the ratio of the levels of the miRNAs calculated in step (c) with a corresponding control ratio;

e) (i) identifying the subject as being afflicted with the neurodegenerative disorder when the ratio of the levels of the miRNAs calculated in step (c) is higher than the corresponding control ratio or (ii) identifying the subject as not being afflicted with the neurodegenerative disorder when the ratio of the levels of the miRNA calculated in step (c) is not higher than the corresponding control ratio, and f) recruiting the subject in a clinical trial.

In one embodiment of any of the above methods, the control ratio is a predetermined value which represents a statistically validated threshold ratio of the levels of said first and second miRNAs (a single "cut-off" value) equal to the highest possible value within the range of corresponding values in matched healthy subjects (e.g., matched by gender and/or age and/or race, etc.). In another embodiment of any of the above methods of disease detection, the control ratio is the ratio of the levels of said first and second miRNAs in a similarly processed bodily fluid sample from the same subject collected in the past.

In one embodiment of any of the above methods of disease differentiation, the standard range of ratios of miRNAs characteristic of the second neurodegenerative disorder is a statistically validated predetermined range of values established by determining the ratios of the same miRNAs in a large cohort of subjects diagnosed with the second neurodegenerative disorder. In one specific embodiment, the cohort of subjects diagnosed with the second pathology represents a full range of development stages of said second neurodegenerative disorder. In another specific embodiment, the cohort of subjects diagnosed with the second neurodegenerative disorder represents one or more development stages of said second neurodegenerative disorder.

In one embodiment of any of the above methods of disease differentiation, said first neurodegenerative disorder and said second neurodegenerative disorder are selected from the group consisting of Alzheimer's disease (AD), Parkinson's disease (PD), frontotemporal dementia (FTD), and amyotrophic lateral sclerosis (ALS).

In another aspect, the invention provides a method for monitoring changes in development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in two or more bodily fluid samples collected from the subject, wherein said first brain-enriched miRNA is enriched in a brain area(s) affected by the neurodegenerative disorder;

b) measuring the level of a second brain-enriched miRNA in the same bodily fluids samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that the neurodegenerative disorder in the subject has progressed if the ratio of the levels of the miRNA calculated in step (c) is increased in the later collected bodily fluid sample(s) as compared to the earlier collected sample(s), or (ii) determining that the neurodegenerative disorder in the subject has not progressed if the ratio of the levels of the miRNA calculated in step (c) is not changed in the later collected bodily fluid sample(s) as compared to the earlier collected sample(s).

In one embodiment, the first brain-enriched miRNA is synapse and/or neurite miRNA.

In another aspect, the invention provides a method for monitoring changes in development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in two or more bodily fluid samples collected from the subject at spaced apart time points, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNAs measured in steps (a) and (b);

d) optionally measuring the level of the third brain-enriched miRNA in the same bodily fluids samples as in step (a), wherein said third brain-enriched miRNA is enriched in a brain area(s) affected by the later stages of the neurodegenerative disorder;

e) optionally measuring the level of the fourth miRNA as in step (b) in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) calculating the ratio of the levels of the miRNA measured in steps (d) and (e);

g) comparing the ratios of the levels of the miRNA calculated in steps (c) and (f) between the earlier collected and later collected bodily fluid sample(s), and h) (i) determining that the neurodegenerative disorder in the subject has progressed if the ratio determined in step (c) is decreased and the ratio determined in step (f) is increased in the later collected bodily fluid sample(s) as compared to the earlier collected sample(s), or (ii) determining that the neurodegenerative disorder in the subject has not progressed if the ratio determined in step (c) is not changed or is decreased and the ratio determined in step (f) is not increased in the later collected bodily fluid sample(s) as compared to the earlier collected sample(s).

In another aspect, the invention provides a method for monitoring changes in development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in two or more bodily fluid samples collected from the subject at spaced apart time points, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNAs measured in steps (a) and (b);

d) measuring the level of the third brain-enriched miRNA in the same bodily fluids samples as in step (a), wherein said third brain-enriched miRNA is enriched in a brain area(s) affected by the later stages of the neurodegenerative disorder;

e) measuring the level of the fourth miRNA as in step (b) in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) calculating the ratio of the levels of the miRNA measured in steps (d) and (e);

g) comparing the ratios of the levels of the miRNA calculated in steps (c) and (f) between the earlier collected and later collected bodily fluid sample(s), and h) (i) determining that the neurodegenerative disorder in the subject has progressed if the ratio determined in step (c) is decreased and the ratio determined in step (f) is increased in the later collected bodily fluid sample(s) as compared to the earlier collected sample(s), or (ii) determining that the neurodegenerative disorder in the subject has not progressed if the ratio determined in step (c) is not changed or is decreased and the ratio determined in step (f) is not increased in the later collected bodily fluid sample(s) as compared to the earlier collected sample(s).

In yet another separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNA measured in steps (a) and (b);

d) optionally measuring the level of the same first miRNA as in step (a) in one or more bodily fluid sample(s) collected from the subject in the course of or following the treatment;

e) optionally measuring the level of the same second miRNA as in step (b) in the same bodily fluid sample(s) as in step (d);

f) optionally calculating the ratio of the levels of the miRNA measured in steps (d) and (e) for each bodily fluid sample;

g) optionally comparing the ratios of the levels of the miRNA calculated in steps (c) and (f), and comparing the ratios of the levels of the miRNA calculated in step (f) between different samples in step (d), and h) optionally (i) determining that the treatment is effective for said neurodegenerative disorder if the ratio of the levels of the miRNA calculated in step (c) is higher than the corresponding ratio(s) calculated in step (f), or (ii) determining that the treatment is not effective for said neurodegenerative disorder if the ratio of the levels of the miRNA calculated in step (c) is not higher than the corresponding ratio(s) calculated in step (f).

In yet another separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and comparing the ratios of the levels of the miRNA calculated in step (f) between different samples in step (d), and h) (i) determining that the treatment is effective for said neurodegenerative disorder if the ratio of the levels of the miRNA calculated in step (c) is higher than the corresponding ratio(s) calculated in step (f), or (ii) determining that the treatment is not effective for said neurodegenerative disorder if the ratio of the levels of the miRNA calculated in step (c) is not higher than the corresponding ratio(s) calculated in step (f).

In a separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment, wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) optionally calculating the ratio of the levels of the miRNA measured in steps (d) and (e) for each bodily fluid sample;

g) optionally comparing the ratios of the levels of the miRNA calculated in steps (c) and (f), and optionally comparing the ratios of the levels of the miRNA calculated in step (f) between different samples in step (d), and h) optionally (i) determining that the treatment is effective for said neurodegenerative disorder if the ratio of the levels of the miRNA calculated in step (c) is higher than the corresponding ratio(s) calculated in step (f), or (ii) determining that the treatment is not effective for said neurodegenerative disorder if the ratio of the levels of the miRNA calculated in step (c) is not higher than the corresponding ratio(s) calculated in step (f).

In a separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment and in one or more bodily fluid sample(s) collected from the subject in the course of or following the treatment, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNA measured in steps (a) and (b);

d) measuring the level of the third brain-enriched miRNA in the same bodily fluids samples as in step (a), wherein said third brain-enriched miRNA is enriched in a brain area(s) affected by the later stages of the neurodegenerative disorder;

e) measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) calculating the ratio of the levels of the miRNAs measured in steps (d) and (e);

g) comparing the ratios of the levels of the miRNAs calculated in steps (c) and (f) between the sample obtained before the treatment and sample(s) obtained in the course of or following the treatment, and h) (i) determining that the treatment is effective for said neurodegenerative disorder if the ratio of the levels of the miRNAs calculated in step (c) is not changed or is decreased and the ratio determined in step (f) is not increased in the sample(s) obtained in the course of or following the treatment as compared to the sample obtained before the treatment, or (ii) determining that the treatment is not effective for said neurodegenerative disorder if the ratio determined in (c) is decreased and the ratio determined in (f) is increased in the sample(s) obtained in the course of or following the treatment as compared to the sample obtained before the treatment.

In yet another separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment and in one or more bodily fluid sample(s) collected from the subject in the course of or following the treatment, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) optionally calculating the ratio of the levels of the miRNA measured in steps (a) and (b);

d) optionally measuring the level of the third brain-enriched miRNA in the same bodily fluids samples as in step (a), wherein said third brain-enriched miRNA is enriched in a brain area(s) affected by the later stages of the neurodegenerative disorder;

e) optionally measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) optionally calculating the ratio of the levels of the miRNAs measured in steps (d) and (e);

g) optionally comparing the ratios of the levels of the miRNAs calculated in steps (c) and (f) between the sample obtained before the treatment and sample(s) obtained in the course of or following the treatment, and h) optionally (i) determining that the treatment is effective for said neurodegenerative disorder if the ratio of the levels of the miRNAs calculated in step (c) is not changed or is decreased and the ratio determined in step (f) is not increased in the sample(s) obtained in the course of or following the treatment as compared to the sample obtained before the treatment, or (ii) determining that the treatment is not effective for said neurodegenerative disorder if the ratio determined in (c) is decreased and the ratio determined in (f) is increased in the sample(s) obtained in the course of or following the treatment as compared to the sample obtained before the treatment.

In another separate aspect, the invention provides a method for monitoring the effect of a treatment on development of a neurodegenerative disorder in a subject (e.g., a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to initiation of the treatment and in one or more bodily fluid sample(s) collected from the subject in the course of or following the treatment, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNA measured in steps (a) and (b);

d) measuring the level of the third brain-enriched miRNA in the same bodily fluids samples as in step (a), wherein said third brain-enriched miRNA is enriched in a brain area(s) affected by the later stages of the neurodegenerative disorder;

e) measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) calculating the ratio of the levels of the miRNAs measured in steps (d) and (e);

g) comparing the ratios of the levels of the miRNAs calculated in steps (c) and (f) between the sample obtained before the treatment and sample(s) obtained in the course of or following the treatment, and h) (i) determining that the treatment is effective for said neurodegenerative disorder if the ratio of the levels of the miRNAs calculated in step (c) is not changed or is decreased and the ratio determined in step (f) is not increased in the sample(s) obtained in the course of or following the treatment as compared to the sample obtained before the treatment, or (ii) determining that the treatment is not effective for said neurodegenerative disorder if the ratio determined in (c) is decreased and the ratio determined in (f) is increased in the sample(s) obtained in the course of or following the treatment as compared to the sample obtained before the treatment.

In a separate aspect, the invention provides a method for identifying a compound useful for slowing down the progression or treating a neurodegenerative disorder in a subject (a subject who had been previously diagnosed with said neurodegenerative disorder), which method comprises:

a) measuring the level of a first brain-enriched miRNA (e.g., synapse and/or neurite miRNA) in a bodily fluid sample, wherein said bodily fluid sample(s) is collected from the subject prior to test compound administration, and wherein said first brain-enriched miRNA is enriched in a brain area(s) affected by the neurodegenerative disorder;

b) measuring the level of a second brain-enriched miRNA in the same bodily fluid sample collected from the subject, wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;
c) optionally calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) optionally calculating the ratio of the levels of the miRNAs measured in steps (d) and (e) for each of the bodily fluid samples collected from the subject following administration of the test compound;
g) optionally comparing the ratio of the levels of the miRNA calculated in steps (c) and (f), and
h) optionally (i) identifying that the test compound is useful for slowing down the progression or treating the neurodegenerative disorder if the ratio of the levels of the miRNA calculated in step (f) is lower than the ratio of the levels of the miRNA calculated in step (c); (ii) identifying that the test compound is not useful for slowing down the progression or treating the neurodegenerative disorder if the ratio of the levels of the miRNA calculated in step (f) is not lower than the ratio of the levels of the miRNAs calculated in step (c).

In a separate aspect, the invention provides a method for identifying a compound useful for slowing down the progression or treating a neurodegenerative disorder in a subject (a subject who had been previously diagnosed with said neurodegenerative disorder), which method comprises:
a) measuring the level of a first brain-enriched miRNA (e.g., synapse and/or neurite miRNA) in a bodily fluid sample collected from the subject prior to test compound administration and in one or more bodily fluid sample(s) collected from the subject following administration of a test compound, wherein said first brain-enriched miRNA is enriched in a brain area(s) affected by the earlier stages of the neurodegenerative disorder;
b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;
c) calculating the ratio of the levels of the miRNA measured in steps (a) and (b);
d) measuring the level of the third brain-enriched miRNA in the same bodily fluids samples as in step (a), wherein said third brain-enriched miRNA is enriched in a brain area(s) affected by the later stages of the neurodegenerative disorder;
e) measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;
f) calculating the ratio of the levels of the miRNAs measured in steps (d) and (e);
g) comparing the ratios of the levels of the miRNAs calculated in steps (c) and (f) between the samples obtained before and after the test compound administration, and
h) (i) identifying that the test compound is useful for slowing down the progression or treating the neurodegenerative disorder if the ratio of the levels of the miRNAs calculated in step (c) is not changed or is decreased and the ratio determined in step (f) is not increased in the sample(s) obtained after the test compound administration as compared to the sample obtained before the test compound administration, or (ii) (i) identifying that the test compound is not useful for slowing down the progression or treating the neurodegenerative disorder if the ratio determined in (c) is decreased and the ratio determined in (f) is increased in the sample(s) obtained after the test compound administration as compared to the sample obtained before the test compound administration.

In another separate aspect, the invention provides a method for identifying a compound useful for slowing down the progression or treating a neurodegenerative disorder in a subject (a subject who had been previously diagnosed with said neurodegenerative disorder), which method comprises:
a) measuring the level of a first brain-enriched miRNA (e.g., synapse and/or neurite miRNA) in a bodily fluid sample collected from the subject prior to test compound administration and in one or more bodily fluid sample(s) collected from the subject following administration of a test compound, wherein said first brain-enriched miRNA is enriched in a brain area(s) affected by the earlier stages of the neurodegenerative disorder;
b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;
c) optionally calculating the ratio of the levels of the miRNA measured in steps (a) and (b);
d) optionally measuring the level of the third brain-enriched miRNA in the same bodily fluids samples as in step (a), wherein said third brain-enriched miRNA is enriched in a brain area(s) affected by the later stages of the neurodegenerative disorder;
e) optionally measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;
f) optionally calculating the ratio of the levels of the miRNAs measured in steps (d) and (e);
g) optionally comparing the ratios of the levels of the miRNAs calculated in steps (c) and (f) between the samples obtained before and after the test compound administration, and h) optionally (i) identifying that the test compound is useful for slowing down the progression or treating the neurodegenerative disorder if the ratio of the levels of the miRNAs calculated in step (c) is not changed or is decreased and the ratio determined in step (f) is not increased in the sample(s) obtained after the test compound administration as compared to the sample obtained before the test compound administration, or (ii) (i) identifying that the test compound is not useful for slowing down the progression or treating the neurodegenerative disorder if the ratio determined in (c) is decreased and the ratio determined in (f) is increased in the sample(s) obtained after the test compound administration as compared to the sample obtained before the test compound administration.

In another aspect, the invention provides a method for identifying a compound useful for slowing down the progression or treating a neurodegenerative disorder in a subject (a subject who had been previously diagnosed with said neurodegenerative disorder), which method comprises:

a) measuring the level of a first brain-enriched miRNA (e.g., synapse and/or neurite miRNA) in a bodily fluid sample collected from the subject prior to test compound administration and in one or more bodily fluid sample(s) collected from the subject following administration of a test compound, wherein said first brain-enriched miRNA is enriched in a brain area(s) affected by the earlier stages of the neurodegenerative disorder;

b) measuring the level of a second brain-enriched miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

c) calculating the ratio of the levels of the miRNA measured in steps (a) and (b);

d) measuring the level of the third brain-enriched miRNA in the same bodily fluids samples as in step (a), wherein said third brain-enriched miRNA is enriched in a brain area(s) affected by the later stages of the neurodegenerative disorder;

e) measuring the level of the fourth miRNA in the same bodily fluid samples as in step (a), wherein said second brain-enriched miRNA (i) is enriched in a brain area(s) which is not affected by the neurodegenerative disorder, or (ii) is enriched in a brain cell type which is not affected by the neurodegenerative disorder, or (iii) is enriched in the same brain area as the first miRNA, but its expression and/or secretion change differently than expression and/or secretion of the first miRNA during development of the neurodegenerative disorder;

f) calculating the ratio of the levels of the miRNAs measured in steps (d) and (e);

g) comparing the ratios of the levels of the miRNAs calculated in steps (c) and (f) between the samples obtained before and after the test compound administration, and h) (i) identifying that the test compound is useful for slowing down the progression or treating the neurodegenerative disorder if the ratio of the levels of the miRNAs calculated in step (c) is not changed or is decreased and the ratio determined in step (f) is not increased in the sample(s) obtained after the test compound administration as compared to the sample obtained before the test compound administration, or (ii) (i) identifying that the test compound is not useful for slowing down the progression or treating the neurodegenerative disorder if the ratio determined in (c) is decreased and the ratio determined in (f) is increased in the sample(s) obtained after the test compound administration as compared to the sample obtained before the test compound administration.

In one embodiment of any of the above methods, the neurodegenerative disorder is selected from the group consisting of Mild Cognitive Impairment (MCI), pre-MCI, Alzheimer's disease (AD), Parkinson's disease (PD), frontotemporal dementia (FTD), and amyotrophic lateral sclerosis (ALS).

In one embodiment of any of the above methods, the first brain-enriched miRNA is a synapse and/or neurite miRNA.

In one embodiment of any of the above methods, the second miRNA is a brain-enriched miRNA, which (1) is enriched in a brain area(s) which is not affected by the neurodegenerative disorder or (2) is enriched in a brain cell type which is not affected by the neurodegenerative disorder. In one embodiment of any of the above methods, the second miRNA is a brain-enriched miRNA selected from the group consisting of miRNAs which are mainly expressed in brain areas not involved in said neurodegenerative disorder, miRNAs which are mainly expressed in glial cells, and brain-enriched miRNAs downregulated in said neurodegenerative disorder.

In one embodiment of any of the above methods, the pair of the first miRNA and the second miRNA is selected from the pairs provided in Tables 3-23 and 25-26, below.

In one embodiment of any of the above methods, the method comprises measuring the level and calculating the ratios of the levels for two or more different pairs of miRNA, wherein the comparison involves using Logistic Regression to determine the probability of a subject belonging to one of two possible groups (i) and (ii) in the identifying/determining step, wherein the probability has to be higher than 0.5 for the subject to belong to one of said groups.

In one specific embodiment, the method comprises measuring the level and calculating the ratios of the levels for one or more pair combinations selected from the pair combinations provided in Tables 7-10, 13, 15, 17, 19, 21, 23, and 26, below.

In one embodiment of any of the above methods, the neurodegenerative disorder is an early stage of AD (e.g., MCI or pre-MCI) and the first brain-enriched miRNA is synapse and/or neurite miRNA enriched in hippocampus. In another embodiment of any of the above methods, the neurodegenerative disorder is AD (dementia stages) and the first brain-enriched miRNA is enriched in brain cortex. In another embodiment of any of the above methods, the neurodegenerative disorder is AD dementia and the first brain-enriched miRNA is enriched in brain cortex. In one embodiment of any of the above methods, the neurodegenerative disorder is AD (dementia stages) and the first brain-enriched miRNA is neuronal body miRNA. In one embodiment of any of the above methods, the neurodegenerative disorder is AD dementia and the first brain-enriched miRNA is neuronal body miRNA.

In one embodiment of any of the above methods, the neurodegenerative disorder is an early stage of AD (MCI or pre-MCI) and the pair of the first miRNA and the second miRNA is selected from the group consisting of miR-323-3p/miR-127-3p, miR-323-3p/miR-433, miR134/miR-370, miR-335-5p/miR-7, miR-134/miR-410, miR-134/miR-127-3p, miR-335-5p/miR-9, miP-132/miR-451, miR-323-3p/miR-370; miR-132/miR-9, and miR-135a/miR-9. In one specific embodiment of any of the above methods, the neurodegenerative disease is an early stage of AD (MCI or pre-MCI) and the pair of the first miRNA and the second miRNA is selected from the group consisting of miR-323-

3p/miR-433, miR-335-5p/miR-7, miR-134/miR-410, miR-335-5p/miR-9, miP-132/miR-451, and miR-135a/miR-9.

In one embodiment of any of the above methods, the neurodegenerative disease is an early stage of AD (MCI or pre-MCI) and the method comprises measuring the level for one or more miRNA pair combinations selected from the group consisting of miR-323-3p/miR-433+miR-323-3p/miR-127-3p; miR-134/miR-127-3p+miR-323-3p/miR-433+miR-323-3p/miR-127-3p+miR-323-3p/miR-370; miR-134/miR-370+miR-323-3p/miR-433+miR-323-3p/miR-127+miR-323-3p/370; miR-323-3p/370+miR-323-3p/miR-433+miR-134/miR-370+miR-335-5p/miR-9; miR-132/miR-9+miP-132/miR-451+miR-335-5p/miR-7; miR-132/miR-9+miR-135a/miR-9+miR-335-5p/miR-7; miR-134/miR-410+miR-323-3p/miR-127-3p; and miR-134/miR-410+miR-323-3p/miR-127-3p.

In one aspect, the invention provides a method for detecting a Mild Cognitive Impairment (MCI) or pre-MCI in a subject, which method comprises:
a) measuring the level of a first miRNA, wherein said first miRNA is selected from the group consisting of miR-132, miR-134, miR-135a, miR-323-3p, miR-335-5p, miR-382, and miR-411;
b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;
c) optionally calculating the ratio of the levels of the miRNAs measured in steps (a) and (b);
d) optionally comparing the ratio of the levels of the miRNAs calculated in step (c) with a corresponding control ratio, and
e) optionally (i) identifying the subject as being afflicted with MCI or pre-MCI when the ratio of the levels of the miRNAs calculated in step (c) is higher than the corresponding control ratio or (ii) identifying the subject as not being afflicted with MCI or pre-MCI when the ratio of the levels of the miRNA calculated in step (c) is not higher than the corresponding control ratio.

The invention also provides a method for detecting Mild Cognitive Impairment (MCI) or pre-MCI in a subject, which method comprises:
a. measuring the level of a first miRNA, wherein said first miRNA is selected from the group consisting of miR-132, miR-134, miR-135a, miR-323-3p, miR-335-5p, miR-382, and miR-411;
b. measuring the level of a second miRNA in the same bodily fluid sample collected from the subject, wherein said second miRNA is selected from the group consisting of miR-127-3p, miR-370, miR-410, miR-433, miR-7, miR-451, and miR-9;
c. calculating the ratio of the levels of the miRNAs measured in steps (a) and (b);
d. comparing the ratio of the levels of the miRNAs calculated in step (c) with a corresponding control ratio;
e. (i) identifying the subject as being afflicted with MCI or pre-MCI when the ratio of the levels of the miRNAs calculated in step (c) is higher than the corresponding control ratio or (ii) identifying the subject as not being afflicted with AD when the ratio of the levels of the miRNA calculated in step (c) is not higher than the corresponding control ratio.

In one embodiment, step (c) comprises:
(1) calculating using a suitably programmed processor, the ratio of the levels of the miRNAs measured in steps (a) and (b);

(2) calculating, by the processor and based on the ratio determined in step (c), a first probability based on a first predefined probability distribution curve, wherein the first predefined probability distribution curve corresponds to MCI or pre-MCI;
(3) calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;
step (d) comprises determining, by the processor, a difference between the first probability calculated in step (c)(1) and the second probability calculated in step (c)(2), and
step (e) comprises (i) identifying, by the processor, the subject as being afflicted with MCI or pre-MCI when the difference between the first probability and the second probability calculated in step (f) is positive or (ii) identifying the subject as not being afflicted with the MCI or pre-MCI when the difference between the first probability and the second probability calculated in step (d) is negative.

In another aspect, the invention provides a method for treating Mild Cognitive Impairment (MCI) or pre-MCI in a subject in need thereof, which method comprises:
a) measuring the level of a first miRNA, wherein said first miRNA is selected from the group consisting of miR-132, miR-134, miR-135a, miR-323-3p, miR-335-5p, miR-382, and miR-411;
b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;
c) optionally calculating the ratio of the levels of the miRNAs measured in steps (a) and (b);
d) optionally comparing the ratio of the levels of the miRNAs calculated in step (c) with a corresponding control ratio;
e) optionally (i) identifying the subject as being afflicted with MCI or pre-MCI when the ratio of the levels of the miRNAs calculated in step (c) is higher than the corresponding control ratio or (ii) identifying the subject as not being afflicted with MCI or pre-MCI when the ratio of the levels of the miRNA calculated in step (c) is not higher than the corresponding control ratio, and
f) administering a therapeutic or preventive treatment to the subject.

In another aspect, the invention provides a method for treating Mild Cognitive Impairment (MCI) or pre-MCI in a subject in need thereof, which method comprises:
a) measuring the level of a first miRNA, wherein said first miRNA is selected from the group consisting of miR-132, miR-134, miR-135a, miR-323-3p, miR-335-5p, miR-382, and miR-411;
b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;
c) calculating the ratio of the levels of the miRNAs measured in steps (a) and (b);
d) comparing the ratio of the levels of the miRNAs calculated in step (c) with a corresponding control ratio;
e) (i) identifying the subject as being afflicted with MCI or pre-MCI when the ratio of the levels of the miRNAs calculated in step (c) is higher than the corresponding control ratio or (ii) identifying the subject as not being afflicted with MCI or pre-MCI when the ratio of the levels of the miRNA calculated in step (c) is not higher than the corresponding control ratio, and f) administering a therapeutic or preventive treatment to the subject.

In yet another aspect, the invention provides a method for selecting subjects for enrollment in a clinical trial involving treatment of Mild Cognitive Impairment (MCI) or pre-MCI, which method comprises:

a) measuring the level of a first miRNA, wherein said first miRNA is selected from the group consisting of miR-132, miR-134, miR-135a, miR-323-3p, miR-335-5p, miR-382, and miR-411;

b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with MCI or pre-MCI when the ratio of the levels of the miRNAs calculated in step (c) is higher than the corresponding control ratio or (ii) identifying the subject as not being afflicted with MCI or pre-MCI when the ratio of the levels of the miRNA calculated in step (c) is not higher than the corresponding control ratio, and f) recruiting the subject in a clinical trial.

In yet another aspect, the invention provides a method for selecting subjects for enrollment in a clinical trial involving treatment of Mild Cognitive Impairment (MCI) or pre-MCI, which method comprises:

a) measuring the level of a first miRNA, wherein said first miRNA is selected from the group consisting of miR-132, miR-134, miR-135a, miR-323-3p, miR-335-5p, miR-382, and miR-411;

b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;

c) calculating the ratio of the levels of the miRNAs measured in steps (a) and (b);

d) comparing the ratio of the levels of the miRNAs calculated in step (c) with a corresponding control ratio;

e) (i) identifying the subject as being afflicted with MCI or pre-MCI when the ratio of the levels of the miRNAs calculated in step (c) is higher than the corresponding control ratio or (ii) identifying the subject as not being afflicted with MCI or pre-MCI when the ratio of the levels of the miRNA calculated in step (c) is not higher than the corresponding control ratio, and f) recruiting the subject in a clinical trial.

In another aspect, the invention provides a method for monitoring changes in development of Mild Cognitive Impairment (MCI) or pre-MCI in a subject (e.g., a subject who had been previously diagnosed with MCI or pre-MCI), which method comprises:

a) measuring the level of a first miRNA in two or more bodily fluid samples collected from the subject, wherein said first miRNA is selected from the group consisting of miR-132, miR-134, miR-135a, miR-323-3p, miR-335-5p, miR-382, and miR-411;

b) measuring the level of a second miRNA in the same bodily fluid samples collected from the subject, wherein said second miRNA is selected from the group consisting of miR-127-3p, miR-370, miR-410, miR-433, miR-7, miR-451, and miR-9;

c) optionally calculating the ratio of the levels of the miRNA measured in steps (a) and (b) for each bodily fluid sample;

d) optionally comparing the ratios of the levels of the miRNA calculated in step (c) between the earlier collected and later collected bodily fluid sample(s), and e) optionally (i) determining that MCI or pre-MCI in the subject has progressed if the ratio of the levels of the miRNA calculated in step (c) is increased in the later collected bodily fluid sample(s) as compared to the earlier collected sample(s), or (ii) determining that MCI or pre-MCI in the subject has not progressed if the ratio of the levels of the miRNA calculated in step (c) is not changed in the later collected bodily fluid sample(s) as compared to the earlier collected sample(s).

In another aspect, the invention provides a method for monitoring changes in development of Mild Cognitive Impairment (MCI) or pre-MCI in a subject (e.g., a subject who had been previously diagnosed with MCI or pre-MCI), which method comprises:

a) measuring the level of a first miRNA in two or more bodily fluid samples collected from the subject, wherein said first miRNA is selected from the group consisting of miR-132, miR-134, miR-135a, miR-323-3p, miR-335-5p, miR-382, and miR-411;

b) measuring the level of a second miRNA in the same bodily fluid samples collected from the subject, wherein said second miRNA is selected from the group consisting of miR-127-3p, miR-370, miR-410, miR-433, miR-7, miR-451, and miR-9;

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that MCI or pre-MCI in the subject has progressed if the ratio of the levels of the miRNA calculated in step (c) is increased in the later collected bodily fluid sample(s) as compared to the earlier collected sample(s), or (ii) determining that MCI or pre-MCI in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of Mild Cognitive Impairment (MCI) or pre-MCI in a subject (e.g., a subject who had been previously diagnosed with MCI or pre-MCI), which method comprises:

a) measuring the level of a first miRNA in a bodily fluid sample collected from the subject prior to initiation of the treatment, wherein said first miRNA is selected from the group consisting of miR-132, miR-134, miR-135a, miR-323-3p, miR-335-5p, miR-382, and miR-411;

b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;

c) optionally calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);
f) optionally calculating the ratio of the levels of the miRNA measured in steps (d) and (e) for each bodily fluid sample;
g) optionally comparing the ratios of the levels of the miRNA calculated in steps (c) and (f), and optionally comparing the ratios of the levels of the miRNA calculated in step (f) between different samples in step (d), and
h) optionally (i) determining that the treatment is effective for MCI or pre-MCI if the ratio of the levels of the miRNA calculated in step (c) is higher than the corresponding ratio(s) calculated in step (f), or (ii) determining that the treatment is not effective for MCI or pre-MCI if the ratio of the levels of the miRNA calculated in step (c) is not higher than the corresponding ratio(s) calculated in step (f).

In a separate aspect, the invention provides a method for identifying a compound useful for slowing down the progression or treating Mild Cognitive Impairment (MCI) or pre-MCI or Alzheimer's disease (AD) in a subject (a subject who had been previously diagnosed with MCI or pre-MCI), which method comprises:
a) measuring the level of a first miRNA in a bodily fluid sample collected from the subject prior to test compound administration, wherein said first miRNA is selected from the group consisting of miR-132, miR-134, miR-135a, miR-323-3p, miR-335-5p, miR-382, and miR-411;
b) measuring the level of a second miRNA in the same bodily fluid sample collected from the subject, wherein said second miRNA is selected from the group consisting of miR-127-3p, miR-370, miR-410, miR-433, miR-7, miR-451, and miR-9;
c) optionally calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) optionally calculating the ratio of the levels of the miR-NAs measured in steps (d) and (e) for each of the bodily fluid samples collected from the subject following administration of the test compound;
g) optionally comparing the ratio of the levels of the miRNA calculated in steps (c) and (f), and
h) optionally (i) identifying that the test compound is useful for slowing down the progression or treating MCI or pre-MCI or AD if the ratio of the levels of the miRNA calculated in step (f) is lower than the ratio of the levels of the miRNA calculated in step (c); (ii) identifying that the test compound is not useful for slowing down the progression or treating MCI or pre-MCI or AD if the ratio of the levels of the miRNA calculated in step (f) is not lower than the ratio of the levels of the miRNAs calculated in step (c).

In one embodiment of any of the above methods related to MCI and pre-MCI, the first miRNA is miR-135a or miR-335-5p. In one embodiment of any of the above methods related to MCI and pre-MCI, the second miRNA is selected from the group consisting of miR-7, miR-410, miR-433, and miR-451.

In one embodiment of any of the above methods related to MCI and pre-MCI, the pair of the first miRNA and the second miRNA is selected from the group consisting of miR-323-3p/miR-127-3p, miR-323-3p/miR-433, miR134/miR-370, miR-335-5p/miR-7, miR-134/miR-410, miR-134/miR-127-3p, miR-335-5p/miR-9, miP-132/miR-451, miR-323-3p/miR-370; miR-132/miR-9, and miR-135a/miR-9.

In another embodiment of any of the above methods related to MCI and pre-MCI, the pair of the first miRNA and the second miRNA is selected from the group consisting of miR-323-3p/miR-433, miR-335-5p/miR-7, miR-134/miR-410, miR-335-5p/miR-9, miP-132/miR-451, and miR-135a/miR-9.

In one embodiment of any of the above methods related to MCI and pre-MCI, the method comprises measuring the level for one or more miRNA pair combinations selected from the group consisting of miR-323-3p/miR-433+miR-323-3p/miR-127-3p; miR-134/miR-127-3p+miR-323-3p/miR-433+miR-323-3p/miR-127-3p+miR-323-3p/miR-370; miR-134/miR-370+miR-323-3p/miR-433+miR-323-3p/miR-127+miR-323-3p/370; miR-323-3p/370+miR-323-3p/miR-433+miR-134/miR-370+miR-335-5p/miR-9; miR-132/miR-9+miP-132/miR-451+miR-335-5p/miR-7; miR-132/miR-9+miR-135a/miR-9+miR-335-5p/miR-7; miR-134/miR-410+miR-323-3p/miR-127-3p; and miR-134/miR-410+miR-323-3p/miR-127-3p.

In one aspect, the invention provides a method for detecting Alzheimer's disease (AD) dementia in a subject, which method comprises:
a) measuring the level of a first miRNA in a bodily fluid sample collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;
b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;
c) optionally calculating the ratio of the levels of the miRNAs measured in steps (a) and (b);
d) optionally comparing the ratio of the levels of the miRNAs calculated in step (c) with a corresponding control ratio, and
e) optionally (i) identifying the subject as being afflicted with AD when the ratio of the levels of the miRNAs calculated in step (c) is higher than the corresponding control ratio or (ii) identifying the subject as not being afflicted with AD when the ratio of the levels of the miRNA calculated in step (c) is not higher than the corresponding control ratio.

In one embodiment, step (c) comprises
(1) calculating using a suitably programmed processor, the ratio of the levels of the miRNAs measured in steps (a) and (b);
(2) calculating, by the processor and based on the ratio determined in step (c)(1), a first probability based on a first predefined probability distribution curve, wherein the first predefined probability distribution curve corresponds to the neurodegenerative disorder;
(3) calculating, by the processor and based on the ratio determined in step (c)(2), a second probability based on a second predefined probability distribution curve, wherein the second predefined probability distribution curve corresponds to a matched control or another pathology;
step (d) comprises determining, by the processor, a difference between the first probability calculated in step (c)(2) and the second probability calculated in step (c)(3), and
step (e) comprises (i) identifying, by the processor, the subject as being afflicted with AD when the difference between the first probability and the second probability calculated in step (d) is positive or (ii) identifying the subject as not being afflicted with AD when the difference between the first probability and the second probability calculated in step (d) is negative.

The invention also provides a computer-implemented method of assigning a subject into a category of being afflicted with Alzheimer's disease (AD), which method comprises:

a. measuring the level of a first miRNA in a bodily fluid sample collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b. measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c. calculating using a suitably programmed processor, the ratio of the levels of the miRNAs measured in steps (a) and (b);

d. calculating, by the processor and based on the ratio determined in step (c), a first probability based on a first predefined probability distribution curve, wherein the first predefined probability distribution curve corresponds to the neurodegenerative disorder;

e. calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;

f. determining, by the processor, a difference between the first probability calculated in step (d) and the second probability calculated in step (e), and g. (i) identifying, by the processor, the subject as being afflicted with AD when the difference between the first probability and the second probability calculated in step (f) is positive or (ii) identifying the subject as not being afflicted with AD when the difference between the first probability and the second probability calculated in step (f) is negative.

In another aspect, the invention provides a method for treating Alzheimer's disease (AD) in a subject in need thereof, which method comprises:

a) measuring the level of a first miRNA in a bodily fluid sample collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with AD when the ratio of the levels of the miRNAs calculated in step (c) is higher than the corresponding control ratio or (ii) identifying the subject as not being afflicted with AD when the ratio of the levels of the miRNA calculated in step (c) is not higher than the corresponding control ratio, and f) administering a therapeutic or preventive treatment to the subject.

In another aspect, the invention provides a method for treating Alzheimer's disease (AD) in a subject in need thereof, which method comprises:

a) measuring the level of a first miRNA in a bodily fluid sample collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c) calculating the ratio of the levels of the miRNAs measured in steps (a) and (b);

d) comparing the ratio of the levels of the miRNAs calculated in step (c) with a corresponding control ratio;

e) (i) identifying the subject as being afflicted with AD when the ratio of the levels of the miRNAs calculated in step (c) is higher than the corresponding control ratio or (ii) identifying the subject as not being afflicted with AD when the ratio of the levels of the miRNA calculated in step (c) is not higher than the corresponding control ratio, and f) administering a therapeutic or preventive treatment to the subject.

In yet another aspect, the invention provides a method for selecting subjects for enrollment in a clinical trial involving treatment of Alzheimer's disease (AD), which method comprises:

a) measuring the level of a first miRNA in a bodily fluid sample collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with AD when the ratio of the levels of the miRNAs calculated in step (c) is higher than the corresponding control ratio or (ii) identifying the subject as not being afflicted with AD when the ratio of the levels of the miRNA calculated in step (c) is not higher than the corresponding control ratio, and f) recruiting the subject in a clinical trial.

In another aspect, the invention provides a method for monitoring changes in development of Alzheimer's disease (AD) in a subject (e.g., a subject who had been previously diagnosed with AD), which method comprises:

a) measuring the level of a first miRNA in two or more bodily fluid samples collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid samples collected from the subject, wherein said second miRNA is selected from the group consisting of let-7e, miR-128a, miR-146a, miR-16, miR-181a, miR-29a, miR-411, miR-874, and miR-451;

c) optionally calculating the ratio of the levels of the miRNA measured in steps (a) and (b) for each bodily fluid sample;

d) optionally comparing the ratios of the levels of the miRNA calculated in step (c) between the earlier collected and later collected bodily fluid sample(s), and e) optionally (i) determining that AD in the subject has progressed if the ratio of the levels of the miRNA calculated in step (c) is increased in the later collected bodily fluid sample(s) as compared to the earlier collected sample(s), or (ii) determining that AD in the subject has not progressed if the ratio of the levels of the miRNA calculated in step (c) is not changed in the later collected bodily fluid sample(s) as compared to the earlier collected sample(s).

In another aspect, the invention provides a method for monitoring changes in development of Alzheimer's disease (AD) in a subject (e.g., a subject who had been previously diagnosed with AD), which method comprises:

a) measuring the level of a first miRNA in two or more bodily fluid samples collected from the subject, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid samples collected from the subject, wherein said second miRNA is selected from the group consisting of let-7e, miR-128a, miR-146a, miR-16, miR-181a, miR-29a, miR-411, miR-874, and miR-451;

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that AD in the subject has progressed if the ratio of the levels of the miRNA calculated in step (c) is increased in the later collected bodily fluid sample(s) as compared to the earlier collected sample(s), or (ii) determining that AD in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of Alzheimer's disease (AD) in a subject (e.g., a subject who had been previously diagnosed with AD), which method comprises:

a) measuring the level of a first miRNA in a bodily fluid sample collected from the subject prior to initiation of the treatment, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c) optionally calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) optionally calculating the ratio of the levels of the miRNA measured in steps (d) and (e) for each bodily fluid sample;

g) optionally comparing the ratios of the levels of the miRNA calculated in steps (c) and (f), and optionally comparing the ratios of the levels of the miRNA calculated in step (f) between different samples in step (d), and h) optionally (i) determining that the treatment is effective for AD if the ratio of the levels of the miRNA calculated in step (c) is higher than the corresponding ratio(s) calculated in step (f), or (ii) determining that the treatment is not effective for AD if the ratio of the levels of the miRNA calculated in step (c) is not higher than the corresponding ratio(s) calculated in step (f).

In a separate aspect, the invention provides a method for identifying a compound useful for slowing down the progression or treating Alzheimer's disease (AD) in a subject (a subject who had been previously diagnosed with AD), which method comprises:

a) measuring the level of a first miRNA in a bodily fluid sample collected from the subject prior to test compound administration, wherein said first miRNA is selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491;

b) measuring the level of a second miRNA in the same bodily fluid sample collected from the subject, wherein said second miRNA is selected from the group consisting of let-7e, miR-128a, miR-146a, miR-16, miR-181a, miR-29a, miR-411, miR-874, and miR-451;

c) optionally calculating the ratio of the levels of the miRNA measured in steps (a) and (b);

d) measuring the level of the same first miRNA as in step (a) in one or more bodily fluid samples collected from the subject following administration of a test compound;

e) measuring the level of the same second miRNA as in step (b) in the same bodily fluid sample(s) as in step (d);

f) optionally calculating the ratio of the levels of the miRNAs measured in steps (d) and (e) for each of the bodily fluid samples collected from the subject following administration of the test compound;

g) optionally comparing the ratio of the levels of the miRNA calculated in steps (c) and (f), and h) optionally (i) identifying that the test compound is useful for slowing down the progression or treating AD if the ratio of the levels of the miRNA calculated in step (f) is lower than the ratio of the levels of the miRNA calculated in step (c); (ii) identifying that the test compound is not useful for slowing down the progression or treating AD if the ratio of the levels of the miRNA calculated in step (f) is not lower than the ratio of the levels of the miRNAs calculated in step (c).

In one embodiment of any of the above methods related to AD, the pair of the first miRNA and the second miRNA is selected from the group consisting of miR-329/miR-181a, miR-99b/miR-181a, miR-99b/let-7e, miR-107/miR-146a, miR-9*/miR-874, miR-7/miR-16, miR-329/miR-874, miR-329/let-7e, miR-329/miR-146a, miR-433/miR-181a, miR-107/miR-181a, miR-99b/miR-874, miR-7/miR-874, miR-125b/miR-874, miR-107/let-7e, miR-7/miR-451, miR-204/miR-874, miR-491/let-7e, miR-29a/miR-874, miR-323-3p/ let-7e, miR-382/let-7e, miR-127/miR-411, miR-335-5p/miR-181a, miR-9*/miR-146a, miR-128a/miR-181a, and miR-128a/miR-146a.

In one embodiment of any of the above methods related to AD, the method comprises measuring the level for one or more miRNA pair combinations selected from the group consisting of miR-107/miR-146a+miR-9*/miR-155, miR-99b/miR-874+miR-9*/miR-155, miR-9*/miR-16+miR-7/miR-874, miR-329/miR-181a+miR-9*/miR-16+miR-7/miR-874, miR-107/miR-181a+miR-9*/miR-16+miR-7/miR-874, miR-107/miR-146a+miR-9*/miR-16+miR-7/miR-874, miR-99b/miR-181a+miR-9*/miR-874+miR-7/miR-16, and miR-7/miR-451+miR-204/miR-874+miR-491/let-7e.

In one embodiment of any of the above methods related to AD, the subject is a male, and the method comprises measuring the level for one or more miRNA pair combinations selected from the group consisting of miR-132/miR-433+miR-132/miR-7+miR-874/miR-9, miR-323/miR-485+miR-410/miR-485, and miR-99b/miR-181a+miR-125/miR-874+miR-9*+miR-29a.

In one embodiment of any of the above methods related to AD, the subject is a female, and the method comprises measuring the level for one or more miRNA pair combinations selected from the group consisting of miR-135a/miR-433+miR-323/miR-433+miR-323/miR-127, miR-323/miR-433+miR-323/miR-411+miR-128a/miR-7, and miR-99b/miR-181a+miR-9*/miR-874+miR-7/miR-451.

In one aspect, the invention provides a method for detecting Parkinson's disease (PD) in a subject, which method comprises:
a) measuring the level of a first miRNA in a bodily fluid sample collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;
b) measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;
c) optionally calculating the ratio of the levels of the miRNAs measured in steps (a) and (b);
d) optionally comparing the ratio of the levels of the miRNAs calculated in step (c) with a corresponding control ratio, and
e) optionally (i) identifying the subject as being afflicted with PD when the ratio of the levels of the miRNAs calculated in step (c) is higher than the corresponding control ratio or (ii) identifying the subject as not being afflicted with PD when the ratio of the levels of the miRNA calculated in step (c) is not higher than the corresponding control ratio.

In one embodiment, step (c) comprises
(1) calculating using a suitably programmed processor, the ratio of the levels of the miRNAs measured in steps (a) and (b);
(2) calculating, by the processor and based on the ratio determined in step (c)(1), a first probability based on a first predefined probability distribution curve, wherein the first predefined probability distribution curve corresponds to the neurodegenerative disorder;
(3) calculating, by the processor and based on the ratio determined in step (c)(1), a second probability based on a second predefined probability distribution curve, wherein the second predefined probability distribution curve corresponds to a matched control or another pathology;
step (d) comprises determining, by the processor, a difference between the first probability calculated in step (c)(2) and the second probability calculated in step (c)(3); and
step (e) comprises (i) identifying, by the processor, the subject as being afflicted with PD when the difference between the first probability and the second probability calculated in step (d) is positive or (ii) identifying the subject as not being afflicted with PD when the difference between the first probability and the second probability calculated in step (d) is negative.

In one aspect, the invention provides a method for detecting Parkinson's disease (PD) in a subject, which method comprises:
a) measuring the level of a first miRNA in a bodily fluid sample collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;
b) measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;
c) calculating the ratio of the levels of the miRNAs measured in steps (a) and (b);
d) comparing the ratio of the levels of the miRNAs calculated in step (c) with a corresponding control ratio, and
e) (i) identifying the subject as being afflicted with PD when the ratio of the levels of the miRNAs calculated in step (c) is higher than the corresponding control ratio or (ii) identifying the subject as not being afflicted with PD when the ratio of the levels of the miRNA calculated in step (c) is not higher than the corresponding control ratio.

The invention also provides a computer-implemented method of assigning a subject into a category of being afflicted with Parkinson's disease (PD), which method comprises:
a. measuring the level of a first miRNA in a bodily fluid sample collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;
b. measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;
c. calculating using a suitably programmed processor, the ratio of the levels of the miRNAs measured in steps (a) and (b);
d. calculating, by the processor and based on the ratio determined in step (c), a first probability based on a first predefined probability distribution curve, wherein the first predefined probability distribution curve corresponds to the neurodegenerative disorder;
e. calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;

f. determining, by the processor, a difference between the first probability calculated in step (d) and the second probability calculated in step (e), and g. (i) identifying, by the processor, the subject as being afflicted with PD when the difference between the first probability and the second probability calculated in step (f) is positive or (ii) identifying the subject as not being afflicted with PD when the difference between the first probability and the second probability calculated in step (f) is negative.

In another aspect, the invention provides a method for treating Parkinson's disease (PD) in a subject in need thereof, which method comprises:

a) measuring the level of a first miRNA in a bodily fluid sample collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;

b) measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with PD when the ratio of the levels of the miRNAs calculated in step (c) is higher than the corresponding control ratio or (ii) identifying the subject as not being afflicted with PD when the ratio of the levels of the miRNA calculated in step (c) is not higher than the corresponding control ratio, and f) administering a therapeutic or preventive treatment to the subject.

In yet another aspect, the invention provides a method for selecting subjects for enrollment in a clinical trial involving treatment of Parkinson's disease (PD), which method comprises:

a) measuring the level of a first miRNA in a bodily fluid sample collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;

b) measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with PD when the ratio of the levels of the miRNAs calculated in step (c) is higher than the corresponding control ratio or (ii) identifying the subject as not being afflicted with PD when the ratio of the levels of the miRNA calculated in step (c) is not higher than the corresponding control ratio, and f) recruiting the subject in a clinical trial.

In another aspect, the invention provides a method for monitoring changes in development of Parkinson's disease (PD) in a subject (e.g., a subject who had been previously diagnosed with PD), which method comprises:

a) measuring the level of a first miRNA in two or more bodily fluid samples collected from the subject, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;

b) measuring the level of a second miRNA in the same bodily fluid samples collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;

f) optionally calculating the ratio of the levels of the miRNA measured in steps (a) and (b) for each bodily fluid sample;

g) optionally comparing the ratios of the levels of the miRNA calculated in step (c) between the earlier collected and later collected bodily fluid sample(s), and h) optionally (i) determining that PD in the subject has progressed if the ratio of the levels of the miRNA calculated in step (c) is increased in the later collected bodily fluid sample(s) as compared to the earlier collected sample(s), or (ii) determining that PD in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of Parkinson's disease (PD) in a subject (e.g., a subject who had been previously diagnosed with PD), which method comprises:

a. measuring the level of a first miRNA in a bodily fluid sample collected from the subject prior to initiation of the treatment, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;

b. measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;

c. optionally calculating the ratio of the levels of the miRNA measured in steps (a) and (b);

d. measuring the level of the same first miRNA as in step (a) in one or more bodily fluid sample(s) collected from the subject in the course of or following the treatment;

e. measuring the level of the same second miRNA as in step (b) in the same bodily fluid sample(s) as in step (d);

f. optionally calculating the ratio of the levels of the miRNA measured in steps (d) and (e) for each bodily fluid sample;

g. optionally comparing the ratios of the levels of the miRNA calculated in steps (c) and (f), and optionally comparing the ratios of the levels of the miRNA calculated in step (f) between different samples in step (d), and h. optionally (i) determining that the treatment is effective for PD if the ratio of the levels of the miRNA calculated in step (c) is higher than the corresponding ratio(s) calculated in step (f), or (ii) determining that the treatment is not effective for PD if the ratio of the levels of the miRNA calculated in step (c) is not higher than the corresponding ratio(s) calculated in step (f).

In a separate aspect, the invention provides a method for identifying a compound useful for slowing down the progression or treating Parkinson's disease (PD) in a subject (a subject who had been previously diagnosed with PD), which method comprises:

a) measuring the level of a first miRNA in a bodily fluid sample collected from the subject prior to test compound administration, wherein said first miRNA is selected from the group consisting of miR-7, let-7e, miR-127, miR-128a, miR-155, miR-181a, miR-323-3p, miR-335-5p, miR-9*, miR-99b, miR-491, and miR-495;

b) measuring the level of a second miRNA in the same bodily fluid sample collected from the subject, wherein said second miRNA is selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132;

c) optionally calculating the ratio of the levels of the miRNA measured in steps (a) and (b);

d) measuring the level of the same first miRNA as in step (a) in one or more bodily fluid samples collected from the subject following administration of a test compound;

e) measuring the level of the same second miRNA as in step (b) in the same bodily fluid sample(s) as in step (d);

f) optionally calculating the ratio of the levels of the miRNAs measured in steps (d) and (e) for each of the bodily fluid samples collected from the subject following administration of the test compound;

g) optionally comparing the ratio of the levels of the miRNA calculated in steps (c) and (f), and h) optionally (i) identifying that the test compound is useful for slowing down the progression or treating PD if the ratio of the levels of the miRNA calculated in step (f) is lower than the ratio of the levels of the miRNA calculated in step (c); (ii) identifying that the test compound is not useful for slowing down the progression or treating PD if the ratio of the levels of the miRNA calculated in step (f) is not lower than the ratio of the levels of the miRNAs calculated in step (c).

In one embodiment of any of the above methods related to PD, the pair of the first miRNA and the second miRNA is selected from the group consisting of miR-9*/miR-31, miR-9*/miR-138, miR-9*/miR-218, miR-9*/miR-129-3p, miR-9*/miR-874, miR-9*/miR-204, miR-9*/miR-29a, miR-99b/miR-31, miR-99b/miR-138, miR-99b/miR-218, miR-99b/miR-129-3p, miR-99b/miR-874, miR-99b/miR-125b, miR-99b/miR-204, miR-99b/miR-338-3p, miR-99b/miR-29a, miR-99b/let-7e, miR-99b/miR-9, miR-99b/miR-146a, miR-127/miR-411, miR-491/miR-138, miR-128a/miR-138, miR-128a/miR-874, miR-335-5p/miR-138, miR-181a/miR-874, miR-155/miR-31, miR-155/miR-874, let-7e/miR-31, let-7e/miR-874, miR-491/miR-138, miR-491/miR-204, miR-491/miR-31, miR-491/miR-874, miR-7/miR-129-3p, miR-7/miR-874, miR-127/miR-382, miR-495/miR-382, miR-323-3p/miR-411, miR-9*/miR-132, and miR-99b/miR-132.

In one embodiment of any of the above methods related to PD, the method comprises measuring the level for one or more miRNA pair combinations selected from the group consisting of miR-9*/miR-31+miR-99b/miR-874, miR-99b/miR-874+miR-127/miR-411, miR-491/miR-874+miR-7/miR-129-3p, miR-127/miR-382+miR-128a/let-7e, miR-9*/miR-874+miR-99b/miR-874+miR-127/miR-411, miR-9*/miR-31+miR-99b/miR-874+miR-127/miR-411, miR-9*/miR-129-3p+miR-127/miR-411+miR-491/miR-138, miR-9*/miR-129-3p+miR-99b/miR-874+miR-127/miR-411, and miR-9*/miR-874+miR-127/miR-411+miR-128a/miR-138.

In one embodiment of any of the above methods related to PD, the subject is a male, and the method comprises measuring the level for an miRNA pair combination of miR-9*/miR-129-3p+miR-99b/miR-146a+miR-9*/miR-204.

In one embodiment of any of the above methods related to PD, the subject is a female, and the method comprises measuring the level for an miRNA pair combination of miR-9*/miR-29a+miR-99b/miR-874+miR-491/let-7e.

In one aspect, the invention provides a method for detecting frontotemporal dementia (FTD) in a subject, which method comprises:

a) measuring the level of a first miRNA in a bodily fluid sample collected from the subject, wherein said first miRNA is selected from the group consisting of miR-7, miR-128a, miR-323-3p, miR-335-5p, miR-338-3p, miR-9*, miR-99b, and miR-491;

b) measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;

c) optionally calculating the ratio of the levels of the miRNAs measured in steps (a) and (b);

d) optionally comparing the ratio of the levels of the miRNAs calculated in step (c) with a corresponding control ratio, and e) optionally (i) identifying the subject as being afflicted with FTD when the ratio of the levels of the miRNAs calculated in step (c) is higher than the corresponding control ratio or (ii) identifying the subject as not being afflicted with FTD when the ratio of the levels of the miRNA calculated in step (c) is not higher than the corresponding control ratio.

In one embodiment, step (c) comprises
(1) calculating using a suitably programmed processor, the ratio of the levels of the miRNAs measured in steps (a) and (b);
(2) calculating, by the processor and based on the ratio determined in step (c)(1), a first probability based on a first predefined probability distribution curve, wherein the first predefined probability distribution curve corresponds to the neurodegenerative disorder;
(3) calculating, by the processor and based on the ratio determined in step (c)(1), a second probability based on a second predefined probability distribution curve, wherein the second predefined probability distribution curve corresponds to a matched control or another pathology;

step (d) comprises determining, by the processor, a difference between the first probability calculated in step (c)(2) and the second probability calculated in step (c)(3), and step (e) comprises (i) identifying, by the processor, the subject as being afflicted with FTD disorder when the difference between the first probability and the second probability calculated in step (d) is positive or (ii) identifying the subject as not being afflicted with FTD when the difference between the first probability and the second probability calculated in step (d) is negative.

The invention also provides a computer-implemented method of assigning a subject into a category of being afflicted with frontotemporal dementia (FTD), which method comprises:

a. measuring the level of a first miRNA in a bodily fluid sample collected from the subject, wherein said first miRNA is selected from the group consisting of miR-7, miR-128a, miR-323-3p, miR-335-5p, miR-338-3p, miR-9*, miR-99b, and miR-491;
b. measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;
c. calculating using a suitably programmed processor, the ratio of the levels of the miRNAs measured in steps (a) and (b);
d. calculating, by the processor and based on the ratio determined in step (c), a first probability based on a first predefined probability distribution curve, wherein the first predefined probability distribution curve corresponds to the neurodegenerative disorder;
e. calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;
f. determining, by the processor, a difference between the first probability calculated in step (d) and the second probability calculated in step (e), and
g. (i) identifying, by the processor, the subject as being afflicted with FTD when the difference between the first probability and the second probability calculated in step (f) is positive or (ii) identifying the subject as not being afflicted with FTD when the difference between the first probability and the second probability calculated in step (f) is negative.

In another aspect, the invention provides a method for treating frontotemporal dementia (FTD) in a subject in need thereof, which method comprises:
a) measuring the level of a first miRNA in a bodily fluid sample collected from the subject, wherein said first miRNA is selected from the group consisting of miR-7, miR-128a, miR-323-3p, miR-335-5p, miR-338-3p, miR-9*, miR-99b, and miR-491;
b) measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;
c) optionally calculating the ratio of the levels of the miRNAs measured in steps (a) and (b);
d) optionally comparing the ratio of the levels of the miRNAs calculated in step (c) with a corresponding control ratio;
e) optionally (i) identifying the subject as being afflicted with FTD when the ratio of the levels of the miRNAs calculated in step (c) is higher than the corresponding control ratio or (ii) identifying the subject as not being afflicted with FTD when the ratio of the levels of the miRNA calculated in step (c) is not higher than the corresponding control ratio, and
f) administering a therapeutic or preventive treatment to the subject.

In yet another aspect, the invention provides a method for selecting subjects for enrollment in a clinical trial involving treatment of frontotemporal dementia (FTD), which method comprises:
a) measuring the level of a first miRNA in a bodily fluid sample collected from the subject, wherein said first miRNA is selected from the group consisting of miR-7, miR-128a, miR-323-3p, miR-335-5p, miR-338-3p, miR-9*, miR-99b, and miR-491;
b) measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;
c) optionally calculating the ratio of the levels of the miRNAs measured in steps (a) and (b);
d) optionally comparing the ratio of the levels of the miRNAs calculated in step (c) with a corresponding control ratio;
e) optionally (i) identifying the subject as being afflicted with FTD when the ratio of the levels of the miRNAs calculated in step (c) is higher than the corresponding control ratio or (ii) identifying the subject as not being afflicted with FTD when the ratio of the levels of the miRNA calculated in step (c) is not higher than the corresponding control ratio, and
f) recruiting the subject in a clinical trial.

In another aspect, the invention provides a method for monitoring changes in development of frontotemporal dementia (FTD) in a subject (e.g., a subject who had been previously diagnosed with FTD), which method comprises:
a) measuring the level of a first miRNA in two or more bodily fluid samples collected from the subject, wherein said first miRNA is selected from the group consisting of miR-7, miR-128a, miR-323-3p, miR-335-5p, miR-338-3p, miR-9*, miR-99b, and miR-491;
b) measuring the level of a second miRNA in the same bodily fluid samples collected from the subject, wherein said second miRNA is selected from the group consisting of let-7e, miR-125b, miR-146a, miR-155, miR-181a, miR-31, miR-874, and miR-9;
c) optionally calculating the ratio of the levels of the miRNA measured in steps (a) and (b) for each bodily fluid sample;
d) optionally comparing the ratios of the levels of the miRNA calculated in step (c) between the earlier collected and later collected bodily fluid sample(s), and
e) optionally (i) determining that FTD in the subject has progressed if the ratio of the levels of the miRNA calculated in step (c) is increased in the later collected bodily fluid sample(s) as compared to the earlier collected sample(s), or (ii) determining that FTD in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of frontotemporal dementia (FTD) in a subject (e.g., a subject who had been previously diagnosed with FTD), which method comprises:
a. measuring the level of a first miRNA in a bodily fluid sample collected from the subject prior to initiation of the treatment, wherein said first miRNA is selected from the group consisting of miR-7, miR-128a, miR-323-3p, miR-335-5p, miR-338-3p, miR-9*, miR-99b, and miR-491;
b. measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;
c. optionally calculating the ratio of the levels of the miRNA measured in steps (a) and (b);
d. measuring the level of the same first miRNA as in step (a) in one or more bodily fluid sample(s) collected from the subject in the course of or following the treatment;
e. measuring the level of the same second miRNA as in step (b) in the same bodily fluid sample(s) as in step (d);

f. optionally calculating the ratio of the levels of the miRNA measured in steps (d) and (e) for each bodily fluid sample;
g. optionally comparing the ratios of the levels of the miRNA calculated in steps (c) and (f), and optionally comparing the ratios of the levels of the miRNA calculated in step (f) between different samples in step (d), and
h. optionally (i) determining that the treatment is effective for FTD if the ratio of the levels of the miRNA calculated in step (c) is higher than the corresponding ratio(s) calculated in step (f), or (ii) determining that the treatment is not effective for FTD if the ratio of the levels of the miRNA calculated in step (c) is not higher than the corresponding ratio(s) calculated in step (f).

In a separate aspect, the invention provides a method for identifying a compound useful for slowing down the progression or treating frontotemporal dementia (FTD) in a subject (a subject who had been previously diagnosed with FTD), which method comprises:
a) measuring the level of a first miRNA in a bodily fluid sample collected from the subject prior to test compound administration, wherein said first miRNA is selected from the group consisting of miR-7, miR-128a, miR-323-3p, miR-335-5p, miR-338-3p, miR-9*, miR-99b, and miR-491;
b) measuring the level of a second miRNA in the same bodily fluid sample collected from the subject, wherein said second miRNA is selected from the group consisting of let-7e, miR-125b, miR-146a, miR-155, miR-181a, miR-31, miR-874, and miR-9;
c) optionally calculating the ratio of the levels of the miRNA measured in steps (a) and (b);
d) measuring the level of the same first miRNA as in step (a) in one or more bodily fluid samples collected from the subject following administration of a test compound;
e) measuring the level of the same second miRNA as in step (b) in the same bodily fluid sample(s) as in step (d);
f) optionally calculating the ratio of the levels of the miRNAs measured in steps (d) and (e) for each of the bodily fluid samples collected from the subject following administration of the test compound;
g) optionally comparing the ratio of the levels of the miRNA calculated in steps (c) and (f), and
h) optionally (i) identifying that the test compound is useful for slowing down the progression or treating FTD if the ratio of the levels of the miRNA calculated in step (f) is lower than the ratio of the levels of the miRNA calculated in step (c); (ii) identifying that the test compound is not useful for slowing down the progression or treating FTD if the ratio of the levels of the miRNA calculated in step (f) is not lower than the ratio of the levels of the miRNAs calculated in step (c).

In one embodiment of any of the above methods related to FTD, the pair of the first miRNA and the second miRNA is selected from the group consisting of miR-9*/miR-181a, miR-9*/miR-874, miR-9*/miR-125b, miR-9*/let-7e, miR-9*/miR-155, miR-99b/miR-181a, miR-99b/let-7e, miR-335-5p/let-7e, miR-128a/miR-181a, miR-9*/miR-31, miR-9*/miR-146a, miR-9*/miR-9, miR-323-3p/miR-134, miR-338-3p/miR-181a, miR-491/let-7e, miR-128a/miR-874, miR-128a/let-7e, miR-7/miR-874, miR-7/miR-125b, miR-338-3p/let-7e, miR-335-5p/miR-181a, miR-335-5p/miR-9, and miR-335-5p/miR-146a.

In one embodiment of any of the above methods related to FTD, the method comprises measuring the level for one or more miRNA pair combinations selected from the group consisting of miR-9*/let-7e+miR-335-5p/let-7e, miR-9*/miR-155+miR-99b/let-7e, miR-7/miR-874+miR-128a/let-7e, miR-99b/let-7e+miR-335-5p/let-7e+miR-128a/miR-181a, miR-9*/let-7e+miR-128a/miR-874, miR-9*/let-7e+miR-7/miR-451+miR-335-5p/let-7e, miR-9*/let-7e+miR-335-5p/let-7e+miR-128a/miR-874, miR-9*/miR-9+miR-99b/let-7e+miR-335-5p/let-7e, and miR-335-5p/miR-181a+miR-335-5p/miR-146a+miR-335-5p/miR-9.

In one embodiment of any of the above methods related to FTD, the subject is a male, and the method comprises measuring the level for an miRNA pair combination of miR-335-5p/let-7e+miR-99b/let-7e+miR-9*/miR-181a.

In one embodiment of any of the above methods related to FTD, the subject is a female, and the method comprises measuring the level for an miRNA pair combination of miR-491/let-7e+miR-107/miR-9+miR-28/miR-181a.

In one aspect, the invention provides a method for detecting amyotrophic lateral sclerosis (ALS) in a subject, which method comprises:
a) measuring the level of a first miRNA in a bodily fluid sample collected from the subject, wherein said first miRNA is selected from the group consisting of miR-7, miR-181a, miR-206, miR-335-5p, miR-9*, and miR-99b;
b) measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;
c) optionally calculating the ratio of the levels of the miRNAs measured in steps (a) and (b);
d) optionally comparing the ratio of the levels of the miRNAs calculated in step (c) with a corresponding control ratio, and
e) optionally (i) identifying the subject as being afflicted with ALS when the ratio of the levels of the miRNAs calculated in step (c) is higher than the corresponding control ratio or (ii) identifying the subject as not being afflicted with ALS when the ratio of the levels of the miRNA calculated in step (c) is not higher than the corresponding control ratio.

In one embodiment, step (c) comprises
(1) calculating using a suitably programmed processor, the ratio of the levels of the miRNAs measured in steps (a) and (b);
(2) calculating, by the processor and based on the ratio determined in step (c)(1), a first probability based on a first predefined probability distribution curve, wherein the first predefined probability distribution curve corresponds to the neurodegenerative disorder;
(3) calculating, by the processor and based on the ratio determined in step (c)(1), a second probability based on a second predefined probability distribution curve, wherein the second predefined probability distribution curve corresponds to a matched control or another pathology;
step (d) comprises determining, by the processor, a difference between the first probability calculated in step (c)(2) and the second probability calculated in step (c)(3), and
step (e) comprises (i) identifying, by the processor, the subject as being afflicted with ALS when the difference between the first probability and the second probability calculated in step (d) is positive or (ii) identifying the subject as not being afflicted with ALS when the difference between the first probability and the second probability calculated in step (d) is negative.

The invention also provides a computer-implemented method of assigning a subject into a category of being afflicted with amyotrophic lateral sclerosis (ALS), which method comprises:

a. measuring the level of a first miRNA in a bodily fluid sample collected from the subject, wherein said first miRNA is selected from the group consisting of miR-7, miR-181a, miR-206, miR-335-5p, miR-9*, and miR-99b;

b. measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c. calculating using a suitably programmed processor, the ratio of the levels of the miRNAs measured in steps (a) and (b);

d. calculating, by the processor and based on the ratio determined in step (c), a first probability based on a first predefined probability distribution curve, wherein the first predefined probability distribution curve corresponds to the neurodegenerative disorder;

e. calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;

f. determining, by the processor, a difference between the first probability calculated in step (d) and the second probability calculated in step (e), and g. (i) identifying, by the processor, the subject as being afflicted with ALS when the difference between the first probability and the second probability calculated in step (f) is positive or (ii) identifying the subject as not being afflicted with ALS when the difference between the first probability and the second probability calculated in step (f) is negative.

In another aspect, the invention provides a method for treating amyotrophic lateral sclerosis (ALS) in a subject in need thereof, which method comprises:

a) measuring the level of a first miRNA in a bodily fluid sample collected from the subject, wherein said first miRNA is selected from the group consisting of miR-7, miR-181a, miR-206, miR-335-5p, miR-9*, and miR-99b;

b) measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with ALS when the ratio of the levels of the miRNAs calculated in step (c) is higher than the corresponding control ratio or (ii) identifying the subject as not being afflicted with ALS when the ratio of the levels of the miRNA calculated in step (c) is not higher than the corresponding control ratio, and f) administering a therapeutic or preventive treatment to the subject.

In yet another aspect, the invention provides a method for selecting subjects for enrollment in a clinical trial involving treatment of amyotrophic lateral sclerosis (ALS), which method comprises:

a) measuring the level of a first miRNA in a bodily fluid sample collected from the subject, wherein said first miRNA is selected from the group consisting of miR-7, miR-181a, miR-206, miR-335-5p, miR-9*, and miR-99b;

b) measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c) optionally calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with ALS when the ratio of the levels of the miRNAs calculated in step (c) is higher than the corresponding control ratio or (ii) identifying the subject as not being afflicted with ALS when the ratio of the levels of the miRNA calculated in step (c) is not higher than the corresponding control ratio, and f) recruiting the subject in a clinical trial.

In another aspect, the invention provides a method for monitoring changes in development of amyotrophic lateral sclerosis (ALS) in a subject (e.g., a subject who had been previously diagnosed with ALS), which method comprises:

a) measuring the level of a first miRNA in two or more bodily fluid samples collected from the subject, wherein said first miRNA is selected from the group consisting of miR-7, miR-181a, miR-206, miR-335-5p, miR-9*, and miR-99b;

b) measuring the level of a second miRNA in the same bodily fluid samples collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c) optionally calculating the ratio of the levels of the miRNA measured in steps (a) and (b) for each bodily fluid sample;

d) optionally comparing the ratios of the levels of the miRNA calculated in step (c) between the earlier collected and later collected bodily fluid sample(s), and e) optionally (i) determining that ALS in the subject has progressed if the ratio of the levels of the miRNA calculated in step (c) is increased in the later collected bodily fluid sample(s) as compared to the earlier collected sample(s), or (ii) determining that ALS in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of amyotrophic lateral sclerosis (ALS) in a subject (e.g., a subject who had been previously diagnosed with ALS), which method comprises:

a. measuring the level of a first miRNA in a bodily fluid sample collected from the subject prior to initiation of the treatment, wherein said first miRNA is selected from the group consisting of miR-7, miR-181a, miR-206, miR-335-5p, miR-9*, and miR-99b;

b. measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c. optionally calculating the ratio of the levels of the miRNA measured in steps (a) and (b);

d. measuring the level of the same first miRNA as in step (a) in one or more bodily fluid sample(s) collected from the subject in the course of or following the treatment;

e. measuring the level of the same second miRNA as in step (b) in the same bodily fluid sample(s) as in step (d);

f. optionally calculating the ratio of the levels of the miRNA measured in steps (d) and (e) for each bodily fluid sample;

g. optionally comparing the ratios of the levels of the miRNA calculated in steps (c) and (f), and optionally comparing the ratios of the levels of the miRNA calculated in step (f) between different samples in step (d), and h. optionally (i) determining that the treatment is effective for ALS if the ratio of the levels of the miRNA calculated in step (c) is higher than the corresponding ratio(s) calculated in step (f), or (ii) determining that the treatment is not effective for ALS if the ratio of the levels of the miRNA calculated in step (c) is not higher than the corresponding ratio(s) calculated in step (f).

In a separate aspect, the invention provides a method for identifying a compound useful for slowing down the progression or treating amyotrophic lateral sclerosis (ALS) in a subject (a subject who had been previously diagnosed with ALS), which method comprises:

a) measuring the level of a first miRNA in a bodily fluid sample collected from the subject prior to test compound administration, wherein said first miRNA is selected from the group consisting of miR-7, miR-181a, miR-206, miR-335-5p, miR-9*, and miR-99b;

b) measuring the level of a second miRNA in the same bodily fluid sample collected from the subject, wherein said second miRNA is selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451;

c) optionally calculating the ratio of the levels of the miRNA measured in steps (a) and (b);

d) measuring the level of the same first miRNA as in step (a) in one or more bodily fluid samples collected from the subject following administration of a test compound;

e) measuring the level of the same second miRNA as in step (b) in the same bodily fluid sample(s) as in step (d);

f) optionally calculating the ratio of the levels of the miRNAs measured in steps (d) and (e) for each of the bodily fluid samples collected from the subject following administration of the test compound;

g) optionally comparing the ratio of the levels of the miRNA calculated in steps (c) and (f), and h) optionally (i) identifying that the test compound is useful for slowing down the progression or treating ALS if the ratio of the levels of the miRNA calculated in step (f) is lower than the ratio of the levels of the miRNA calculated in step (c); (ii) identifying that the test compound is not useful for slowing down the progression or treating ALS if the ratio of the levels of the miRNA calculated in step (f) is not lower than the ratio of the levels of the miRNAs calculated in step (c).

In one embodiment of any of the above methods related to ALS, the pair of the first miRNA and the second miRNA is selected from the group consisting of miR-206/miR-31, miR-206/miR-129-3p, miR-206/miR-138, miR-206/miR-874, miR-206/miR-125b, miR-206/miR-204, miR-206/miR-29a, miR-206/miR-155, miR-206/miR-338-3p, miR-206/miR-16, miR-206/miR-451, miR-206/miR-218, miR-99b/miR-9, miR-99b/miR-155, miR-99b/miR-338-3p, miR-9*/miR-129-3p, miR-99b/miR-155, miR-99b/let-7e, miR-181a/miR-338-3p, miR-335-5p/miR-338-3p, miR-7/miR-31, miR-7/miR-129-3p, miR-9*/miR-129-3p, miR-9*/miR-338-3p, miR-99b/miR-338-3p, miR-99b/miR-128a, and miR-335-5p/let-7e.

In one embodiment of any of the above methods related to ALS, the method comprises measuring the level for one or more miRNA pair combinations selected from the group consisting of miR-206/miR-31+miR-99b/miR-338-3p, miR-206/miR-138+miR-9*/miR-129-3p, miR-206/miR-31+miR-335-5p/miR-338-3p, miR-206/miR-16+miR-335-5p/miR-338-3p, miR-9*/miR-129-3p+miR-99b/miR-338-3p, miR-206/miR-204+miR-206/miR-218+miR-335-5p/miR-338-3p, miR-206/miR-204+miR-206/miR-218+miR-9*/miR-129-3p, miR-206/miR-338-3p+miR-99b/miR-129-3p+miR-335-5p/miR-338-3p, miR-206/miR-338-3p+miR-99b/miR-155+miR-335-5p/miR-338-3p and miR-181a/miR-338-3p+miR-335-5p/miR-338-3p+miR-7/miR-31+miR-7/miR-129-3p.

In one embodiment of any of the above methods related to ALS, the subject is a male, and the method comprises measuring the level for an miRNA pair combination of miR-206/miR-155+miR-9*/miR-129-3p+miR-355/miR-338-3p.

In one embodiment of any of the above methods related to ALS, the subject is a female, and the method comprises measuring the level for an miRNA pair combination of miR-206/miR-7+miR-9*/miR-125b+miR-491/miR-204.

In one embodiment of any of the above methods, the method further comprises differentiation between the detected neurodegenerative disease ("first ND") and another neurodegenerative disease ("second ND"), which differentiation comprises:

a) measuring the level of a first miRNA in a bodily fluid sample collected from the subject (e.g., the same sample as used in the initial method or a separate sample), wherein said first miRNA is enriched in a brain area which is more substantially affected by the first ND than by the second ND;

b) measuring the level of a second miRNA in the same bodily fluid sample collected from the subject, wherein said second miRNA is enriched in a brain area which is more substantially affected by the second ND than by the first ND;

c) optionally calculating the ratio of the levels of the miRNAs measured in steps (a) and (b);

d) optionally comparing the ratio of the levels of the miRNAs calculated in step (c) with (i) the standard range of ratios of said miRNAs characteristic of the first ND and with (ii) the standard range of ratios of said miRNAs characteristic of the second ND;

e) optionally (i) identifying the subject as being afflicted with the first ND if the ratio of the levels of the miRNAs calculated in step (c) falls within the standard range of ratios of said miRNAs characteristic of the first ND, or (ii) identifying the subject as being afflicted with the second ND if the ratio of the levels of the miRNAs calculated in step (c) falls within the standard range of ratios of said miRNAs characteristic of the second ND.

In one embodiment, step (c) comprises (1) calculating using a suitably programmed processor, the ratio of the levels of the miRNAs measured in steps (a) and (b);

(2) calculating, by the processor and based on the ratio determined in step (c)(1), a first probability based on a first predefined probability distribution curve, wherein the first predefined probability distribution curve corresponds to the first ND;

(3) calculating, by the processor and based on the ratio determined in step (c)(2), a second probability based on a second predefined probability distribution curve, wherein the second predefined probability distribution curve corresponds to the second ND;

step (d) comprises determining, by the processor, a difference between the first probability calculated in step (c)(2) and the second probability calculated in step (c)(3), and step (e) comprises (i) identifying, by the processor, the subject as being afflicted with the first ND when the difference between the first probability and the second probability calculated in step (d) is positive or (ii) identifying the subject as being afflicted with the second ND when the difference between the first probability and the second probability calculated in step (d) is negative.

In one embodiment of any of the above methods, the method further comprises differentiation between the detected neurodegenerative disease ("first ND") and another neurodegenerative disease ("second ND"), which differentiation comprises:

a) measuring the level of a first miRNA in a bodily fluid sample collected from the subject (e.g., the same sample as used in the initial method or a separate sample), wherein said first miRNA is enriched in a brain area which is more substantially affected by the first ND than by the second ND;
b) measuring the level of a second miRNA in the same bodily fluid sample collected from the subject, wherein said second miRNA is enriched in a brain area which is more substantially affected by the second ND than by the first ND;
c) calculating using a suitably programmed processor, the ratio of the levels of the miRNAs measured in steps (a) and (b);
d) calculating, by the processor and based on the ratio determined in step (c), a first probability based on a first predefined probability distribution curve, wherein the first predefined probability distribution curve corresponds to the first ND;
e) calculating, by the processor and based on the ratio determined in step (c), a second probability based on a second predefined probability distribution curve, wherein the second predefined probability distribution curve corresponds to the second ND;
f) determining, by the processor, a difference between the first probability calculated in step (d) and the second probability calculated in step (e), and
g) (i) identifying, by the processor, the subject as being afflicted with the first ND when the difference between the first probability and the second probability calculated in step (f) is positive or (ii) identifying the subject as being afflicted with the second ND when the difference between the first probability and the second probability calculated in step (f) is negative.

In one embodiment of the above method, the first ND is Alzheimer's disease (AD) and the second ND is frontotemporal dementia (FTD) and the pair of the first miRNA and the second miRNA is selected from the group consisting of miR-125b/miR-29a, miR-125b/miR-874, miR-107/miR-335-5p, miR-155/miR-29a, miR-329/miR-874, miR-329/miR-181a, miR-329/miR-411, miR-7/miR-16, miR-451/miR-16, miR-155/miR-335-5p, and let-7e/miR-335-5p.

In one embodiment of the above method, the first ND is Alzheimer's disease (AD) and the second ND is frontotemporal dementia (FTD) and the method comprises measuring the level for one or more miRNA pair combinations selected from the group consisting of miR-125b/miR-29a+miR-107/miR-335-5p+miR-155/miR-29a, miR-125b/miR-29a+miR-125b/miR-874+miR-107/miR-335-5p, miR-125b/miR-874+miR-107/miR-335-5p+miR-155/miR-29a, miR-329/miR-411+miR-329/miR-16, miR-329/miR-874+miR-329/miR-411, miR-329/miR-411+miR-329/miR-16+miR-7/miR-16, and miR-451/miR-16+miR-155/miR-335-5p+let-7e/miR-335-5p.

In one embodiment of the above method, the first ND is Alzheimer's disease (AD) and the second ND is Parkinson's disease (PD) and the pair of the first miRNA and the second miRNA is selected from the group consisting of miR-31/miR-9*, miR-31/miR-99b, miR-31/miR-16, miR-31/miR-29a, miR-138/miR-9*, miR-138/miR-99b, miR-138/miR-181a, miR-138/miR-491-5p, miR-138/miR-335-5p, miR-138/miR-128a, miR-138/miR-146a, miR-138/let-7e, miR-138/miR-16, miR-138/miR-29a, miR-129-3p/miR-9*, miR-129-3p/miR-99b, miR-129-3p/miR-335-5p, miR-129-3p/miR-146a, miR-129-3p/miR-16, miR-129-3p/miR-29a, miR-125b/miR-9*, miR-125b/miR-99b, miR-125b/miR-181a, miR-125b/miR-491-5p, miR-125b/miR-335-5p, miR-125b/miR-128a, miR-125b/miR-146a, miR-125b/let-7e, miR-218/miR-9*, miR-218/miR-16, miR-204/miR-9*, miR-204/miR-99b, miR-204/miR-146a, miR-338-3p/miR-99b, miR-107/miR-99b, and miR-107/miR-491-5p.

In one embodiment of the above method, the first ND is Alzheimer's disease (AD) and the second ND is Parkinson's disease (PD) and the method comprises measuring the level for one or more miRNA pair combinations selected from the group consisting of miR-31/miR-16+miR-129-3p/miR-9*+miR-204/miR-99b, miR-129-3p/miR-16+miR-125b/miR-181a+miR-204/miR-9*, miR-31/miR-99b+miR-129-3p/miR-16+miR-204/miR-9*, miR-31/miR-16+miR-125b/miR-181a+miR-204/miR-9*, and miR-31/miR-16+miR-129-3p/miR-335-5p+miR-204/miR-9*.

In one embodiment of the above method, the first ND is Alzheimer's disease (AD) and the second ND is amyotrophic lateral sclerosis (ALS) and the pair of the first miRNA and the second miRNA is selected from the group consisting of miR-329/miR-206, miR-329/miR-9*, miR-329/miR-99b, miR-329/miR-335-5p, miR-329/miR-146a, miR-329/miR-411, miR-31/miR-206, miR-31/miR-16, miR-129-3p/miR-206, miR-129-3p/miR-16, miR-433/miR-206, miR-433/miR-335-5p, miR-125b/miR-206, miR-125b/miR-335-5p, miR-125b/miR-874, miR-323-3p/miR-206, miR-495/miR-206, miR-204/miR-206, miR-127-3p/miR-206, miR-107/miR-206, miR-107/miR-99b, miR-107/miR-335-5p, miR-107/let-7e, miR-107/miR-146a, miR-107/miR-491-5p, miR-138/miR-206, miR-134/miR-206, miR-9/miR-206, miR-155/miR-206, miR-7/miR-206, miR-338-3p/miR-206, miR-29a/miR-206, miR-338-3p/let-7e, miR-433/miR-411, miR-433/miR-382, and miR-127-3p/miR-411.

In one embodiment of the above method, the first ND is Alzheimer's disease (AD) and the second ND is amyotrophic lateral sclerosis (ALS) and the method comprises measuring the level for one or more miRNA pair combinations selected from the group consisting of miR-31/miR-206+miR-125b/miR-335-5p, miR-31/miR-206+miR-125b/miR-335-5p+miR-107/miR-335-5p, miR-31/miR-206+miR-125b/miR-335-5p+miR-107/miR-491-5p, miR-125b/miR-335-5p+miR-107/let-7e+miR-138/miR-206, miR-125b/miR-335-5p+miR-107/miR-491-5p+miR-338-3p/miR-206, miR-125b/miR-335-5p+miR-107/let-7e+miR-338-3p/miR-206, miR-125b/miR-335-5p+miR-323-3p/miR-206+miR-107/let-7e, and miR-433/miR-382+miR-127-3p/miR-411.

In one embodiment of the above method, the first ND is frontotemporal dementia (FTD) and the second ND is Parkinson's disease (PD) and the pair of the first miRNA and the second miRNA is selected from the group consisting of miR-218/miR-9*, miR-218/miR-99b, miR-138/miR-99b, miR-138/miR-181a, miR-138/miR-491-5p, miR-31/miR- 9*, miR-31/miR-99b, miR-129-3p/miR-9*, miR-129-3p/miR-99b, miR-204/miR-9*, miR-204/miR-99b, miR-338-3p/miR-99b, miR-338-3p/miR-491-5p, miR-338-3p/miR-107, miR-338-3p/let-7e, miR-338-3p/miR-146a, miR-874/miR-99b, miR-125b/miR-99b, miR-29a/miR-99b, miR-323-3p/miR-127-3p, miR-411/miR-127-3p, miR-155/miR-99b, miR-335-5p/miR-99b, and miR-382/miR-134.

In one embodiment of the above method, the first ND is frontotemporal dementia (FTD) and the second ND is Parkinson's disease (PD) and the method comprises measuring the level for one or more miRNA pair combinations selected from the group consisting of miR-129-3p/miR-9*+miR-338-3p/miR-491-5p, miR-129-3p/miR-9*+miR-338-3p/miR-99b+miR-323-3p/miR-127-3p, miR-129-3p/miR-9*+miR-338-3p/miR-491-5p+miR-411/miR-127-3p, miR-129-3p/miR-9*+miR-338-3p/miR-491-5p+miR-323-3p/miR-127-3p, miR-204/miR-9*+miR-338-3p/miR-491-5p+miR-323-3p/miR-127-3p, miR-129-3p/miR-9*+miR-29a/miR-99b+miR-323-3p/miR-127-3p, and miR-138/miR-181a+miR-129-3p/miR-9*+miR-411/miR-127-3p.

In one embodiment of the above method, the first ND is frontotemporal dementia (FTD) and the second ND is amyotrophic lateral sclerosis (ALS) and the pair of the first miRNA and the second miRNA is selected from the group consisting of miR-31/miR-206, miR-138/miR-206, miR-29a/miR-206, miR-129-3p/miR-206, miR-204/miR-206, miR-338-3p/miR-206, miR-338-3p/let-7e, miR-7/miR-206, miR-128a/miR-206, miR-16/miR-206, miR-125b/miR-206, miR-874/miR-206, miR-218/miR-206, miR-29a/miR-155, miR-338-3p/miR-181a, miR-338-3p/miR-335-5p, miR-338-3p/miR-491-5p, miR-338-3p/miR-146a, miR-323-3p/miR-127-3p, and miR-129-3p/miR-9*.

In one embodiment of the above method, the first ND is frontotemporal dementia (FTD) and the second ND is amyotrophic lateral sclerosis (ALS) and the method comprises measuring the level for one or more miRNA pair combinations selected from the group consisting of miR-29a/miR-206+miR-338-3p/let-7e, miR-129-3p/miR-206+miR-338-3p/let-7e, miR-204/miR-206+miR-338-3p/let-7e, miR-138/miR-206+miR-338-3p/let-7e, miR-129-3p/miR-206+miR-338-3p/let-7e+miR-125b/miR-206, miR-129-3p/miR-206+miR-338-3p/let-7e+miR-874/miR-206, miR-129-3p/miR-206+miR-338-3p/let-7e+miR-7/miR-206, and miR-338-3p/miR-181a+miR-338-3p/miR-335-5p+miR-323-3p/miR-127-3p.

In one embodiment of the above method, the first ND is Parkinson's disease (PD) and the second ND is amyotrophic lateral sclerosis (ALS) and the pair of the first miRNA and the second miRNA is selected from the group consisting of miR-329/miR-206, miR-9*/miR-206, miR-433/miR-206, miR-370/miR-206, miR-134/miR-206, miR-323-3p/miR-206, miR-9/miR-206, miR-99b/miR-206, miR-495/miR-206, miR-382/miR-206, miR-491-5p/miR-206, miR-29a/miR-206, miR-411/miR-206, miR-181a/miR-206, miR-155/miR-206, miR-146a/miR-206, miR-7/miR-206, miR-107/miR-204, miR-107/let-7e, miR-107/miR-335-5p, miR-107/miR-146a, miR-128a/miR-874, miR-128a/let-7e, miR-329/miR-382, miR-433/miR-382, and miR-433/miR-411.

In one embodiment of the above method, the first ND is Parkinson's disease (PD) and the second ND is amyotrophic lateral sclerosis (ALS) and the method comprises measuring the level for one or more miRNA pair combinations selected from the group consisting of miR-29a/miR-206+miR-7/miR-206, miR-9*/miR-206+miR-7/miR-206, miR-9*/miR-206+miR-155/miR-206+miR-7/miR-206, miR-107/miR-204+miR-107/miR-146a+miR-128a/miR-874, miR-107/miR-204+miR-128a/miR-874+miR-128a/let-7e, miR-107/miR-335-5p+miR-128a/miR-874+miR-128a/let-7e, miR-107/miR-204+miR-107/miR-146a+miR-128a/let-7e, and miR-329/miR-382+miR-433/miR-382+miR-433/miR-411.

In one aspect, the invention provides a method for determining whether a subject is at risk to progress to dementia, which method comprises:

a) measuring the level of a first miRNA and a second miRNA in a bodily fluid sample collected from the subject and calculating the ratio of the level of the first miRNA and the level of the second miRNA in a pair selected from the group consisting of miR-181a/miR-370, miR-335-5p/miR-370, miR-335-5p/let-7e, miR-135a/miR-370, miR-132/miR-370, miR-128a/miR-370, miR-128a/let-7e, miR-107/miR-370, miR-410/miR-370, miR-410/miR-433, miR-411/miR-370, miR-382/miR-370, miR-323-3p/miR-370, miR-127/miR-370, miR-134/miR-370, and miR-433/miR-370;

b) optionally comparing the ratio of the levels of the first miRNA and the second miRNA calculated in step (a) with a corresponding control ratio, and c) optionally (i) identifying the subject as at risk to progress to AD when the ratio of the levels of the miRNAs calculated in step (a) is higher than the corresponding control ratio or (ii) identifying the subject as not at risk to progress to AD when the ratio of the levels of the miRNA calculated in step (a) is not higher than the corresponding control ratio.

In some embodiments, the dementia is Alzheimer's Disease (AD).

In another embodiment, the invention provides a method for determining whether a subject is at risk to progress to dementia which method comprises:

a) measuring the level of a first miRNA and a second miRNA in a bodily fluid sample collected from the subject and calculating the sum of the ratios of the each of the first miRNA and second miRNA pairs in a combination selected from the group consisting of miR-410/miR-370 miR-181a miR-370 miR-127/miR-370+miR-128a/let-7e; miR-323-3p/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370;

b) optionally comparing the sum of the ratios calculated in step (a) with a corresponding control sum of ratios, and c) optionally (i) identifying the subject as at risk to progress to AD when the sum of ratios calculated in step (a) is higher than the corresponding control sum of ratios or (ii) identifying the subject as not at risk to progress to AD when the sum of ratios calculated in step (a) is not higher than the corresponding control sum of ratios.

In another aspect, the invention provides a method for determining whether a subject is at risk to progress to dementia which method comprises:

a) measuring the level of a first miRNA and a second miRNA in a bodily fluid sample collected from the subject for a combination of miRNA pairs selected from the group consisting of miR-410/miR-370+miR-181a/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370; miR-410/miR-370+miR-181a/miR-370+miR-128a/let-7e; miR-410/miR-370+miR-127/miR-370+miR-128a/let-7e; miR-323-3p/miR-370+miR-181a/miR-370+ miR-128a/let-7e; miR-323-3p/miR-370+miR-127/miR-370+miR-128a/let-7e; miR-323-3p/miR-370+miR-127/miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; miR-181a/miR-370+miR-127/miR-370+miR-128a/let-7e; and miR-410/miR-433+miR-127/miR-370+miR-128a/let-7e, b) using Logistic Regression, determining the probability of a subject belonging to progressors or non-progressors, and c) (i) identifying the subject as at risk to progress to dementia when the probability of the subject belonging to progressors determined in step (b) is higher than 0.5, or (ii) identifying the subject as not at risk to progress to dementia when the probability of the subject belonging to progressors determined in step (b) is less than 0.5.

In one embodiment, the invention further comprises determining whether the subject is at risk to progress to Alzheimer's dementia or dementia associated with another neurodegenerative disease, which method comprises:

a) measuring the level of a first miRNA and a second miRNA in a bodily fluid sample collected from the subject and calculating the ratio of the level of the first miRNA and the level of the second miRNA in a pair selected from the group consisting of miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410; miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p;

b) comparing the ratio of the levels of the first miRNA and the second miRNA calculated in step (a) with a corresponding control ratio, and c) (i) identifying the subject as at risk to progress to AD dementia when the ratio of the levels of the miRNAs calculated in step (a) is higher than the corresponding control ratio or (ii) identifying the subject as at risk to progress to dementia associated with another neurodegenerative disease when the ratio of the levels of the miRNA calculated in step (a) is not higher than the corresponding control ratio.

In another embodiment, the invention further comprises determining whether the subject is at risk to progress to Alzheimer's (AD) dementia or dementia associated with another neurodegenerative disease, which method comprises:

a) measuring the level of a first miRNA and a second miRNA in a bodily fluid sample collected from the subject for a combination of miRNA pairs selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134; miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a/let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, and miR-410/miR-433+miR-323-3p/miR-485-5p+miR-135a/miR-134;

b) using Logistic Regression, determining the probability of a subject belonging to the group of AD dementia and dementia associated with another neurodegenerative disease, and c) (i) identifying the subject as at risk to progress to AD dementia when the probability of the subject belonging to the group of AD dementia determined in step (b) is higher than 0.5, or (ii) identifying the subject as not at risk to progress to AD dementia when the probability of the subject belonging to the group of AD dementia determined in step (b) is less than 0.5.

In another embodiment, the invention further comprises determining whether the subject is at risk to progress to Alzheimer's dementia or dementia associated with another neurodegenerative disease, which method comprises:

a) measuring the level of a first miRNA and a second miRNA in a bodily fluid sample collected from the subject and calculating the ratio of the level of the first miRNA and the level of the second miRNA in a pair selected from the group consisting of miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410; miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p;

b) comparing the ratio of the levels of the first miRNA and the second miRNA calculated in step (a) with a corresponding control ratio, and c) (i) identifying the subject as at risk to progress to AD dementia when the ratio of the levels of the miRNAs calculated in step (a) is higher than the corresponding control ratio or (ii) identifying the subject as at risk to progress to dementia associated with another neurodegenerative disease when the ratio of the levels of the miRNA calculated in step (a) is not higher than the corresponding control ratio.

In another embodiment, the invention further comprises determining whether the subject is at risk to progress to Alzheimer's (AD) dementia or dementia associated with another neurodegenerative disease, which method comprises:

a) measuring the level of a first miRNA and a second miRNA in a bodily fluid sample collected from the subject for a combination of miRNA pairs selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134; miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a/let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, and miR-410/miR-433+miR-323-3p/miR-485-5p+miR-135a/miR-134;

b) using Logistic Regression, determining the probability of a subject belonging to the group of AD dementia and dementia associated with another neurodegenerative disease, and c) (i) identifying the subject as at risk to progress to AD dementia when the probability of the subject belonging to the group of AD dementia determined in step (b) is higher than 0.5, or (ii) identifying the subject as not at risk to progress to AD dementia when the probability of the subject belonging to the group of AD dementia determined in step (b) is less than 0.5.

In another embodiment, the invention provides a method for determining whether the subject is at risk to progress to Alzheimer's Disease (AD), which method comprises:

a) measuring the level of a first miRNA and a second miRNA in a bodily fluid sample collected from the subject and calculating the sum of the ratios of the each of the first miRNA and second miRNA pairs in a combination selected from the group consisting of miR-410/miR-370+miR-181a/miR-370+miR-128a/let-7e; miR-410/miR-370+miR-127/miR-370+miR-128a/let-7e; miR-323-3p/miR-370+miR-181a/miR-370+miR-128a/let-7e; miR-323-3p/miR-370+miR-127/miR-370+miR-128a/let-7e; miR-323-3p/miR-370+miR-127/miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; miR-181a/miR-370+miR-127/miR-370+miR-128a/let-7e; and miR-410/miR-433+miR-127/miR-370+miR-128a/let-7e;

b) optionally comparing the sum of the ratios calculated in step (a) with a corresponding control sum of ratios, and c) optionally (i) identifying the subject as at risk to progress to AD when the sum of ratios calculated in step (a) is higher than the corresponding control sum of ratios or (ii) identifying the subject as not being at risk to progress to AD when the sum of ratios calculated in step (a) is not higher than the corresponding control sum of ratios.

In one aspect, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating the ratio of the level of the first miRNA and the level of the second miRNA in a pair selected from the group consisting of miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410;

b) optionally comparing the ratio of the levels of the first miRNA and the second miRNA calculated in step (a) with a corresponding control ratio, and c) optionally (i) identifying the subject as at risk to progress to AD as a $A\beta_{42}$ positive progressor when the ratio of the levels of the miRNAs calculated in step (a) is higher than the corresponding control ratio or (ii) identifying the subject as a future $A\beta_{42}$ negative progressor when the ratio of the levels of the miRNA calculated in step (a) is not higher than the corresponding control ratio.

In another embodiment, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating the sum of the ratios of the each of the first miRNA and the second miRNA pairs in a combination selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-135a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR- 181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410;

b) optionally comparing the sum of the ratios calculated in step (a) with a corresponding control sum of ratios, and c) optionally (i) identifying the subject as at risk to progress to AD as a $A\beta_{42}$ positive progressor when the sum of ratios calculated in step (a) is higher than the corresponding control sum of ratios or (ii) identifying the subject as a future $A\beta_{42}$ negative progressor when the sum of ratios calculated in step (a) is not higher than the corresponding control sum of ratios.

In another embodiment, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating, from a body fluid collected from the subject, the sum of the ratios of the each of the first miRNA and second miRNA pairs in a combination selected from the group consisting of miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134;

b) optionally comparing the sum of the ratios calculated in step (a) with a corresponding control sum of ratios, and c) optionally (i) identifying the subject as at risk to progress to AD as a future $A\beta_{42}$ positive progressor when the sum of ratios calculated in step (a) is higher than the corresponding control sum of ratios or (ii) identifying the subject as a future $A\beta_{42}$ negative progressor when the sum of ratios calculated in step (a) is not higher than the corresponding control sum of ratios.

In one aspect, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating, from a body fluid collected from the subject, the ratio of the level of the first miRNA and the level of the second miRNA in a pair selected from the group consisting of miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p;

b) optionally comparing the ratio of the levels of the first miRNA and the second miRNA calculated in step (a) with a corresponding control ratio, and c) optionally (i) identifying the subject as at risk to progress to AD as a $A\beta_{42}$ positive progressor when the ratio of the levels of the miRNAs calculated in step (a) is higher than the corresponding control ratio or (ii) identifying the subject as a $A\beta_{42}$ positive non-progressor not at risk to progress to AD when the ratio of the levels of the miRNA calculated in step (a) is not higher than the corresponding control ratio.

In another embodiment, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating, from a body fluid collected from the subject, the sum of the ratios of the each of the first miRNA and the second miRNA pairs in a combination selected from the group consisting of miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p;

b) optionally comparing the sum of the ratios calculated in step (a) with a corresponding control sum of ratios, and c) optionally (i) identifying the subject as at risk to progress to AD as a $A\beta_{42}$ positive progressor when the sum of ratios calculated in step (a) is higher than the corresponding control sum of ratios or (ii) identifying the subject as a $A\beta_{42}$ positive non-progressor who is not at risk to progress to AD as a when the sum of ratios calculated in step (a) is not higher than the corresponding control sum of ratios.

In another embodiment, the invention provides a method for determining whether the subject is at risk to progress to Alzheimer's Disease (AD) as a $A\beta_{42}$ positive progressor, which method comprises:

a) measuring the level of a first miRNA and a second miRNA in a bodily fluid sample collected from the subject and calculating, from a body fluid collected from the subject, the sum of the ratios of the each of the first miRNA and the second miRNA pairs in a combination selected from the group consisting of miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a/let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, and miR-410/miR-433+miR-323-3p/miR-485-5p+miR-135a/miR-134;

b) optionally comparing the sum of the ratios calculated in step (a) with a corresponding control sum of ratios, and c) optionally (i) identifying the subject as at risk to progress to AD as a Aβ$_{42}$ positive progressor when the sum of ratios calculated in step (a) is higher than the corresponding control sum of ratios or (ii) identifying the subject as a Aβ$_{42}$ positive non-progressor who is not at risk to progress to AD as a when the sum of ratios calculated in step (a) is not higher than the corresponding control sum of ratios.

In one aspect, the invention provides a method for treating a subject at risk to progress to Alzheimer's Disease (AD), which method comprises:

a) measuring the level of a first miRNA and a second miRNA in a bodily fluid sample collected from the subject and calculating the ratio of the level of the first miRNA and the level of the second miRNA in a pair selected from the group consisting of miR-181a/miR-370, miR-335-5p/miR-370, miR-335-5p/let-7e, miR-135a/miR-370, miR-132/miR-370, miR-128a/miR-370, miR-128a/let-7e, miR-107/miR-370, miR-410/miR-370, miR-410/miR-433, miR-411/miR-370, miR-382/miR-370, miR-323-3p/miR-370, miR-127/miR-370, miR-134/miR-370, and miR-433/miR-370;

b) comparing the ratio of the levels of the first miRNA and the second miRNA calculated in step (a) with a corresponding control ratio, and c) administering a therapeutic or preventative treatment to the subject if the ratio of the levels of the miRNAs calculated in step (a) is higher than the corresponding control ratio.

In another embodiment is provided a method for treating a subject at risk to progress to Alzheimer's Disease (AD), which method comprises:

a) measuring the level of a first miRNA and a second miRNA in a bodily fluid sample collected from the subject and calculating the ratio of the level of the first miRNA and the level of the second miRNA in a pair selected from the group consisting of miR-181a/miR-370, miR-335-5p/miR-370, miR-335-5p/let-7e, miR-135a/miR-370, miR-132/miR-370, miR-128a/miR-370, miR-128a/let-7e, miR-107/miR-370, miR-410/miR-370, miR-410/miR-433, miR-411/miR-370, miR-382/miR-370, miR-323-3p/miR-370, miR-127/miR-370, miR-134/miR-370, miR-433/miR-370; miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410;

b) comparing the ratio of the levels of the first miRNA and the second miRNA calculated in step (a) with a corresponding control ratio, and c) administering a therapeutic or preventative treatment to the subject if the ratio of the levels of the miRNAs calculated in step (a) is higher than the corresponding control ratio.

In another embodiment is provided a method for treating a subject at risk to progress to Alzheimer's Disease (AD), which method comprises:

a) measuring the level of a first miRNA and a second miRNA in a bodily fluid sample collected from the subject for a combination of miRNA pairs selected from the group consisting of miR-410/miR-370+miR-181a/miR-370+miR-127/miR-370+miR-128a/let-7e; miR-323-3p/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370; miR-410/miR-370+miR-181a/miR-370+miR-128a/let-7e; miR-410/miR-370+miR-127/miR-370+miR-128a/let-7e; miR-323-3p/miR-370+miR-181a/miR-370+miR-128a/let-7e; miR-323-3p/miR-370+miR-127/miR-370+miR-128a/let-7e; miR-323-3p/miR-370+miR-127/miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; miR-181a/miR-370+miR-127/miR-370+miR-128a/let-7e; and miR-410/miR-433+miR-127/miR-370+miR-128a/let-7e;

b) using Logistic Regression, determining the probability of a subject belonging to progressors or non-progressors, and c) administering a therapeutic or preventative treatment to the subject if the probability of the subject belonging to progressors determined in step (b) is higher than 0.5.

In another embodiment is provided a method for treating Alzheimer's dementia in a subject, which method comprises:

a) measuring the level of a first miRNA and a second miRNA in a bodily fluid sample collected from the subject for a combination of miRNA pairs selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134; miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p;

b) using Logistic Regression, determining the probability of a subject belonging to AD group and non-AD group, and c) administering a therapeutic or preventative treatment to the subject if the probability of the subject belonging to AD group determined in step (b) is higher than 0.5.

In another embodiment, the invention provides a method for treating a subject at risk to progress to Alzheimer's Disease (AD), which method comprises:
a) measuring the level of a first miRNA and a second miRNA in a bodily fluid sample collected from the subject and calculating the sum of the ratios of the each of the first miRNA and second miRNA pairs in a combination selected from the group consisting of miR-410/miR-370 miR-181a miR-370 miR-127/miR-370+miR-128a/let-7e; miR-323-3p/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370;
b) comparing the sum of the ratios calculated in step (a) with a corresponding control sum of ratios, and
c) administering a therapeutic or preventative treatment to the subject if the sum of ratios of the levels of the miRNAs calculated in step (a) is higher than the corresponding control sum of ratios.

In another embodiment, the invention provides a method for treating Alzheimer's Disease (AD) in a subject, which method comprises:
a) measuring the level of a first miRNA and a second miRNA in a bodily fluid sample collected from the subject and calculating the sum of the ratios of the each of the first miRNA and the second miRNA pairs in a combination selected from the group consisting of miR-410/miR-370+miR-181a/miR-370+miR-128a/let-7e; miR-410/miR-370+miR-127/miR-370+miR-128a/let-7e; miR-323-3p/miR-370+miR-181a/miR-370+miR-128a/let-7e; miR-323-3p/miR-370+miR-127/miR-370+miR-128a/let-7e; miR-323-3p/miR-370+miR-127/miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; miR-181a/miR-370+miR-127/miR-370+miR-128a/let-7e; and miR-410/miR-433+miR-127/miR-370+miR-128a/let-7e;
b) comparing the sum of the ratios calculated in step (a) with a corresponding control sum of ratios, and
c) administering a therapeutic or preventative treatment to the subject if the sum of ratios of the levels of the miRNAs calculated in step (a) is higher than the corresponding control sum of ratios.

In another embodiment, the invention provides a method for treating Alzheimer's Disease (AD) in a subject, which method comprises:
a) measuring the level of a first miRNA and a second miRNA in a bodily fluid sample collected from the subject and calculating the ratio of the level of the first miRNA and the level of the second miRNA in a pair selected from the group consisting of miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410;
b) comparing the ratio of the levels of the first miRNA and the second miRNA calculated in step (a) with a corresponding control ratio, and
c) administering a therapeutic or preventative treatment to the subject if the ratio of the levels of the miRNAs calculated in step (a) is higher than the corresponding control ratio.

In another embodiment, the invention provides a method for treating Alzheimer's Disease (AD) in a subject, which method comprises:
a) measuring the level of a first miRNA and a second miRNA in a bodily fluid sample collected from the subject and calculating the sum of the ratios of the each of the first miRNA and the second miRNA pairs in a combination selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410;
b) comparing the sum of the ratios calculated in step (a) with a corresponding control sum of ratios, and
c) administering a therapeutic or preventative treatment to the subject if the sum of ratios of the levels of the miRNAs calculated in step (a) is higher than the corresponding control sum of ratios.

In another embodiment, the invention provides a method for treating Alzheimer's Disease (AD) in a subject, which method comprises:
a) measuring the level of a first miRNA and a second miRNA in a bodily fluid sample collected from the subject and calculating the sum of the ratios of the each of the first miRNA and second miRNA pairs in a combination selected from the group consisting of miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134;
b) comparing the sum of the ratios calculated in step (a) with a corresponding control sum of ratios, and
c) administering a therapeutic or preventative treatment to the subject if the sum of ratios of the levels of the miRNAs calculated in step (a) is higher than the corresponding control sum of ratios.

In another embodiment, the invention provides a method for treating Alzheimer's Disease (AD) in a subject, which method comprises:
a) measuring the level of a first miRNA and a second miRNA in a bodily fluid sample collected from the subject and calculating the ratio of the level of the first miRNA and the level of the second miRNA in a pair selected from the group consisting of miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p;

b) comparing the ratio of the levels of the first miRNA and the second miRNA calculated in step (b) with a corresponding control ratio, and c) administering a therapeutic or preventative treatment to the subject if the ratio of the levels of the miRNAs calculated in step (a) is higher than the corresponding control ratio.

In another embodiment, the invention provides a method for treating Alzheimer's Disease (AD) in a subject, which method comprises:

a) measuring the level of a first miRNA and a second miRNA in a bodily fluid sample collected from the subject and calculating the sum of the ratios of the each of the first miRNA and the second miRNA pairs in a combination selected from the group consisting of miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p;

b) comparing the sum of the ratios calculated in step (a) with a corresponding control sum of ratios, and c) administering a therapeutic or preventative treatment to the subject if the sum of ratios of the levels of the miRNAs calculated in step (a) is higher than the corresponding control sum of ratios.

In another aspect, the invention provides a method for treating AD dementia in a subject, which method comprises:

a) measuring the level of a first miRNA and a second miRNA in a bodily fluid sample collected from the subject for a combination of miRNA pairs selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134; miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p;

b) using Logistic Regression, determining the probability of a subject belonging to AD group and non-AD group, and c) administering a therapeutic or preventative treatment to the subject if the probability of the subject belonging to AD group determined in step (b) is higher than 0.5.

In another aspect, the invention provides a method for treating Alzheimer's disease in a subject, which method comprises:

a) measuring the level of a first miRNA and a second miRNA in a bodily fluid sample collected from the subject for a combination of miRNA pairs selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, and miR-128a/let-7e+miR-370/miR-433+miR-135a/miR-134; miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/ miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p;

b) using Logistic Regression, determining the probability of a subject belonging to AD group and non-AD group, and c) administering a therapeutic or preventative treatment to the subject if the probability of the subject belonging to AD group determined in step (b) is higher than 0.5.

In another aspect, the invention provides a method for treating Alzheimer's Disease (AD) in a subject, which method comprises:

a) measuring the level of a first miRNA and a second miRNA in a bodily fluid sample collected from the subject and calculating the ratio of the level of the first miRNA and the level of the second miRNA in a pair selected from the group consisting of miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p;

b) comparing the ratio of the levels of the first miRNA and the second miRNA calculated in step (b) with a corresponding control ratio, and c) administering a therapeutic or preventative treatment to the subject if the ratio of the levels of the miRNAs calculated in step (a) is higher than the corresponding control ratio.

In another embodiment, the invention provides a method for determining whether the subject is at risk to progress to Alzheimer's Disease (AD), which method comprises:
a) measuring the level of a first miRNA and a second miRNA in a bodily fluid sample collected from the subject and calculating the sum of the ratios of the each of the first miRNA and the second miRNA pairs in a combination selected from the group consisting of miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a/let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, and miR-410/miR-433+miR-323-3p/miR-485-5p+miR-135a/miR-134;
b) comparing the sum of the ratios calculated in step (a) with a corresponding control sum of ratios, and
c) administering a therapeutic or preventative treatment to the subject if the sum of ratios of the levels of the miRNAs calculated in step (a) is higher than the corresponding control sum of ratios.

In one embodiment of any of the above methods, calculation is performed using a suitably programmed processor.

In one embodiment of any of the above methods, the method comprises measuring the levels of the miRNAs in two or more bodily fluid samples collected from the subject, wherein the samples have been collected at spaced apart time points.

In one embodiment of any of the above methods involving bodily fluid samples which have been collected at spaced apart time points, the bodily fluid samples are obtained several months apart (e.g., 3-6 months apart).

In one embodiment of any of the above methods, the method further comprises normalizing the levels of the first and second miRNAs to the level of a normalizer miRNA. In one specific embodiment, the normalizer miRNA is miRNA which is expressed in numerous tissues but is not significantly expressed in brain.

In one embodiment of any of the above methods, the subject is human. In another embodiment of any of the above methods, the subject is an experimental animal (e.g., an animal model of a neurodegenerative disorder).

In one embodiment of any of the above methods, the bodily fluid is selected from the group consisting of blood plasma, serum, urine, and saliva. Any other bodily fluid can also be used, preferably, those bodily fluids that allow low cost non-invasive or minimally invasive collection and analysis.

In one embodiment of any of the above methods, the method comprises the step of collecting the bodily fluid sample(s) from the subject (e.g., prior to step (a)).

In one embodiment of any of the above methods, the level of the miRNAs is determined using a method selected from the group consisting of hybridization, RT-PCR, and sequencing. Non-limiting examples of useful methods for measuring miRNA level in bodily fluids include hybridization with selective probes (e.g., using Northern blotting, bead-based flow-cytometry, oligonucleotide microchip [microarray], or solution hybridization assays such as Ambion mirVana miRNA Detection Kit), polymerase chain reaction (PCR)-based detection (e.g., stem-loop reverse transcription-polymerase chain reaction [RT-PCR], quantitative RT-PCR based array method [qPCR-array]), direct sequencing by one of the next generation sequencing technologies (e.g., Helicos small RNA sequencing, miRNA BeadArray (Illumina), Roche 454 (FLX-Titanium), and ABI SOLiD), or various microfluidic technologies. For review of additional applicable techniques see, e.g., Chen et al., BMC Genomics, 2009, 10:407; Kong et al., J Cell Physiol. 2009; 218:22-25. One of the preferred types of techniques are RT-PCR-based techniques as such techniques allow to achieve good sensitivity and specificity.

In one embodiment of any of the above methods, prior to measuring miRNA level, the miRNA is purified from the bodily fluid sample. miRNAs can be isolated and purified from bodily fluids by various methods, including, without limitation, the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction, concentration and purification on anion-exchangers, magnetic beads covered by RNA-binding substances, or adsorption of certain miRNA on complementary oligonucleotides.

In one embodiment of any of the above methods, the method further comprises reducing or eliminating degradation of the miRNAs. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecylsulphate (SDS), or a combination thereof. Reducing miRNA degradation in bodily fluid samples is particularly important when sample storage and transportation is required prior to miRNA quantification.

To account for possible losses of a given miRNA during purification, potential RT-PCR inhibition, miRNA contaminants derived from dying or damaged blood or urine cells during sample isolation and treatment, variations in kidney filtration, etc., various additional methods of experimental data normalization can be employed. For example, the following quality control (QC) and normalization methods can be used in the present invention:

a) Ubiquitous miRNAs can be used for QC by comparing their concentrations in subject's bodily fluid with pre-established normal values.

b) Synthetic small RNA (e.g., non-human miRNA) oligonucleotides can be synthesized and used as controls for losses during purification and RT-PCR inhibition (by adding them to bodily fluid samples before RNA purification).

c) To account for variations in kidney filtration (when working with urine samples), miRNA concentration in urine can be normalized on creatinine and/or albumin level.

In one embodiment of any of the above methods, neurodegenerative disorder detection based on miRNA levels is combined with additional methods of detection. Non-limiting examples of such additional methods include, e.g., genetic testing, hearing test, eye and/or vision exam, positron emission tomography (PET), computed tomography (CT), magnetic resonance imaging (MRI), multiphoton imaging, magnetoencephalography (MEG), electroencephalography (EEG), etc.

In one embodiment of any of the above methods, the method further comprises administering a therapeutic or preventive treatment to the subject. Non-limiting examples of useful drug treatments include, for example, administration of dopamine-replenishing or dopamine mimicking drugs such as, e.g., levodopa or levodopa combination treatments, which may include administration with dopa decarboxylase inhibitors (e.g., carbidopa, benserazide); dopamine enhancers, such as catechol o-methyltransferase (COMT) inhibitors (e.g., entacapone, tolcapone); dopamine receptor agonists (e.g., ropinirole, pramipexole, rotigotine, apomorphine, pergolide, bromocriptine); monoamine oxidase (MAOIs) inhibitors, which can be used alone or with levodopa (e.g., selegiline, rasagiline, zydis selegiline HCl salt); amantadine (used to combat tremor and side effects of levodopa administration); anti-cholinergics (e.g., trihexyphenidyl, benztropine, donepezil, galantamine, rivastigmine); antiglutamatergics (e.g., memantine, safinomide); riluzole; neurturin therapies; anti-apoptotics (e.g., omigapil, CEP-1347); anti-psychotics (e.g., olanzepine, quetiapine, risperidone, ziprasidone, aripiprazole, paliperidone); promitochondrials (e.g., Coenzyme Qio, creatine); calcium channel blockers, including isradipine, and growth factors such as GDNF; anti-Abeta antibodies, as well as drugs or vaccines targeting alpha-synuclein. Non-limiting examples of useful surgical therapies include, for example, deep brain stimulation (DBS), involving implantation of a battery-powered electrode in the brain; operations directly on neural tissue (e.g., thalamotomy, pallidotomy, subthalmatomy); and dopamergic cell transplant. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms. Non-limiting examples of useful food supplements include, for example, antioxidants such as vitamins C and E, calcium, ginger root, green tea and green tea extracts, St. John's Wort, Ginkgo biloba, milk thistle, vitamin B12, and folic acid. Effective treatment can mean patient improvement (decrease of a biomarker miRNA ratio) or prevention/inhibition of further disease development (biomarker miRNA ratio stays the same or increases slower).

In one embodiment of any of the above methods, the method further comprises administering one or more of the following therapeutic or preventive treatments to the subject to treat AD: apomorphine, donepezil, galantamine, raviastigmine, memantine, anti-psychotics (e.g., olanzepine, quetiapine, risperidone, ziprasidone, aripiprazole, paliperidone), anti-Abeta antibodies, vitamin C, vitamin E, ginger root, green tea and green tea extracts, *Ginkgo biloba*, milk thistle, vitamin B12, and folic acid. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms. In one embodiment of any of the above methods, the method further comprises administering one or more of the following therapeutic or preventive treatments to the subject to treat PD: administration of dopamine-replenishing or dopamine mimicking drugs such as, e.g., levodopa or levodopa combination treatments, which may include administration with dopa decarboxylase inhibitors (e.g., carbidopa, benserazide); dopamine enhancers, such as catechol o-methyltransferase (COMT) inhibitors (e.g., entacapone, tolcapone); dopamine receptor agonists (e.g., ropinirole, pramipexole, rotigotine, apomorphine, pergolide, bromocriptine); monoamine oxidase (MAOIs) inhibitors, which can be used alone or with levodopa (e.g., selegiline, rasagiline, zydis selegiline HCl salt); amantadine (used to combat tremor and side effects of levodopa administration); anti-cholinergics (e.g., trihexyphenidyl, benztropine, galantamine, rivastigmine); antiglutamatergics (e.g., safinomide); riluzole; neurturin therapies; anti-apoptotics (e.g., omigapil, CEP-1347); anti-psychotics (e.g., olanzepine, quetiapine, risperidone, ziprasidone, aripiprazole, paliperidone); promitochondrials (e.g., Coenzyme Qio, creatine); calcium channel blockers, including isradipine, and growth factors such as GDNF; drugs or vaccines targeting alpha-synuclein, surgical therapies (e.g., deep brain stimulation (DBS), involving implantation of a battery-powered electrode in the brain; operations directly on neural tissue (e.g., thalamotomy, pallidotomy, subthalmatomy); and dopamergic cell transplant), vitamin C, vitamin E, calcium, ginger root, green tea, green tea extracts, St. John's Wort, and milk thistle. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

In one embodiment of any of the above methods, the method further comprises administering one or more of the following therapeutic or preventive treatments to the subject to treat frontotemporal dementia (FTD): anti-psychotics (e.g., olanzepine, quetiapine, risperidone, ziprasidone, aripiprazole, paliperidone); *Gingko biloba*, vitamin B12, and folic acid. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

In one embodiment of any of the above methods, the method further comprises administering monoamine oxidase (MAOIs) inhibitors to treat progressive supranuclear palsy (PSP). Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with MAOI treatment) to alleviate disease symptoms.

In one embodiment of any of the above methods, the method further comprises administering one or more of the following therapeutic or preventive treatments to the subject to treat amylotropic lateral sclerosis (ALS): riluzole and omigapil. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

In one embodiment of any of the above methods, the method further comprises administering one or more of the following therapeutic or preventive treatments to the subject to treat mild cognitive impairment (MCI): vitamin C, vitamin E, ginger root, green tea and green tea extracts, *Ginkgo biloba*, milk thistle, vitamin B12, and folic acid. Diet, exercise, physical, occupational and/or speech-language therapies, nutritional support as well as symptomatic treatments for controlling seizures, muscle stiffness, spasticity, constipation, depression, anxiety, fatigue etc. and may also be used (separately or in combination with other treatments) to alleviate disease symptoms.

In one embodiment of any of the above disease detection or disease progression monitoring methods, the method further comprises recruiting the subject in a clinical trial.

In conjunction with the above methods of the invention, the invention also provides various kits. Non-limiting examples of the kits of the invention include:

1. A kit for detecting a neurodegenerative disorder (and/or for differentiating two or more neurodegenerative disorders) comprising primers and/or probes specific for one or more pairs of miRNAs selected from the pairs provided in Tables 3-22 and 24-25, below.

2. A kit for detecting a neurodegenerative disorder (and/or for differentiating two or more neurodegenerative disorders) comprising primers and/or probes specific for one or more combinations of pairs of miRNAs selected from the pair combinations provided in Tables 7-10, 12, 14, 16, 18, 20, 22, and 25, below.

3. A kit for detecting Mild Cognitive Impairment (MCI) or pre-MCI comprising primers and/or probes specific for (i) one or more miRNA selected from the group consisting of miR-132, miR-134, miR-135a, miR-323-3p, miR-335-5p, miR-382, and miR-411, and (ii) one or more miRNA selected from the group consisting of miR-127-3p, miR-370, miR-410, miR-433, miR-7, miR-451, and miR-9.

4. A kit for detecting MCI or pre-MCI comprising primers and/or probes specific for one or more pairs of miRNAs selected from the group consisting of miR-323-3p/miR-127-3p, miR-323-3p/miR-433, miR134/miR-370, miR-335-5p/miR-7, miR-134/miR-410, miR-134/miR-127-3p, miR-335-5p/miR-9, miP-132/miR-451, miR-323-3p/miR-370; miR-132/miR-9, and miR-135a/miR-9.

5. A kit for detecting MCI or pre-MCI comprising primers and/or probes specific for one or more pairs of miRNAs selected from the group consisting of miR-323-3p/miR-433, miR-335-5p/miR-7, miR-134/miR-410, miR-335-5p/miR-9, miP-132/miR-451, and miR-135a/miR-9.

6. A kit for detecting MCI or pre-MCI comprising primers and/or probes specific for one or more miRNA pair combinations selected from the group consisting of miR-323-3p/miR-433+miR-323-3p/miR-127-3p; miR-134/miR-127-3p+miR-323-3p/miR-433+miR-323-3p/miR-127-3p+miR-323-3p/miR-370; miR-134/miR-370+miR-323-3p/miR-433+miR-323-3p/miR-127+miR-323-3p/370; miR-323-3p/370+miR-323-3p/miR-433+miR-134/miR-370+miR-335-5p/miR-9; miR-132/miR-9+miP-132/miR-451+miR-335-5p/miR-7; miR-132/miR-9+miR-135a/miR-9+miR-335-5p/miR-7; miR-134/miR-410+miR-323-3p/miR-127-3p; miR-134/miR-410+miR-323-3p/miR-127-3p.

7. A kit for detecting Alzheimer's disease (AD) comprising primers and/or probes specific for (i) one or more miRNA selected from the group consisting of miR-7, miR-107, miR-125b, miR-127, miR-128a, miR-204, miR-29a, miR-323-3p, miR-329, miR-335-5p, miR-382, miR-433, miR-9*, miR-99b, and miR-491, and (ii) one or more miRNA selected from the group consisting of let-7e, miR-128a, miR-146a, miR-16, miR-181a, miR-29a, miR-411, miR-874, and miR-451.

8. A kit for detecting AD comprising primers and/or probes specific for one or more pairs of miRNAs selected from the group consisting of miR-329/miR-181a, miR-99b/miR-181a, miR-99b/let-7e, miR-107/miR-146a, miR-9*/miR-874, miR-7/miR-16, miR-329/miR-874, miR-329/let-7e, miR-329/miR-146a, miR-433/miR-181a, miR-107/miR-181a, miR-99b/miR-874, miR-7/miR-874, miR-125b/miR-874, miR-107/let-7e, miR-7/miR-451, miR-204/miR-874, miR-491/let-7e, miR-29a/miR-874, miR-323-3p/let-7e, miR-382/let-7e, miR-127/miR-411, miR-335-5p/miR-181a, miR-9*/miR-146a, miR-128a/miR-181a, and miR-128a/miR-146a.

9. A kit for detecting AD comprising primers and/or probes specific for one or more miRNA pair combinations selected from the group consisting of miR-107/miR-146a+miR-9*/miR-155, miR-99b/miR-874+miR-9*/miR-155, miR-9*/miR-16+miR-7/miR-874, miR-329/miR-181a+miR-9*/miR-16+miR-7/miR-874, miR-107/miR-181a+miR-9*/miR-16+miR-7/miR-874, miR-107/miR-146a+miR-9*/miR-16+miR-7/miR-874, miR-99b/miR-181a+miR-9*/miR-874+miR-7/miR-16, and miR-7/miR-451+miR-204/miR-874+miR-491/let-7e.

10. A kit for determining if a patient is at risk of progressing to Alzheimer's Disease (AD) comprising primers and/or probes specific for one or more pairs of miRNAs selected from the group consisting of miR-181a/miR-370, miR-335-5p/miR-370, miR-181a/let-7e, miR-135a/miR-370, miR-132/miR-370, miR-128a/miR-370, miR-128a/let-7e, miR-107/miR-370, miR-410/miR-370, miR-410/miR-433, miR-411/miR-370, miR-382/miR-370, miR-323-3p/miR-370, miR-323-p/miR-370, miR-127/miR-370, miR-127/miR-370, miR-134/miR-370, and miR-433/miR-370.

11. A kit for determining if a patient is at risk of progressing to Alzheimer's Disease (AD) comprising primers and/or probes specific for one or more miRNA pair combinations selected from the group consisting of miR-410/miR-370+miR-181a/miR-370+miR-127/miR-370+miR-128a/let-7e; miR-323-3p/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370.

12. A kit for determining if a patient is at risk of progressing to Alzheimer's Disease (AD) comprising primers and/or probes specific for one or more miRNA pair combinations selected from the group consisting of miR-410/miR-370+miR-181a/miR-370+miR-128a/let-7e; miR-410/miR-370+miR-127/miR-370+miR-128a/let-7e; miR-323-3p/ miR-370+miR-181a/miR-370+miR-128a/let-7e; miR-323-3p/miR-370+miR-127/miR-370+miR-128a/let-7e; miR-323-3p/miR-370+miR-127/miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; and miR-181a/miR-370+miR-127/miR-370+miR-128a/let-7e; miR-410/miR-433+miR-127/miR-370+miR-128a/let-7e.

13. A kit for detecting Parkinson's disease (PD) comprising primers and/or probes specific for (i) one or more miRNA selected from the group consisting of miR-7, let-7e, miR-127, miR-128a, miR-155, miR-181a, miR-323-3p, miR-335-5p, miR-9*, miR-99b, miR-491, and miR-495, and (ii) one or more miRNA selected from the group consisting of let-7e, miR-125b, miR-128a, miR-138, miR-146a, miR-155, miR-181a, miR-204, miR-218, miR-29a, miR-31, miR-338-3p, miR-382, miR-411, miR-874, miR-9, miR-129-3p, and miR-132.

14. A kit for detecting PD comprising primers and/or probes specific for one or more pairs of miRNAs selected from the group consisting of miR-9*/miR-31, miR-9*/miR-138, miR-9*/miR-218, miR-9*/miR-129-3p, miR-9*/miR-874, miR-9*/miR-204, miR-9*/miR-29a, miR-99b/miR-31, miR-99b/miR-138, miR-99b/miR-218, miR-99b/miR-129-3p, miR-99b/miR-874, miR-99b/miR-125b, miR-99b/miR-204, miR-99b/miR-338-3p, miR-99b/miR-29a, miR-99b/let-7e, miR-99b/miR-9, miR-99b/miR-146a, miR-127/miR-411, miR-491/miR-138, miR-128a/miR-138, miR-128a/miR-874, miR-335-5p/miR-138, miR-181a/miR-874, miR-155/miR-31, miR-155/miR-874, let-7e/miR-31, let-7e/miR-874, miR-491/miR-138, miR-491/miR-204, miR-491/miR-31, miR-491/miR-874, miR-7/miR-129-3p, miR-7/miR-874, miR-127/miR-382, miR-495/miR-382, miR-323-3p/miR-411, miR-9*/miR-132, and miR-99b/miR-132.

15. A kit for detecting PD comprising primers and/or probes specific for one or more miRNA pair combinations selected from the group consisting of miRNA pair combinations selected from the group consisting of miR-9*/miR-31+miR-99b/miR-874, miR-99b/miR-874+miR-127/miR-411, miR-491/miR-874+miR-7/miR-129-3p, miR-127/miR-382+miR-128a/let-7e, miR-9*/miR-874+miR-99b/miR-874+miR-127/miR-411, miR-9*/miR-31+miR-99b/miR-874+miR-127/miR-411, miR-9*/miR-129-3p+miR-127/miR-411+miR-491/miR-138, miR-9*/miR-129-3p+miR-99b/miR-874+miR-127/miR-411, and miR-9*/miR-874+miR-127/miR-411+miR-128a/miR-138.

16. A kit for detecting frontotemporal dementia (FTD) comprising primers and/or probes specific for (i) one or more miRNA selected from the group consisting of miR-7, miR-128a, miR-323-3p, miR-335-5p, miR-338-3p, miR-9*, miR-99b, and miR-491, and (ii) one or more miRNA selected from the group consisting of let-7e, miR-125b, miR-146a, miR-155, miR-181a, miR-31, miR-874, and miR-9.

17. A kit for detecting FTD comprising primers and/or probes specific for one or more pairs of miRNAs selected from the group consisting of miR-9*/miR-181a, miR-9*/miR-874, miR-9*/miR-125b, miR-9*/let-7e, miR-9*/miR-155, miR-99b/miR-181a, miR-99b/let-7e, miR-335-5p/let-7e, miR-128a/miR-181a, miR-9*/miR-31, miR-9*/miR-146a, miR-9*/miR-9, miR-323-3p/miR-134, miR-338-3p/miR-181a, miR-491/let-7e, miR-128a/miR-874, miR-128a/let-7e, miR-7/miR-874, miR-7/miR-125b, miR-338-3p/let-7e, miR-335-5p/miR-181a, miR-335-5p/miR-9, and miR-335-5p/miR-146a.

18. A kit for detecting FTD comprising primers and/or probes specific for one or more miRNA pair combinations selected from the group consisting of miR-9*/let-7e+miR-335-5p/let-7e, miR-9*/miR-155+miR-99b/let-7e, miR-7/miR-874+miR-128a/let-7e, miR-99b/let-7e+miR-335-5p/let-7e+miR-128a/miR-181a, miR-9*/let-7e+miR-128a/miR-874, miR-9*/let-7e+miR-7/miR-451+miR-335-5p/let-7e, miR-9*/let-7e+miR-335-5p/let-7e+miR-128a/miR-874, miR-9*/miR-9+miR-99b/let-7e+miR-335-5p/let-7e, and miR-335-5p/miR-181a+miR-335-5p/miR-146a+miR-335-5p/miR-9.

19. A kit for detecting amyotrophic lateral sclerosis (ALS) comprising primers and/or probes specific for (i) one or more miRNA selected from the group consisting of miR-7, miR-181a, miR-206, miR-335-5p, miR-9*, and miR-99b, and (ii) one or more miRNA selected from the group consisting of let-7e, miR-125b, miR-128a, miR-138, miR-155, miR-16, miR-204, miR-218, miR-29a, miR-31, miR-338-3p, miR-874, miR-9, miR-129-3p, and miR-451.

20. A kit for detecting ALS comprising primers and/or probes specific for one or more pairs of miRNAs selected from the group consisting of miR-206/miR-31, miR-206/miR-129-3p, miR-206/miR-138, miR-206/miR-874, miR-206/miR-125b, miR-206/miR-204, miR-206/miR-29a, miR-206/miR-155, miR-206/miR-338-3p, miR-206/miR-16, miR-206/miR-451, miR-206/miR-218, miR-99b/miR-9, miR-99b/miR-155, miR-99b/miR-338-3p, miR-9*/miR-129-3p, miR-99b/miR-155, miR-99b/let-7e, miR-181a/miR-338-3p, miR-335-5p/miR-338-3p, miR-7/miR-31, miR-7/miR-129-3p, miR-9*/miR-129-3p, miR-9*/miR-338-3p, miR-99b/miR-338-3p, miR-99b/miR-128a, and miR-335-5p/let-7e.

21. A kit for detecting ALS comprising primers and/or probes specific for one or more miRNA pair combinations selected from the group consisting of miR-206/miR-31+miR-99b/miR-338-3p, miR-206/miR-138+miR-9*/miR-129-3p, miR-206/miR-31+miR-335-5p/miR-338-3p, miR-206/miR-16+miR-335-5p/miR-338-3p, miR-9*/miR-129-3p+miR-99b/miR-338-3p, miR-206/miR-204+miR-206/miR-218+miR-335-5p/miR-338-3p, miR-206/miR-204+miR-206/miR-218+miR-9*/miR-129-3p, miR-206/miR-338-3p+miR-99b/miR-129-3p+miR-335-5p/miR-338-3p, miR-206/miR-338-3p+miR-99b/miR-155+miR-335-5p/miR-338-3p and miR-181a/miR-338-3p+miR-335-5p/miR-338-3p+miR-7/miR-31+miR-7/miR-129-3p.

22. A kit for differentiating Alzheimer's disease (AD) and frontotemporal dementia (FTD) comprising primers and/or probes specific for one or more pairs of miRNAs selected from the group consisting of miR-125b/miR-29a, miR-125b/miR-874, miR-107/miR-335-5p, miR-155/miR-29a, miR-329/miR-874, miR-329/miR-181a, miR-329/miR-411, miR-7/miR-16, miR-451/miR-16, miR-155/miR-335-5p, and let-7e/miR-335-5p.

23. A kit for differentiating Alzheimer's disease (AD) and frontotemporal dementia (FTD) comprising primers and/or probes specific for one or more miRNA pair combinations selected from the group consisting of miR-125b/miR-29a+miR-107/miR-335-5p+miR-155/miR-29a, miR-125b/miR-29a+miR-125b/miR-874+miR-107/miR-335-5p, miR-125b/miR-874+miR-107/miR-335-5p+miR-155/miR-29a, miR-329/miR-411+miR-329/miR-16, miR-329/miR-874+miR-329/miR-411, miR-329/miR-411+miR-329/miR-16+miR-7/miR-16, and miR-451/miR-16+miR-155/miR-335-5p+let-7e/miR-335-5p.

24. A kit for differentiating Alzheimer's disease (AD) and Parkinson's disease (PD) comprising primers and/or probes specific for one or more pairs of miRNAs selected from the group consisting of miR-31/miR-9*, miR-31/miR-99b, miR-31/miR-16, miR-31/miR-29a, miR-138/miR-9*, miR-138/miR-99b, miR-138/miR-181a, miR-138/miR-491-5p, miR-138/miR-335-5p, miR-138/miR-128a, miR-138/miR-146a, miR-138/let-7e, miR-138/miR-16, miR-138/miR-29a, miR-129-3p/miR-9*, miR-129-3p/miR-99b, miR-129-3p/miR-335-5p, miR-129-3p/miR-146a, miR-129-3p/miR-16, miR-129-3p/miR-29a, miR-125b/miR-9*, miR-125b/miR-99b, miR-125b/miR-181a, miR-125b/miR-491-5p, miR-125b/miR-335-5p, miR-125b/miR-128a, miR-125b/miR-146a, miR-125b/let-7e, miR-218/miR-9*, miR-218/miR-16, miR-204/miR-9*, miR-204/miR-99b, miR-204/miR-146a, miR-338-3p/miR-99b, miR-107/miR-99b, and miR-107/miR-491-5p.

25. A kit for differentiating Alzheimer's disease (AD) and Parkinson's disease (PD) comprising primers and/or probes specific for one or more miRNA pair combinations selected from the group consisting of miR-31/miR-16+miR-129-3p/miR-9*+miR-204/miR-99b, miR-129-3p/miR-16+miR-125b/miR-181a+miR-204/miR-9*, miR-31/miR-99b+miR-129-3p/miR-16+miR-204/miR-9*, miR-31/miR-16+miR-125b/miR-181a+miR-204/miR-9*, and miR-31/miR-16+miR-129-3p/miR-335-5p+miR-204/miR-9*.

26. A kit for differentiating Alzheimer's disease (AD) and amyotrophic lateral sclerosis (ALS) comprising primers and/or probes specific for one or more pairs of miRNAs selected from the group consisting of miR-329/miR-206, miR-329/miR-9*, miR-329/miR-99b, miR-329/miR-335-5p, miR-329/miR-146a, miR-329/miR-411, miR-31/miR-206, miR-31/miR-16, miR-129-3p/miR-206, miR-129-3p/miR-16, miR-433/miR-206, miR-433/miR-335-5p, miR-125b/miR-206, miR-125b/miR-335-5p, miR-125b/miR-874, miR-323-3p/miR-206, miR-495/miR-206, miR-204/miR-206, miR-127-3p/miR-206, miR-107/miR-206, miR-107/miR-99b, miR-107/miR-335-5p, miR-107/let-7e, miR-107/miR-146a, miR-107/miR-491-5p, miR-138/miR-206, miR-134/miR-206, miR-9/miR-206, miR-155/miR-206, miR-7/miR-206, miR-338-3p/miR-206, miR-29a/miR-206, miR-338-3p/let-7e, miR-433/miR-411, miR-433/miR-382, and miR-127-3p/miR-411.

27. A kit for differentiating Alzheimer's disease (AD) and amyotrophic lateral sclerosis (ALS) comprising primers and/or probes specific for one or more miRNA pair combinations selected from the group consisting of miR-31/miR-206+miR-125b/miR-335-5p, miR-31/miR-206+miR-125b/miR-335-5p+miR-107/miR-335-5p, miR-31/miR-206+miR-125b/miR-335-5p+miR-107/miR-491-5p, miR-125b/miR-335-5p+miR-107/let-7e+miR-138/miR-206, miR-125b/miR-335-5p+miR-107/miR-491-5p+miR-338-3p/miR-206, miR-125b/miR-335-5p+miR-107/let-7e+miR-338-3p/miR-206, miR-125b/miR-335-5p+miR-323-3p/miR-206+miR-107/let-7e, and miR-433/miR-382+miR-127-3p/miR-411.

28. A kit for determining if a patient is at risk of progressing to Alzheimer's Disease (AD) as an $A\beta_{42}$ positive progressor comprising primers and/or probes specific for one or more pairs of miRNAs selected from the group consisting of miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, and miR-135a/miR-410.

29. A kit for determining if a patient is at risk of progressing to Alzheimer's Disease (AD) as an $A\beta_{42}$ positive progressor comprising primers and/or probes specific for one or more miRNA pair combinations selected from the group consisting of miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410.

30. A kit for determining if a patient is at risk of progressing to Alzheimer's Disease (AD) as an $A\beta_{42}$ positive progressor comprising primers and/or probes specific for one or more miRNA pair combinations selected from the group consisting of miR-382/miR-134+miR-135a/miR-181a+miR-323-3p/miR-410, miR-382/miR-134+miR-135a/miR-181a+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, miR-128a/let-7e+miR-370/miR-433+miR-135a/miR-134.

31. A kit for determining if a patient is at risk of progressing to Alzheimer's Disease (AD) as an $A\beta_{42}$ positive progressor comprising primers and/or probes specific for one or more pairs of miRNAs selected from the group consisting of miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, and miR-382/miR-485-5p.

32. A kit for determining if a patient is at risk of progressing to Alzheimer's Disease (AD) as an $A\beta_{42}$ positive progressor comprising primers and/or probes specific for one or more miRNA pair combinations selected from the group consisting of miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p.

33. A kit for determining if a patient is at risk of progressing to Alzheimer's Disease (AD) as an $A\beta_{42}$ positive progressor comprising primers and/or probes specific for one or more miRNA pair combinations selected from the group consisting of miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a/let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, and miR-410/miR-433+miR-323-3p/miR-485-5p+miR-135a/miR-134.

34. A kit for detecting AD and early AD in a male subject comprising primers and/or probes specific for one or more miRNA pair combinations selected from the group consisting of miR-132/miR-433+miR-132/miR-7+miR-874/miR-9, miR-323/miR-485+miR-410/miR-485, and miR-99b/miR-181a+miR-125/miR-874+miR-9*+miR-29a.

35. A kit for detecting AD and early AD in a female subject comprising primers and/or probes specific for one or more miRNA pair combinations selected from the group consisting of miR-135a/miR-433+miR-323/miR-433+miR-323/miR-127, miR-323/miR-433+miR-323/miR-411+miR-128a/miR-7, and miR-99b/miR-181a+miR-9*/miR-874+miR-7/miR-451.

36. A kit for detecting AD in a male subject comprising primers and/or probes specific for the miRNA pair combination of miR-99b/miR-181a+miR-125/miR-874+miR-9*+miR-29a.

37. A kit for detecting AD in a female subject comprising primers and/or probes specific for the miRNA pair combination of miR-99b/miR-181a+miR-9*/miR-874+miR-7/miR-451.

38. A kit for detecting PD in a male subject comprising primers and/or probes specific for the miRNA pair combination of miR-9*/miR-129-3p+miR-99b/miR-146a+miR-9*/miR-204.

39. A kit for detecting PD in a female subject comprising primers and/or probes specific for the miRNA pair combination of miR-9*/miR-29a+miR-99b/miR-874+miR-491/let-7e.

40. A kit for detecting FTD in a male subject comprising primers and/or probes specific for the miRNA pair combination of miR-335-5p/let-7e+miR-99b/let-7e+miR-9*/miR-181a.

41. A kit for detecting FTD in a female subject comprising primers and/or probes specific for the miRNA pair combination of miR-491/let-7e+miR-107/miR-9+miR-28/miR-181a.

42. A kit for detecting ALS in a male subject comprising primers and/or probes specific for the miRNA pair combination of miR-206/miR-155+miR-9*/miR-129-3p+miR-355/miR-338-3p.

43. A kit for detecting ALS in a female subject comprising primers and/or probes specific for the miRNA pair combination of miR-206/miR-7+miR-9*/miR-125b+miR-491/miR-204.

44. A kit for differentiating frontotemporal dementia (FTD) and Parkinson's disease (PD) comprising primers and/or probes specific for one or more pairs of miRNAs selected from the group consisting of miR-218/miR-9*, miR-218/miR-99b, miR-138/miR-99b, miR-138/miR-181a, miR-138/miR-491-5p, miR-31/miR-9*, miR-31/miR-99b, miR-129-3p/miR-9*, miR-129-3p/miR-99b, miR-204/miR-9*, miR-204/miR-99b, miR-338-3p/miR-99b, miR-338-3p/miR-491-5p, miR-338-3p/miR-107, miR-338-3p/let-7e, miR-338-3p/miR-146a, miR-874/miR-99b, miR-125b/miR-99b, miR-29a/miR-99b, miR-323-3p/miR-127-3p, miR-411/miR-127-3p, miR-155/miR-99b, miR-335-5p/miR-99b, and miR-382/miR-134.

45. A kit for differentiating frontotemporal dementia (FTD) and Parkinson's disease (PD) comprising primers and/or probes specific for one or more miRNA pair combinations selected from the group consisting of miR-129-3p/miR-9*+miR-338-3p/miR-491-5p, miR-129-3p/miR-9*+miR-338-3p/miR-99b+miR-323-3p/miR-127-3p, miR-129-3p/miR-9*+miR-338-3p/miR-491-5p+miR-411/miR-127-3p, miR-129-3p/miR-9*+miR-338-3p/miR-491-5p+miR-323-3p/miR-127-3p, miR-204/miR-9*+miR-338-3p/miR-491-5p+miR-323-3p/miR-127-3p, miR-129-3p/miR-9*+miR-29a/miR-99b+miR-323-3p/miR-127-3p, and miR-138/miR-181a+miR-129-3p/miR-9*+miR-411/miR-127-3p.

46. A kit for differentiating frontotemporal dementia (FTD) and amyotrophic lateral sclerosis (ALS) comprising primers and/or probes specific for one or more pairs of miRNAs selected from the group consisting of miR-31/miR-206, miR-138/miR-206, miR-29a/miR-206, miR-129-3p/miR-206, miR-204/miR-206, miR-338-3p/miR-206, miR-338-3p/let-7e, miR-7/miR-206, miR-128a/miR-206, miR-16/miR-206, miR-125b/miR-206, miR-874/miR-206, miR-218/miR-206, miR-29a/miR-155, miR-338-3p/miR-181a, miR-338-3p/miR-335-5p, miR-338-3p/miR-491-5p, miR-338-3p/miR-146a, miR-323-3p/miR-127-3p, and miR-129-3p/miR-9*.

47. A kit for differentiating frontotemporal dementia (FTD) and amyotrophic lateral sclerosis (ALS) comprising primers and/or probes specific for one or more miRNA pair combinations selected from the group consisting of miR-29a/miR-206+miR-338-3p/let-7e, miR-129-3p/miR-206+miR-338-3p/let-7e, miR-204/miR-206+miR-338-3p/let-7e, miR-138/miR-206+miR-338-3p/let-7e, miR-129-3p/miR-206+miR-338-3p/let-7e+miR-125b/miR-206, miR-129-3p/miR-206+miR-338-3p/let-7e+miR-874/miR-206, miR-129-3p/miR-206+miR-338-3p/let-7e+miR-7/miR-206, and miR-338-3p/miR-181a+miR-338-3p/miR-335-5p+miR-323-3p/miR-127-3p.

48. A kit for differentiating Parkinson's disease (PD) and amyotrophic lateral sclerosis (ALS) comprising primers and/or probes specific for one or more pairs of miRNAs selected from the group consisting of miR-329/miR-206, miR-9*/miR-206, miR-433/miR-206, miR-370/miR-206, miR-134/miR-206, miR-323-3p/miR-206, miR-9/miR-206, miR-99b/miR-206, miR-495/miR-206, miR-382/miR-206, miR-491-5p/miR-206, miR-29a/miR-206, miR-411/miR-206, miR-181a/miR-206, miR-155/miR-206, miR-146a/miR-206, miR-7/miR-206, miR-107/miR-204, miR-107/let-7e, miR-107/miR-335-5p, miR-107/miR-146a, miR-128a/miR-874, miR-128a/let-7e, miR-329/miR-382, miR-433/miR-382, and miR-433/miR-411.

49. A kit for differentiating Parkinson's disease (PD) and amyotrophic lateral sclerosis (ALS) comprising primers and/or probes specific for one or more miRNA pair combinations selected from the group consisting of miR-29a/miR-206+miR-7/miR-206, miR-9*/miR-206+miR-7/miR-206, miR-9*/miR-206+miR-155/miR-206+miR-7/miR-206, miR-107/miR-204+miR-107/miR-146a+miR-128a/miR-874, miR-107/miR-204+miR-128a/miR-874+miR-128a/let-7e, miR-107/miR-335-5p+miR-128a/miR-874+miR-128a/let-7e, miR-107/miR-204+miR-107/miR-146a+miR-128a/let-7e, and miR-329/miR-382+miR-433/miR-382+miR-433/miR-411.

Any of the above kits can further comprise miRNA isolation and/or purification means and/or instructions for use.

These and other aspects of the present invention will be apparent to those of ordinary skill in the art in the following description and claims.

DETAILED DESCRIPTION OF THE INVENTION

Figure 1A:
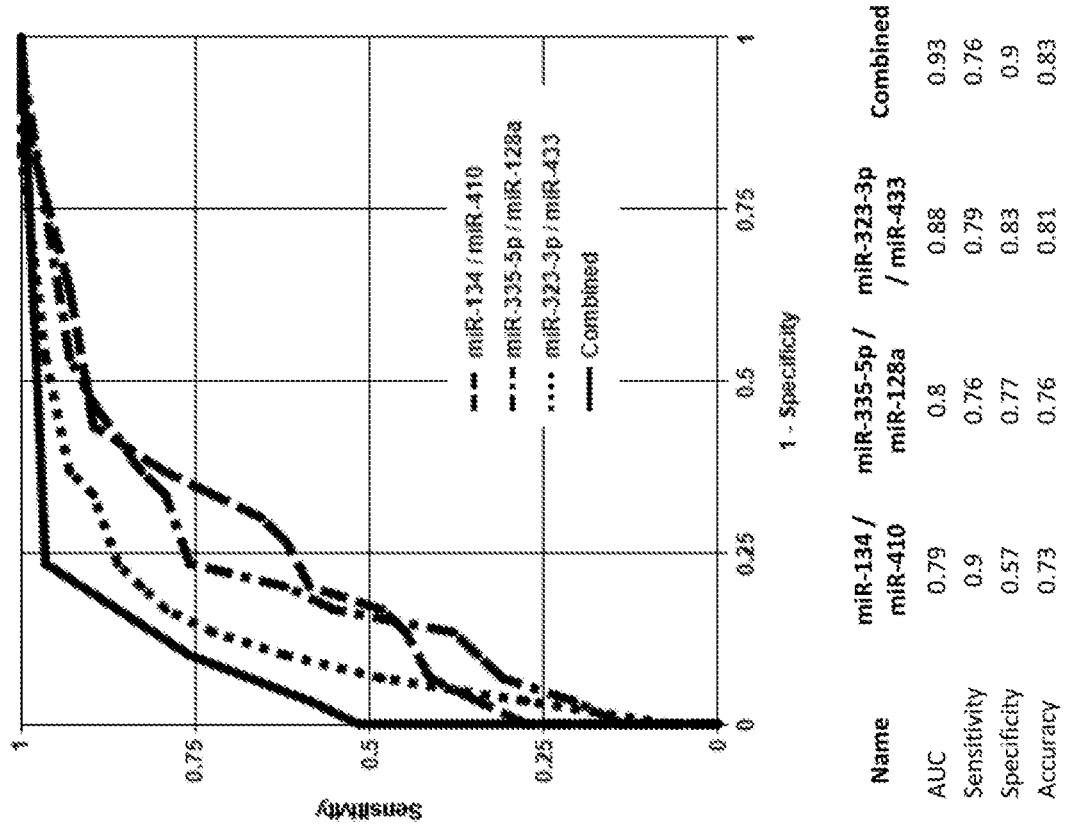
FIGS. 1A-1C present Receiver-Operating Characteristics (ROC) curve analysis of differentiation between early AD (CDR>0, Aβ-42 positive subjects) and age-matched controls (CDR 0, Aβ-42 negative subjects). Three different miRNA pair combinations are shown for each of cohort pairs: 1A: male and female subjects combined; 1B: male subjects; 1C: female subjects. The areas under the ROC curve (AUC) are reported in Tables under ROC curves. Sensitivity, specificity and accuracy are calculated for the "cutoff" point with maximal accuracy.
Figure 1A:
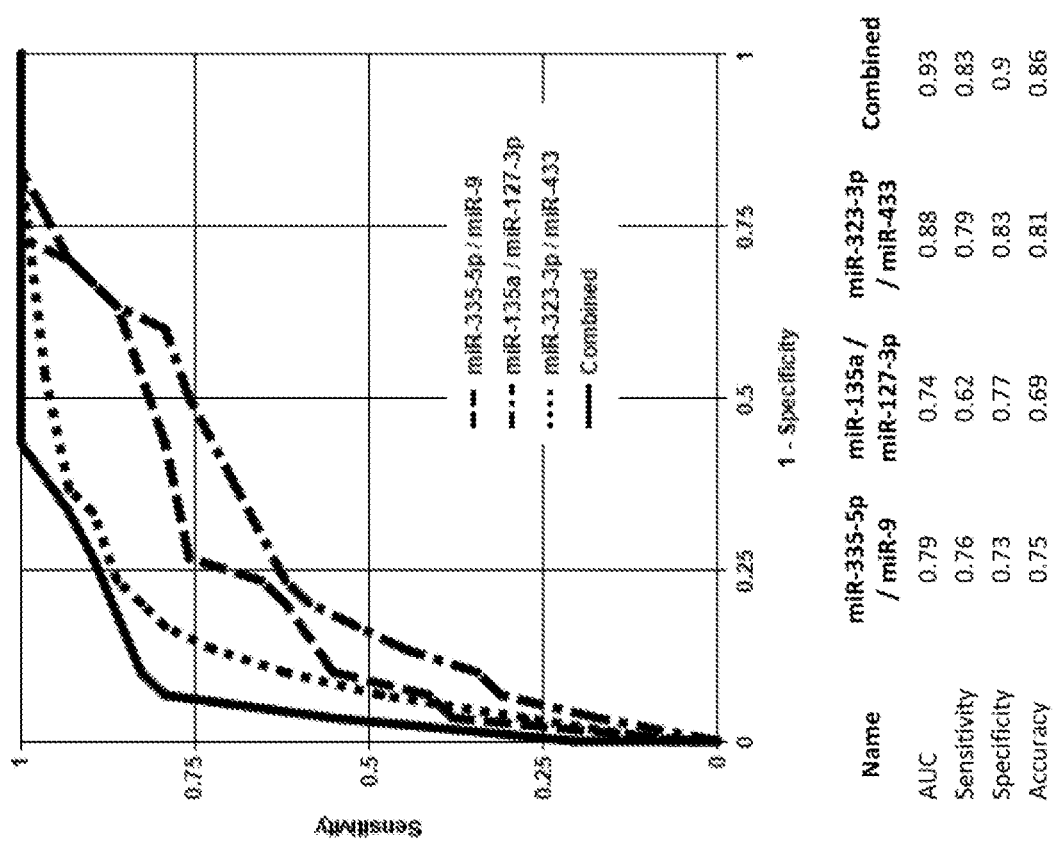
Figure 1A:
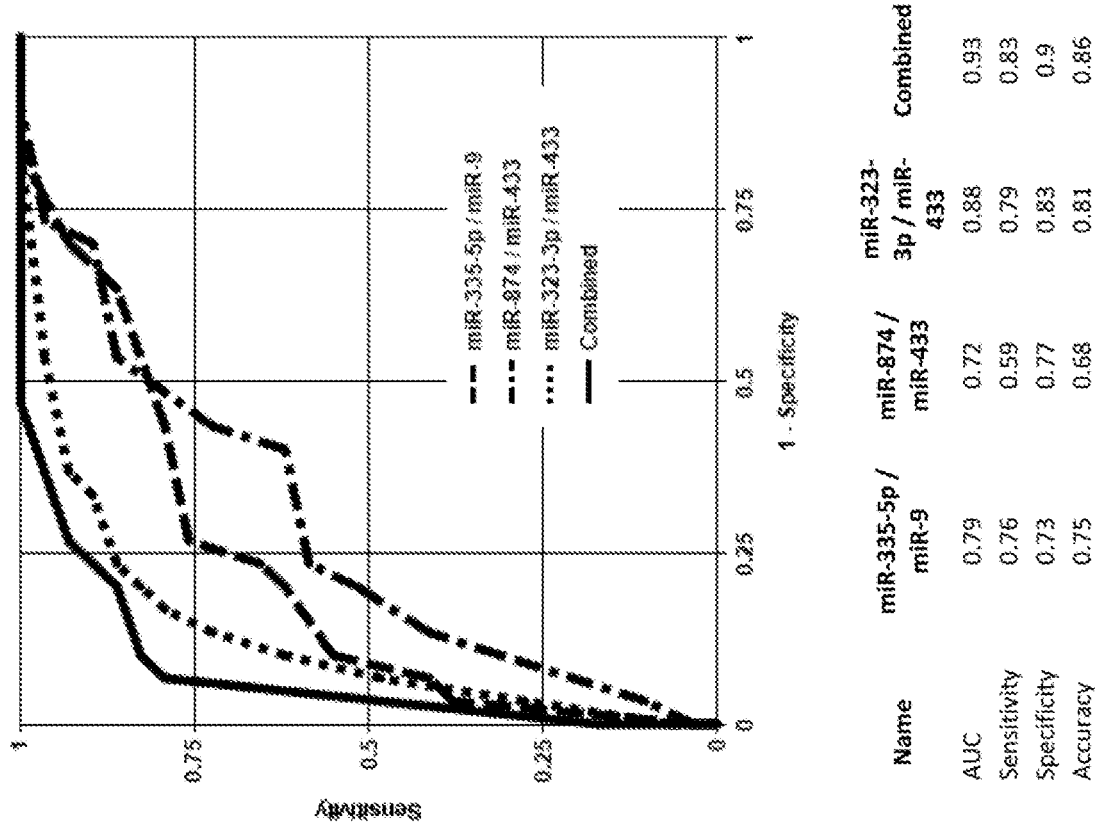
Figure 1B:
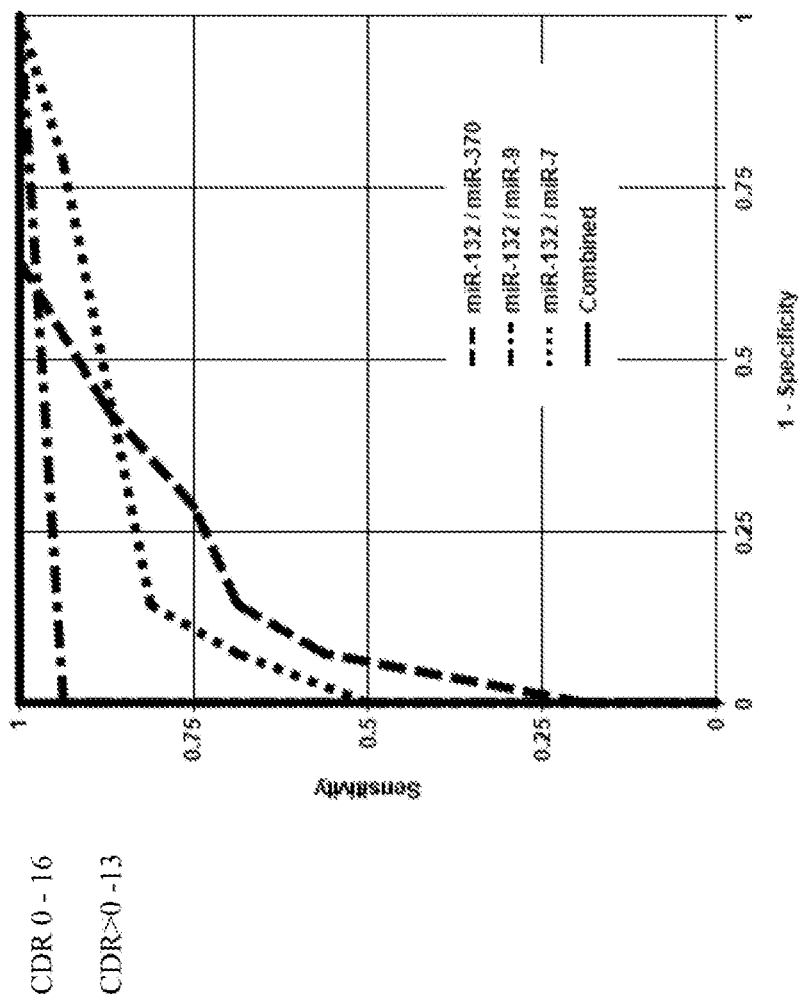
Figure 1B:
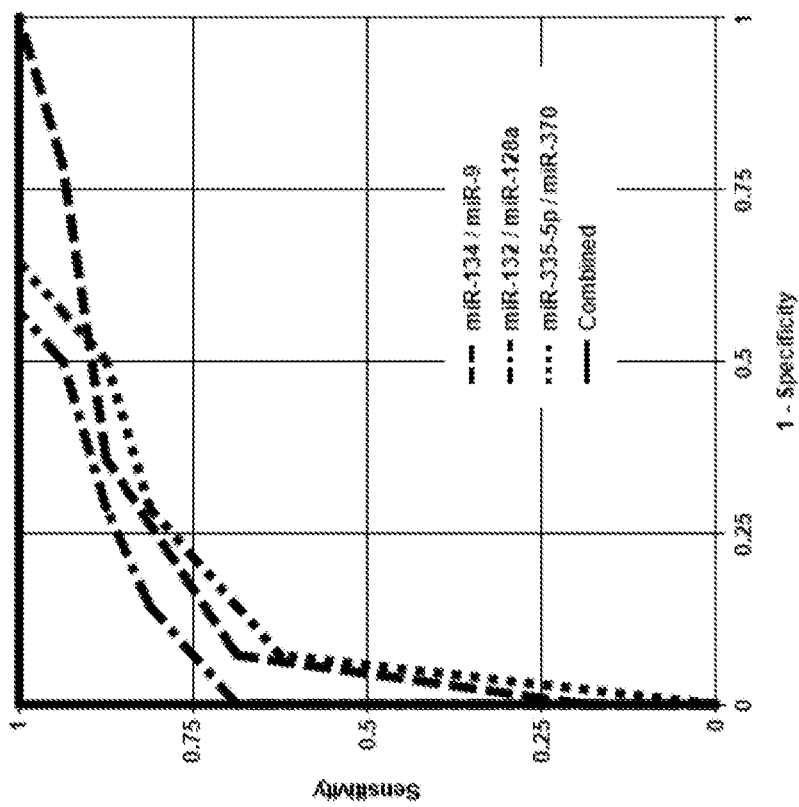
Figure 1B:
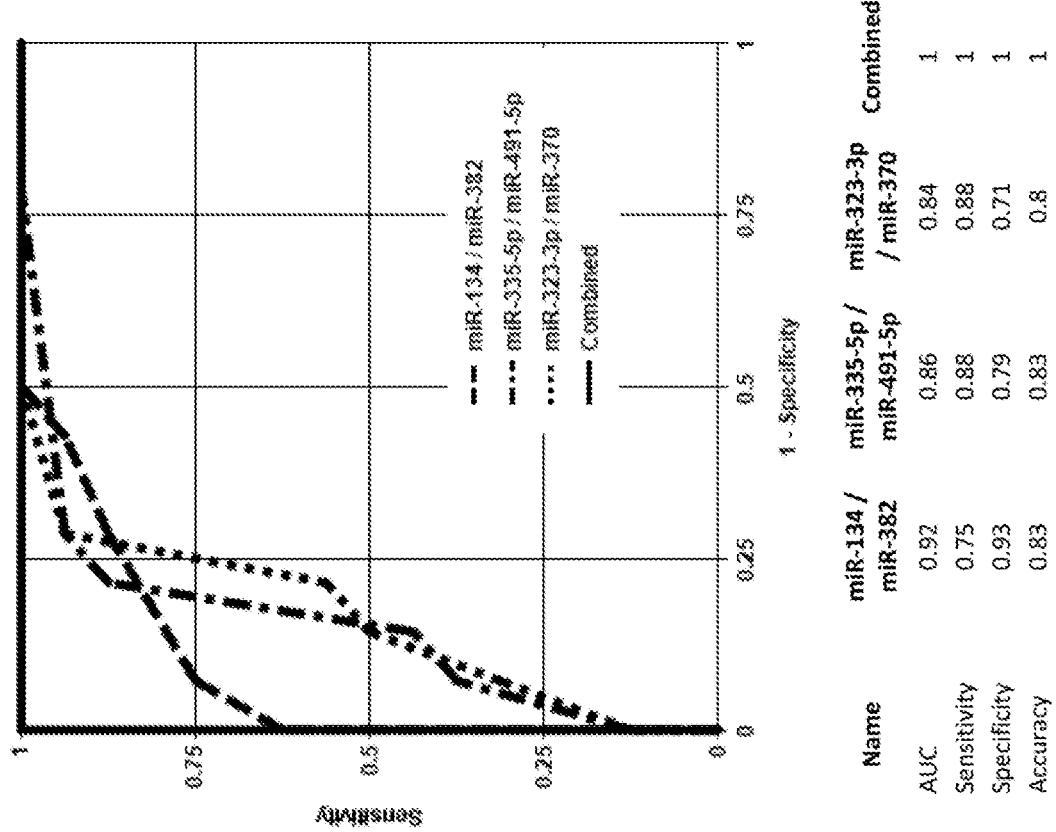
Figure 1C:
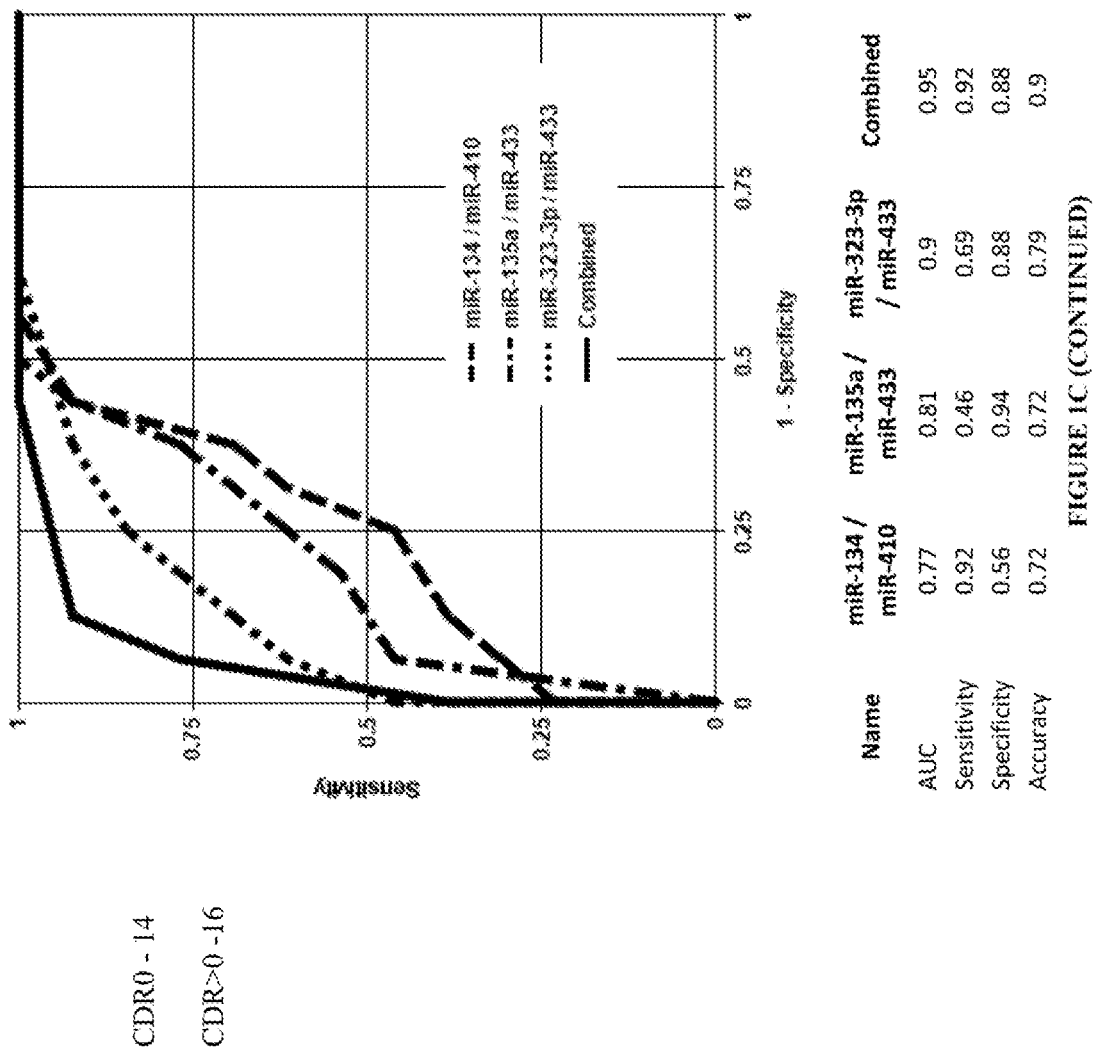
Figure 1C:
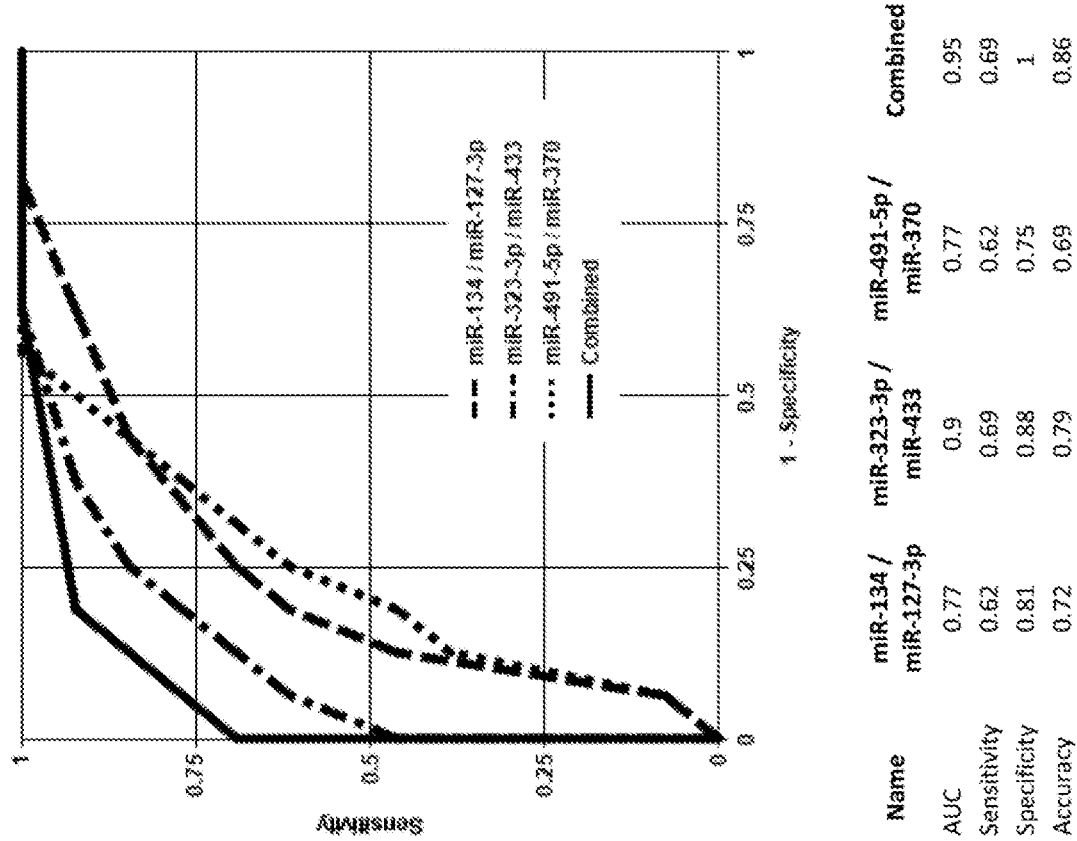
Figure 1C:
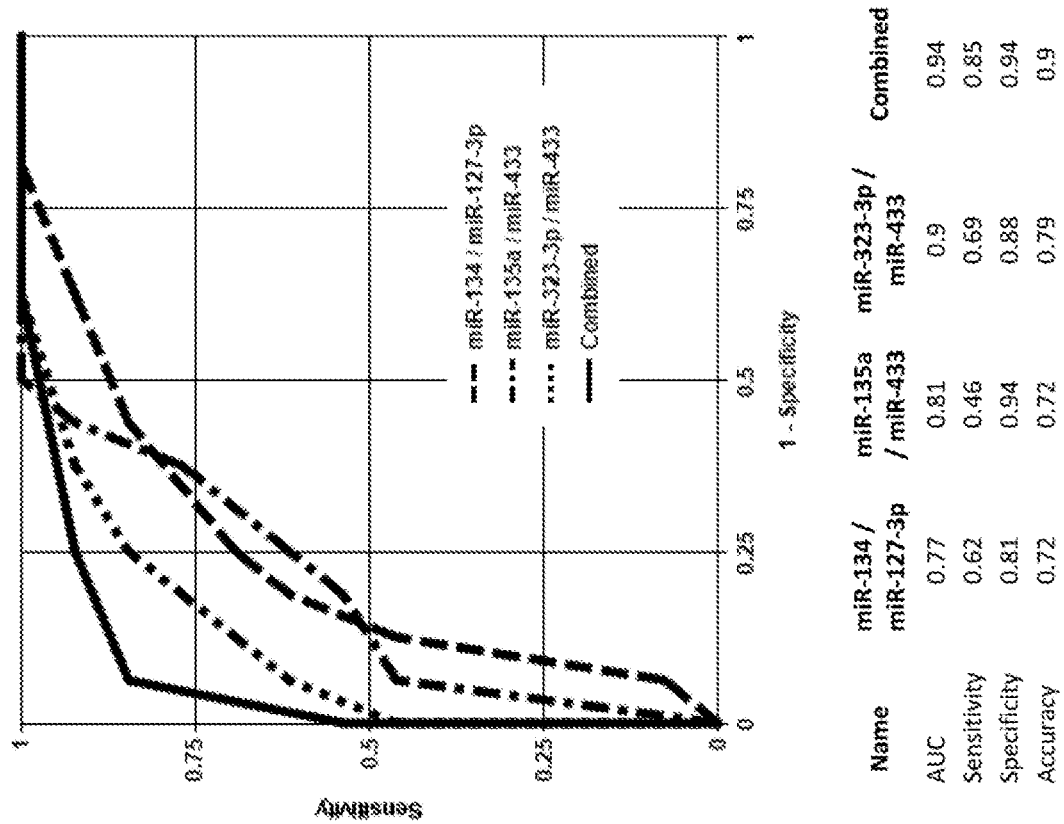
Figure 2A:
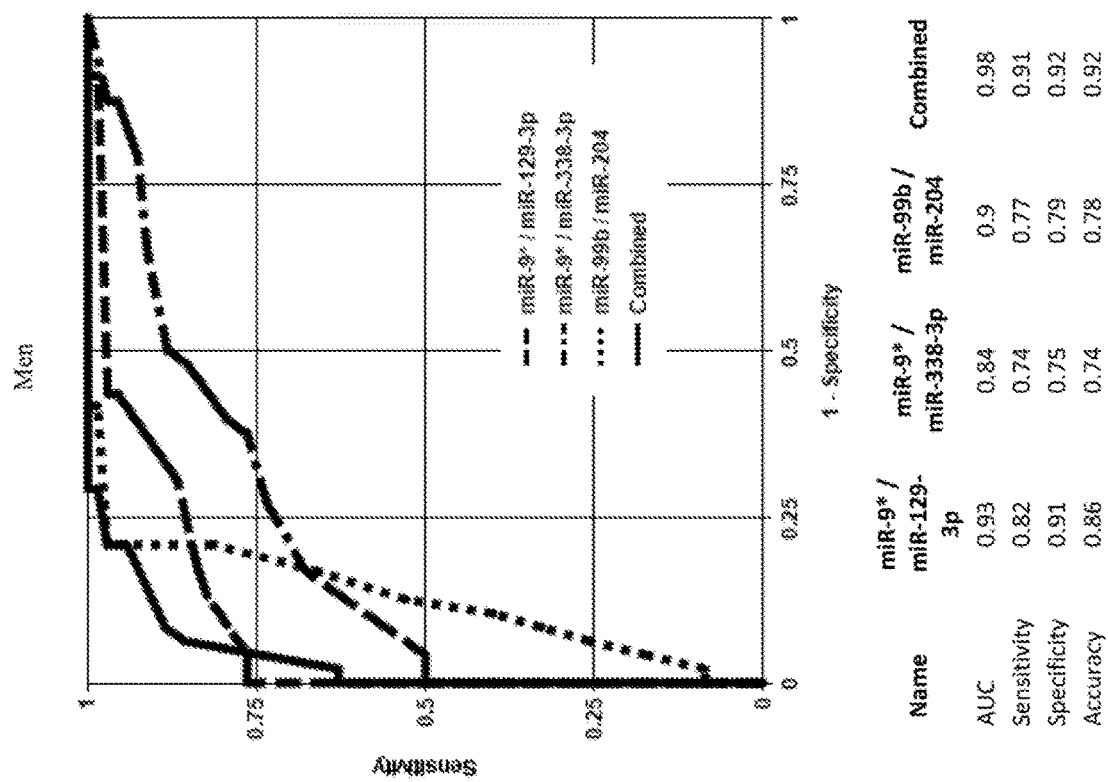
FIG. 2A-2B present Receiver-Operating Characteristics (ROC) curve analysis of differentiation between subjects with different NDs and age-matched controls (AMC). Three different cohort pairs (men and women combined; men only; and women only) are presented for 4 ND versus AMC: AD, FTD, PD and ALS. The areas under the ROC curve (AUC) are reported in Tables under ROC curves. Sensitivity, specificity and accuracy are calculated for the "cutoff" point with maximal accuracy.
Figure 2A:
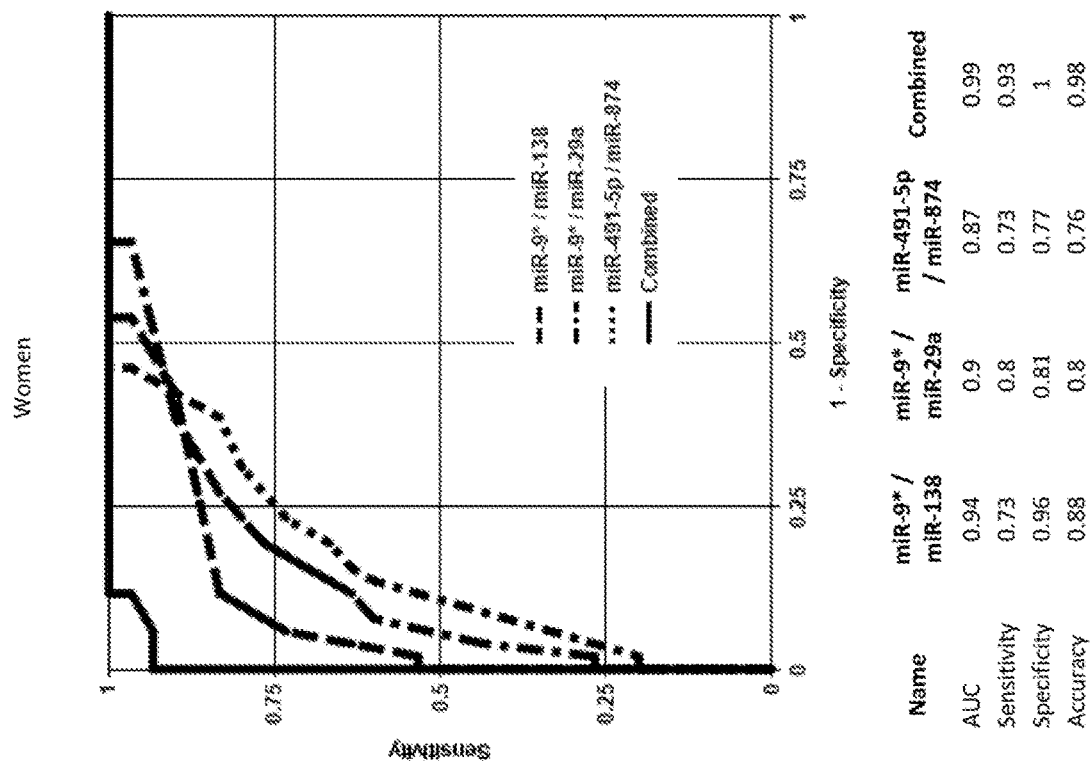
Figure 2B:
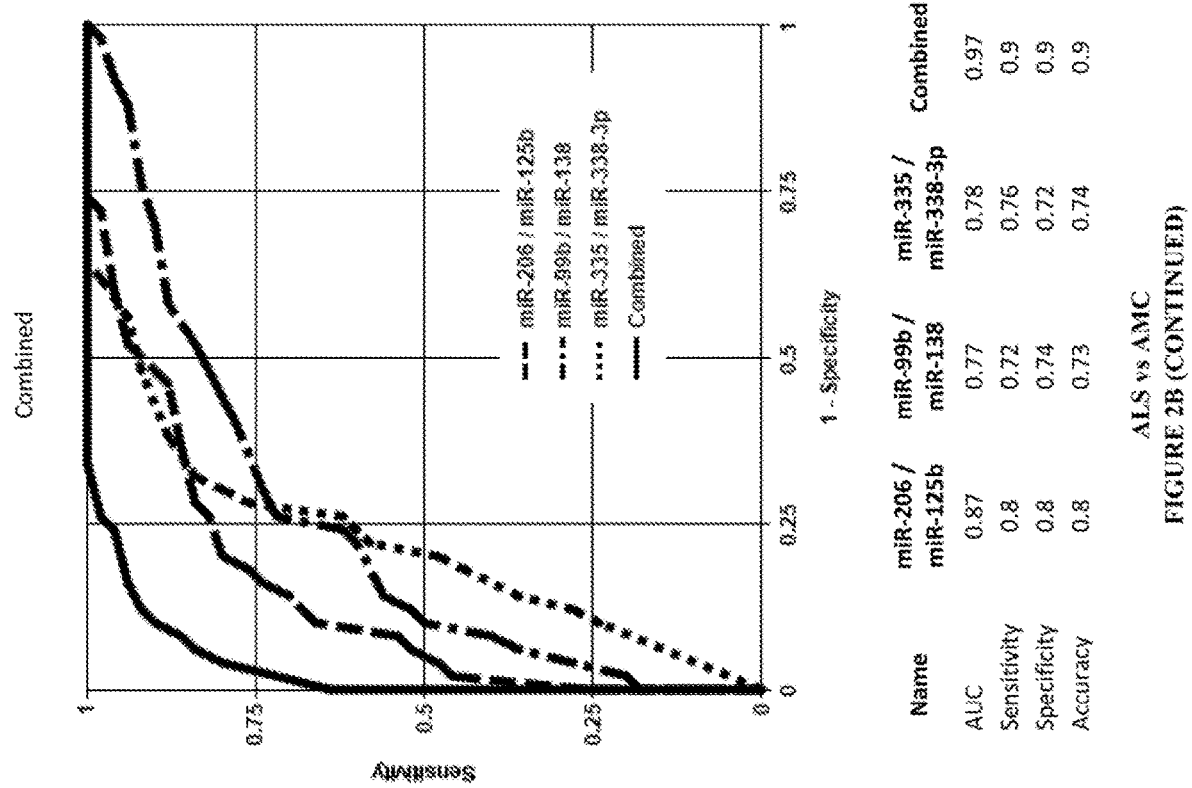
Figure 2B:
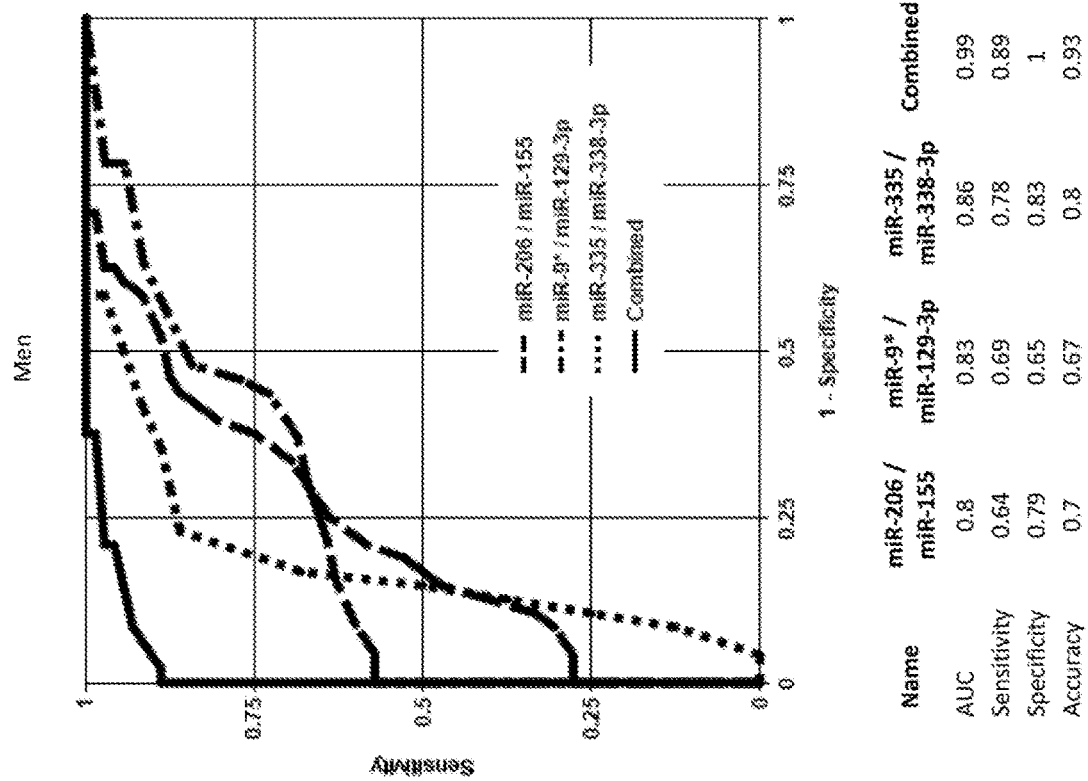
Figure 2B:
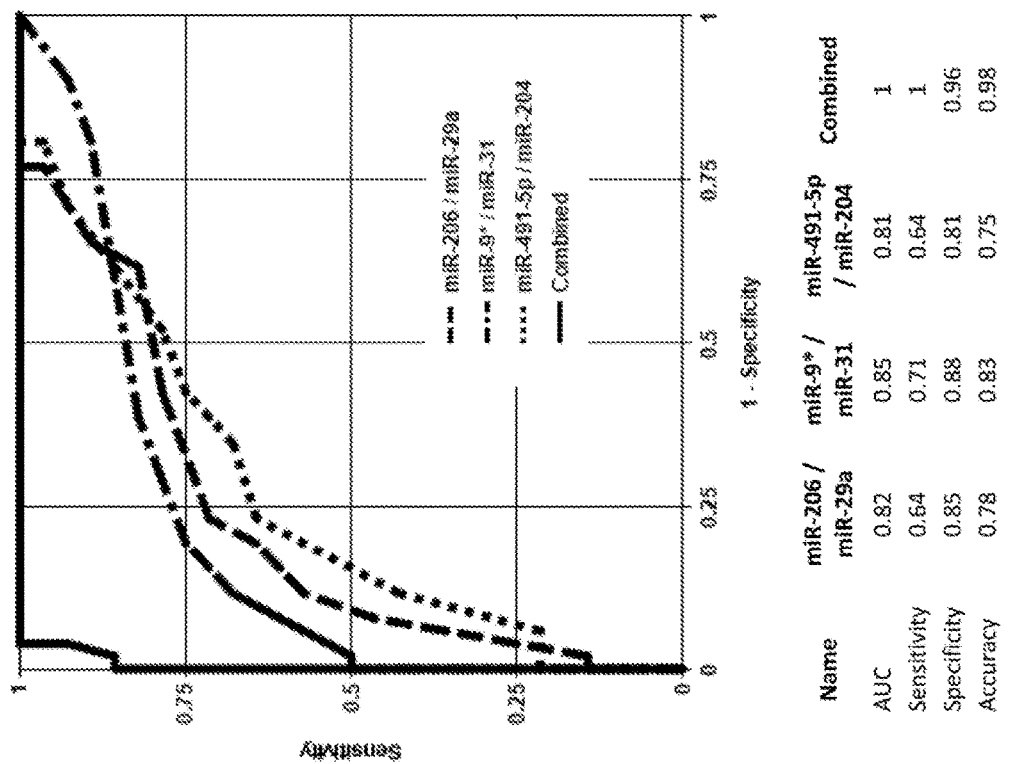

Taken together, the present invention is based on the following ideas and findings made by the present inventors:

(1) changes in concentrations of circulating miRNAs enriched in the brain, and more specifically in brain areas involved in a particular pathology at its different stages of development, are more likely to reflect associated pathologic processes in the brain than ubiquitous miRNAs or miRNAs enriched in brain areas not involved in this specific pathology;

(2) synapse and/or neurite miRNAs should be analyzed, because dysfunction and destruction of neurites and synapses is characteristic of NDs and their different stages of development, and therefore, can affect expression and secretion of these miRNAs;

(3) to compensate for processes unrelated directly to a particular pathology, e.g., changes in blood supply or blood-brain barrier permeability, the present inventors have developed the "biomarker miRNA pair" approach normalizing miRNAs enriched in neurons of damaged brain area(s) by other brain-enriched miRNAs, such as, e.g., (i) miRNAs enriched in a brain area(s) which is not affected by the ND which is being diagnosed, or (ii) miRNAs enriched in a brain cell type which is not affected by the ND which is being diagnosed, or (iii) miRNAs enriched in the same brain area as the biomarker miRNA, but its expression and/or secretion change differently than expression and/or secretion of the biomarker miRNA during development of the ND which is being diagnosed;

(4) high correlation of plasma concentrations of miRNAs used as numerator and denominator in a biomarker miRNA pair is very important for its sensitivity and specificity.

The present invention is based on analysis of the ratios of the levels for pairs of circulating cell-free miRNA in bodily fluids, wherein both miRNA in the pair are brain-enriched, and either (i) are enriched in certain brain areas, which are (for one miRNA in the pair) or are not (for the other miRNA in the pair) affected by the ND (e.g., by being involved in ND development), or (ii) are enriched in different cell types (e.g., neurons and glial cells), or (iii) are enriched in the same brain area but whose expression and/or secretion change differently due to ND development. Brain-enriched miRNAs which are particularly useful as numerators in the biomarker miRNA pairs of the invention include neuronal miRNAs present in neurites and synapses (i.e., synapse and/or neurite miRNAs), whose normal functioning suffers in AD, PD, FTD, ALS or other NDs. Since various NDs are characterized by neuronal pathology in different brain areas such biomarker miRNA pairs can be used for differentiating those pathologies from each other independent of their clinical symptoms, if any. In addition, discovered biomarker miRNA pairs, reflecting important events in pathology development, could be used for patient selection and stratification for clinical trials, early patient treatment, disease and treatment monitoring as well as for drug screening. Due to evolutionary conservation of miRNAs the same biomarker miRNA pairs may be also used in animal models for preclinical phase of drug development.

Use of brain-enriched miRNA in the methods of the invention significantly increases chances that changes of their levels in bodily fluids are caused by brain pathology, and changes in bodily fluid concentration of miRNA enriched in a particular brain area should be indicative of pathology in that brain part. For example, changes in levels of midbrain- or cortex-enriched miRNA would be associated with PD, reflecting synapse and neuronal dysfunctions in these brain areas. In addition, concentrations of brain-enriched miRNA in blood cells are low, which decreases contamination of plasma and serum by miRNA leakage during purification of these bodily fluids. During disease progression pathology spreads to new brain areas, and this phenomenon can be used for disease monitoring. For example, circulating synaptic miRNAs of hippocampus are good markers of asymptomatic pre-MCI or MCI stages of AD but with disease progression and cortex involvement in pathology cortex synaptic miRNAs become better biomarkers.

The concentrations of miRNAs detected in bodily fluids depend on many biological and technical factors. Biological factors include miRNA levels in various tissues, intensity of secretion and excretion into extracellular space, forms of circulating miRNAs (exosomes and other vesicles, complexes with proteins and lipids) affecting their ability to cross various barriers, e.g. blood-brain, placental, and kidney barriers, and miRNA stability and half-life in the blood-stream. Technical factors include variability in methods of bodily fluid collection and storage, methods used for miRNA extraction, and presence in bodily fluids of various factors affecting miRNA purification and quantitation. As a consequence, the importance of miRNA normalization is broadly recognized (Meyer et al., Biotechnol. Lett. 2010; 32: 1777-1788). At the same time, no single normalization method is commonly accepted.

The present invention is based on the use of brain-enriched biomarker miRNA pairs instead of (or in addition to) normalization per ubiquitous RNA or an average of numerous miRNAs. The use of brain-enriched biomarker miRNA pairs (one as a numerator and another one as a denominator in a ratio) has several advantages. First, any pathology is usually associated with up-regulation of some miRNAs and down-regulation of other miRNAs, thus considering miRNA pairs of up- and down-regulated miRNAs may increase test sensitivity and specificity. Second, the use of a pair of brain-enriched miRNAs, rather than one brain-enriched miRNA, decreases potential overlap with pathologies of other organs. Third, one can expect that changes unrelated to or non-specific for a pathology of interest, such as, e.g., changes in blood supply, blood-brain permeability and others, will be better compensated for by using the pair of miRNAs enriched in the same organ. In addition, changes in relative concentrations of miRNAs enriched in different brain areas or different cell types (e.g., neurons and glial cells) may be an indicator of disease progression.

Another innovative aspect of the present invention is the use of probabilistic approach in addition to or instead of calculating ratios of miRNA concentrations in plasma. The use of integral distribution curves, which characterize probabilities of a subject belonging to control or having a pathology has such advantages as better definition of diagnostic uncertainty zone, simplicity of combining biomarkers of different nature (e.g., protein levels, imaging techniques and miRNA levels) and others.

In the present invention, since various miRNA are involved in regulation of different processes, combination of several miRNA pairs were also tested to find out the groups of miRNA pairs providing the highest test accuracy (i.e., sensitivity and specificity).

Definitions

As used herein, the term "brain-enriched" means that miRNA concentration in brain is at least 4-5 times higher than in other organs.

As used herein in connection with miRNA enrichment in a certain area of the brain, the term "enriched" means that miRNA concentration in said area of the brain is higher (preferably, at least 2-fold higher, more preferably at least 5-fold higher, most preferably at least 10-fold higher) than in brain in general. The term refers to the difference in concentrations within the brain areas (e.g., as measured using qRT-PCR).

Within the meaning of the present invention, the term "synapse and/or neurite miRNA" refers to miRNA which (i) is "brain-enriched" and (ii) is present in a synapse and/or neurite (i.e., axon and/or dendrite and/or spine). To be useful in the methods of the present invention, synapse and/or neurite miRNAs should be detectable in bodily fluids as a result of their release from neurons (e.g., due to secretion, neurite/synapse destruction or neuronal death).

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

The term "normalizer miRNA" as used herein refers to miRNA which is used for normalization of biomarker miRNA concentration to account for factors that affect appearance and/or stability of miRNA in bodily fluids but are not related to a target pathology.

The term "associated with" is used to encompass any correlation, co-occurrence and any cause-and-effect relationship.

The terms "microRNA" or "miRNA" as used herein refer to a class of small approximately 22 nt long non-coding RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-) 144). Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Unless otherwise noted, the name of a specific miRNA refers to a mature miRNA sequence. Under current nomenclature rules, human miRNAs are preceded with the prefix "hsa-" (i.e., an abbreviation for *Homo sapiens*). Throughout the specification and figures the hsa- prefix may be dropped for purposes of abbreviation, thus, for example, "hsa-miR-155" and "miR-155" would represent the same RNA sequence.

Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of neurodegenerative diseases. In a preferred embodiment, the subject is a human.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miRNAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified miRNAs) which have been obtained using the same protocol.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Methods for Identification of Diagnostic miRNA Pairs

To identify the most promising biomarker pairs, the present inventors used the following approach: selection of a numerator and a denominator for each pair from those circulating miRNAs, which significantly correlate (Spearman's rank correlation coefficient $\rho > 0.8$) in a respective bodily fluid of different individuals, and whose plasma concentration is differently affected by pathology. Concentrations of miRNAs in plasma depend on numerous factors, including (i) levels of miRNA expression in various organs and tissues; (ii) levels of miRNA secretion from different cell types; (iii) stability of miRNAs in extracellular space and their appearance in plasma in different forms, such as exosomes and other microvesicles, complexes with proteins, lipids and, possibly, other molecules; (iv) blood supply and blood-brain barrier permeability for brain-enriched miRNAs; and (v) other factors. A pathological process may affect some or all of these factors. The present inventors suggest that a nominator and a denominator of an effective biomarker miRNA pair should share some of these basic common factors (e.g., both are brain-enriched and secreted in exosomes) and would change differently in response to a pathology. This does not mean that any correlated miRNA will form a good biomarker pair, since if they are similarly changed by pathology their ratio will mask those changes.

The present invention provides a method of "promising" miRNA pair selection, which method comprises the following steps:

1. Concentrations of miRNAs pre-selected on the basis of their enrichment in an organ of interest (e.g., brain) are measured in a bodily fluid (e.g., plasma, serum, cerebrospinal fluid (CSF), saliva, urine) of at least two comparative cohorts (e.g., a disease and control for a diagnostic test, two diseases for a test capable of differentiating two pathologies, a disease at different stages of pathologic process development, or a disease before and after treatment for monitoring tests).

2. Means of each miRNA concentrations are calculated for comparative cohorts.

3. The difference between the means for each miRNA from two comparative cohorts is calculated and miRNAs are divided in two groups: (i) with high difference values; and (ii) with low or with opposite sign difference values.

4. miRNAs from different groups are combined as potential biomarker pairs if parameters determined in step 3 differ at least 1.5 times. One miRNA is used as a numerator and another miRNA is used as a denominator in a potential "promising" miRNA pair.

5. To further reduce an impact of individual variations of each particular miRNA concentration in plasma or other bodily fluid, miRNA with high positive correlation (Spearman's rank correlation coefficient ρ calculated for all samples in compared groups is >0.8) are selected as a numerator and a denominator for the biomarker pair. This step significantly decreases the number of potential biomarker miRNA pairs, reduces variance of selected biomarkers caused by factors unrelated to processes differentiating two comparative cohorts and significantly increases test sensitivity and specificity.

The order of steps 3-4 and step 5 can be switched as follows:

After step 1, calculate Spearman's rank correlation coefficient (r) for all possible pairs of individual miRNA measured in step 1 in all bodily fluid samples. Then select as potential biomarker pairs of miRNA with a high positive correlation (ρ>0.8), compare a ratio of miRNA concentrations in two subject cohorts for each selected miRNA pair and determine a miRNA pair as a suitable biomarker if this pair differentiates two subject cohorts with a statistically significant P-value.

Selection of miRNAs for biomarker pairs is an important step in developing screening, diagnostic and monitoring tests based on analysis of cell-free circulating miRNAs in bodily fluids. The present invention addresses this issue by providing the following methods for selection of effective biomarker pairs.

In one embodiment, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating the mean level of each miRNA measured in step (b);
(d) calculating the difference between the mean miRNA levels calculated in step (c);
(e) comparing the differences between the mean miRNA levels calculated in step (d) between all studied miRNAs and selecting as potential biomarker pairs those miRNA pairs for which the difference calculated in step (d) for one miRNA is at least 1.5 times the difference calculated for the other miRNA;
(f) calculating Spearman's rank correlation coefficient (ρ) for each potential biomarker miRNA pair selected in step (e), and
(g) identifying the miRNA pair as a suitable biomarker pair for diagnosis and/or monitoring of said pathology if its (ρ) value calculated in step (f) is at least 0.8.

In another embodiment, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (ρ) for all possible pairs of individual miRNAs measured in step (b);
(d) selecting as potential biomarker pairs those miRNA pairs which have the (ρ) value calculated in step (c) of at least 0.8;
(e) calculating the mean level of each miRNA selected in step (d);
(f) calculating the difference between the mean miRNA levels calculated in step (e);
(g) identifying a miRNA pair as a suitable biomarker pair for diagnosis and/or monitoring of said pathology if the difference calculated in step (f) for one miRNA is at least 1.5 times the difference calculated for the other miRNA.

In a further embodiment, the invention provides a method for selecting a biomarker miRNA pair for diagnosis and/or monitoring of a pathology, said method comprising the following steps:
(a) selecting at least four miRNAs known to be enriched in an organ affected by the pathology;
(b) measuring the level of each miRNA selected in step (a) in bodily fluid samples from two subject cohorts;
(c) calculating Spearman's rank correlation coefficient (ρ) for all possible pairs of individual miRNAs measured in step (b);
(d) selecting as potential biomarker pairs those miRNA pairs which have the (ρ) value calculated in step (c) of at least 0.8;
(e) calculating P-value of two subject cohorts separation for each miRNA pair selected in step (d), and
(f) identifying a miRNA pair as a suitable biomarker pair for diagnosis and/or monitoring of said pathology if this pair differentiates two subject cohorts with a statistically significant P-value.

In another embodiment, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;
(c) electronically calculating the mean level of each miRNA measured in step (b);
(d) electronically calculating a difference between the mean miRNA levels calculated in step (c);
(e) selecting from the group of measured miRNAs a set of potential miRNA pairs each comprising a first miRNA and a second miRNA, wherein the calculated difference in the mean level in step (d) of the first miRNA is at least 1.5 times the calculated difference in the mean level of the second miRNA;
(f) electronically calculating the Spearman's rank correlation coefficient (ρ) for each potential miRNA pair selected in (e);
(g) selecting from the set of potential miRNA pairs those miRNA pairs, which are suitable for the diagnosis and/or monitoring of the pathology, wherein the (ρ) value calculated in step (f) is at least 0.8, and
(h) displaying all or part of the miRNA pairs selected in step (g).

In yet another embodiment, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;

(c) electronically calculating the Spearman's rank correlation coefficient (ρ) for all possible pairs of individual miRNAs measured in step (b);
(d) selecting from the group of measured miRNAs a set of potential biomarker miRNA pairs, wherein the (ρ) value calculated in step (c) is at least 0.8;
(e) electronically calculating the mean level of each miRNA selected in step (d);
(f) electronically calculating the difference between the mean miRNA levels calculated in step (e);
(g) selecting from the group of measured miRNAs a set of suitable miRNA biomarker pairs each comprising a first miRNA and a second miRNA, wherein for each suitable biomarker miRNA pair, the calculated difference in the mean level in step (f) of the first miRNA is at least 1.5 times the calculated difference in the mean level of the second miRNA, and
(h) displaying all or part of the suitable biomarker miRNA pairs selected in step (g).

In a further embodiment, the invention provides a computer-implemented method for selecting a biomarker miRNA pair for diagnosis and/or monitoring of a pathology, said method comprising the following steps:
(a) selecting a group of miRNAs known to be enriched in an organ affected by the pathology;
(b) measuring the level of each miRNA selected in step (a) in bodily fluid samples from two subject cohorts;
(c) electronically calculating the Spearman's rank correlation coefficient (ρ) of the levels measured in step (b) for all possible pairs of individual miRNAs;
(d) selecting from the group of measured miRNAs a set of potential biomarker miRNA pairs, wherein the (ρ) value calculated in step (c) is at least 0.8;
(e) electronically calculating P-value of two subject cohorts separation for each miRNA pair selected in step (d);
(f) selecting a miRNA pair as a suitable biomarker pair for diagnosis and/or monitoring of said pathology if this miRNA pair differentiates two subject cohorts with a statistically significant P-value, and
(g) displaying all or part of the suitable biomarker miRNA pairs selected in step (f).

Non-limiting examples of the methods which can be used to measure miRNA level in any of the above methods of the invention include, e.g., RT-PCR-based methods, miRNA array-based methods, new generation sequencing, and hybridization.

Non-limiting examples of the bodily fluid samples which can be used in any of the above methods of the invention include, e.g., plasma, serum, cerebrospinal fluid (CSF), urine, and saliva.

In any of the above methods of the invention, the subjects can be, e.g., humans or experimental animals.

In any of the above methods of the invention, any two cohorts can be compared. Non-limiting examples of such cohorts include, e.g., pathology versus control [e.g., age, gender and ethnicity-matched healthy subjects], one pathology of the organ versus another pathology of the same organ, two age groups, [e.g., 20-50 years old versus 60-80 years old], males versus females [e.g., age and ethnicity-matched], two different ethnic or racial groups [e.g., age and gender-matched], etc.).

Spearman's rank correlation coefficient ρ used in the methods of the invention defined as:

$$\rho = 1 - \frac{6 \sum d_i^2}{n(n^2 - 1)};$$

wherein
$d_i$—difference between ranks for the sample i;
n—size of the cohort.

A minimal number of samples sufficient for obtaining a statistically significant difference between two cohorts in the above methods of the invention can be calculated by a standard formula for case-control study (see, e.g. Eng J. Radiology 2003, 227:309-313).

In the methods of the invention, a statistically significant P-value can be calculated using any method known in the art. Non-limiting examples of such methods are Student's t-test (for samples with normal distribution) and Mann-Whitney test (for samples with non-random distribution) (Mann and Whitney, Annals Math Stat. 1947, 18: 50-60). P-value ≥0.05 is usually accepted as statistically significant. If numerous potential biomarkers are tested Bonferroni correction can be applied.

Kits of the Invention

In conjunction with the above diagnostic, monitoring and screening methods, the present invention provides various kits comprising one or more primer and/or probe sets specific for the detection of the biomarker miRNA pairs.

Such kits can further include primer and/or probe sets specific for the detection of additional normalizer miRNAs.

Such kits can be useful for direct miRNA detection in bodily fluid samples isolated from patients or can be used on purified total RNA or miRNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Selection of miRNAs for Testing

The methods of the instant invention are based on the use of miRNAs enriched in different brain areas as numerators and denominators, which significantly improves test sensitivity and specificity. Table 1 below presents lists of brain-enriched miRNAs, miRNAs enriched in synapses, axons, dendrites and spines ("synapse and/or neurite miRNAs") and miRNAs enriched in different brain areas.

TABLE 1 miRNAs enriched in brain, different brain areas and neuronal compartments

| Brain areas and compartments | Enriched miRNAs |
|---|---|
| Brain | Let-7a,c,e, 7, 9, 19a,b, 92b, 96, 98, 99a,b, 103, 105, 106a, 107, 124a, 125a, 125b, 126, 127, 128a, 129, 132, 134, 135a, 137, 138, 139, 149, 151, 153, 154, 181a, 181b, 181c, 182, 183, 184, 190, 195, 197, 204, 211, 212, 213, 218, 219(-2-3p)(-5p), 221, 222, 299-3p, 299-5p, 323-3p, 324-5p, 326, 328, 329, 330, 331, 335-5p, 337, 338-5p, 340, 342, 346, 361, 363, 369-3p, 369-5p, 370, 377, 379, 381, 382, 383, 409-3p, 410, 411, 423-5p, 425, 432, 433-5p, 453, 485-3p, 485-5p, 487a,b, 488, 491-5p, 494, 495, 496, 497, 504, 522, 539, 541, 543, 544, 551b, 572, 577, 584, 592, 598, 625, 628, 652, 654, 655, 656, 668, 671, 672, 708, 744, 758, 769-3p,-5p, 770, 873, 874, 876-3p, 885-3p,-5p, 889, 935, 939, 941, 1193, 1197, 9*, let-7d*, 7*, 99b*, 1224-3p,-5p, 1225-3p, 1237, 125b-2*, 129*, 138-2*, 340*, 380*, 411*, 425*, 488*, 744* |
| Brain, enriched in synapses, axons, dendrites, spines | Let-7e, 7, 9, 98, 99a, 100, 124a, 125a, 125b, 128a, 129, 132, 134, 135a, 137, 138, 154, 182, 183, 204, 213, 218, 323-3p, 329, 337, 342-3p, 369-3p, 369-5p, 370, 381, 382, 409-3p, 425, 433-5p, 483-3p, 485-5p, 487b, 491-5p, 494, 495, 496, 541, 543, 656, 668, 874, 889, 935, 939, 9*, 181a-1* |
| Cortex | 9, 98, 103, 107, 124a, 125a, 125b, 126, 128a, 129, 132, 134, 138, 149, 154, 181a,b,c,d, 183, 197, 212, 213, 222, 323, 330-3p, 338-3p,-5p, 342, 370, 381, 382, 411, 425, 433, 491-5p, 539, 885 |
| Hippocampus | 9, 96, 99a, 103, 107, 124a, 125b, 126, 128a, 132, 134, 137, 138, 153, 181a, 181b,c, 184, 197, 212, 218, 219, 221, 222, 324-5p, 328, 330, 331, 335-5p, 338, 369-3p, 379, 381, 382, 383, 411, 425, 433-5p, 485-5p, 488, 491-5p, 574, 874, 885 |
| Hypothalamus | Let-7a,b,c, 103, 124a, 125a, 128a, 132, 136, 138, 212, 338, 451 |
| Cerebellum | 9, 98, 103, 124a, 125b, 128, 132, 134, 137, 138, 181a, 181b, 181c, 204, 206, 212, 213, 218, 338, 381, 382, 425, 432, 489, 592, 874, 885 |
| Amygdala | 103, 134, 138, 182, 183, 222, 323-3p, 369, 381, 382 |
| Spinal cord | 218, 219, 338, 451, 486 |
| Pituitary gland | Let-7c, 7, 9, 92a,b, 96, 99a,b, 103, 107, 125a,b, 127, 128, 132, 134, 135a, 154, 181a-c, 182, 183, 184, 195, 197, 200a,b,c, 204, 212, 213, 218, 322, 323, 324, 328, 329, 335-5p, 369, 370, 375, 377, 379, 381, 410, 411, 432, 433, 487b, 491, 494, 508, 514, 539, 542, 603, 618, 628, 652, 663, 665, 885, 890; 16, 22, 23b, 24, 26a, 27b, 29a,b,c, 30b,d, 126, 136, 141, 148a, 199b, 339, 361, 424, 429, 451, 574, 660 |
| Midbrain, Substantia nigra | Let-7a,b,c,d,e, 9, 98, 99a,b, 100, 107, 125a,b, 126, 127-3p, 129-3p, 134, 138, 149, 181a, 197, 204, 323, 329, 338, 340, 379, 383, 410, 424, 425, 432, 433, 487a,b, 539, 744, 760, 9*, 99b*, 129*, 340* |
| Medulla oblongata | 10a,b, 34a, 451, 219, 338 |

Tested miRNAs were initially selected by the present inventors based on literature data on their enrichment in brain compartments and presence in neurites (i.e., axons and/or dendrites and/or spines) and/or synapses (Hua et al.

BMC Genomics. 2009; 10: 214; Liang et al. BMC Genomics. 2007; 8:166; Landgraf et al. Cell. 2007; 129: 1401-1414; Lee et al. RNA. 2008; 14: 35-42; Schratt et al. Nature. 2006; 439: 283-289; Lugli et al. J. Neurochem. 2008; 106: 650-661; Bicker and Schratt. J. Cell Mol. Med. 2008; 12: 1466-1476; Smalheiser and Lugli. Neuromolecular Med. 2009; 11: 133-140; Rajasethupathy. Neuron. 2009; 63: 714-716; Kye. RNA. 2007; 13: 1224-1234; Yu et al. Exp. Cell Res. 2008; 314: 2618-2633; Cougot et al. J. Neurosci. 2008; 28: 13793-13804; Kawahara. Brain Nerve. 2008; 60: 1437-1444; Schratt. Rev. Neurosci. 2009; 10: 842-849; Pichardo-Casas et al. Brain Research. 2012; 1436: 20-33) as well as on their suggested involvement in neurite- and synapse-associated processes (the miR-Ontology Data Base: ferrolab.dmi.unict.it/miro/). Ubiquitous miR-16 was also tested as a potential denominator. Then the present inventors analyzed literature and their own data to find out which miRNAs are detectable in plasma.

Example 2: Quantitative Analysis

An effective biomarker used herein is a ratio (pair) of two brain-enriched miRNAs. Software described in Sheinerman et al., Aging (Albany N.Y.) 2012, 4:590-605; Sheinerman et al., Aging (Albany N.Y.) 2013, 5:925-938) was used for all calculations, including determination of miRNA pairs capable of differentiating NDs from controls and from each other as well as progressors versus non-progressors based on their concentration ratios in plasma. Mann-Whitney U-test was used to evaluate significance of differentiation of any two patient groups by various biomarker miRNA pairs. Bonferroni correction was applied for estimating significant P-values. Receiver-Operating Characteristic (ROC) curves were constructed to calculate the area under ROC curves (AUC), the sensitivity, and specificity of miRNA pairs and their combinations. Sensitivity and specificity are reported herein for the cutoff points on the ROC curves that provide the best overall accuracy. Effective pair combinations were defined using a binomial generalized linear model (GLM) with logit function (logistic regression) (Balakrishnan, 1991, Handbook of the Logistic Distribution, Marcel Dekker, Inc. ISBN 978-0-8247-8587-1; Harrell, 2001, Regression Modeling Strategies, Springer-Verlag. ISBN 0-387-95232-2). The process of selecting the best pair combinations includes following steps:
a) Calculation of model parameters, i.e. set of coefficients for regression equation, the number of such coefficients is equal to the number of the pairs combined plus one; calculation uses ratios data for persons with known statuses (e.g., ND vs. control or progressors vs. non-progressors) and maximum likelihood criteria. When coefficients have been calculated, the Logistic Regression equation is used for finding probability p for the person to be at risk. For example, if a combination examined is comprised of three pairs, the following Logistic Regression equation is used:

$$p = e^y/(1+e^y), y = b_3 * r_3 + b_2 * r_2 + b_1 * r_1 + b_0, \text{ where}$$

$r_1$, $r_2$ and $r_3$—ratio values for each pair measured for a particular person; and $b_0$, $b_1$, $b_2$ and $b_3$—set of calculated parameters (coefficients); p—probability for this person to be at risk of progression or to have ND.
b) Calculation of concordant percentage (CP), i.e. percentage of actually agreed cases (AC) of the model and information about diagnosis of persons involved, which is test accuracy. AC is a case when probability p, calculated using previous formula, is less than 0.5 for persons from Control cohort and more than 0.5 for persons with ND or progressors. CP is calculated as a ratio of number of AC to the number of all cases (NC) using in a constructing model, i.e. calculation of parameters b0-b3 in previous formula:

$$CP = AC/NC * 100 = 100 * (1 - (E1 + E2)/NC), \text{ where}$$

E1—number of type 1 errors;
E2—number of type 2 errors.

Combinations which provided the best percentage (accuracy) are selected for further use. Plasma concentrations of miRNAs comprising such combination are measured in each subject tested and probability of his/her belonging to a particular cohort (e.g., ND, progressor, control) is calculated by plugging the actual ratio values of each miRNA pair for this person into the first equation above, applying logit function to the result. Probability higher than 0.5 means that the person belongs to one cohort, e.g. ND, and probability lower than 0.5 indicates his/her belonging to another cohort, e.g. control.

Example 3: Differentiation of Various NDs from Age-Matched Controls (AMC) and from Each Other Plasma samples were obtained from 250 subjects with AD, PD, FTD, ALS and AMC (50 subjects in each group). Concentrations of 38 pre-selected miRNAs were measured in each sample by individual RT-qPCR. Table 2 presents miRNAs analyzed in this study. Many of the analyzed miRNAs are present in synapses and enriched in different brain regions affected by the target pathologies; some are associated with inflammatory processes; miR-206 is highly enriched in muscle tissue; ubiquitous apoptosis-associated miR-16 and miR-451 which is much more effectively secreted from pathologic vs normal cells are also included. RNA was extracted from $1,000_1 1.1$ plasma aliquots using a protocol based on Trizol treatment and silica (Ambion Glass Fiber Microcolumn) binding. Single target qRT-PCR was performed using the TaqMang Reverse Transcription Kit and miRNA-specific stem-loop primers (Applied Biosystems). RT step was performed in triplicate and 2 μl plasma equivalents were present in a final PCR. Placental RNA was used as a "positive control" and No-Template controls were run as a "negative control" with every run. QC of miRNA preps was performed by testing two miRNAs, known to have low variability. Calibration curves for each miRNA were generated to facilitate comparing and combining of training and validation data sets. 38 miRNAs form 703 potential miRNA pairs. According to Bonferroni correction, in a stand-alone experiment statistically significant results correspond to P-value of $0.05/703 = 7 \times 10^{-5}$. The amount of RNA equivalent to 25 μL of plasma were taken in each RT reaction, and the amount of miRNA (cDNA) equivalent to 2 μL plasma was taken into final PCR.

TABLE 2 miRNAs analyzed in the training and validation studies

| miRNA | Brain enrichment | Brain region | Present in synapses |
|---|---|---|---|
| Let-7e | + | MB, PG, Cer, FC | + |
| miR-7 | + | PG, FC, Hip | + |
| miR-9 | + | FC, MB, Hip, Cer | |
| miR-9* | + | MB, Cer, Hip, FC | + |
| miR-16 | − | PG, MB (low) | |
| miR-29a | − | PG, MB, FC, Hip | |
| miR-31 | − | Inflammatory | |
| miR-99b | + | MB, PG, FC, Cer, Hip | |

TABLE 2-continued miRNAs analyzed in the training and validation studies

| miRNA | Brain enrichment | Brain region | Present in synapses |
|---|---|---|---|
| miR-107 | + | FC, Hip, PG, MB | |
| miR-125b | + | FC, MB, PG, Hip | + |
| miR-127-3p | + | PG, MB, FC | |
| miR-128a | + | Hip, FC, HT | + |
| miR-132 | + | PG, Hip, Cer | + |
| miR-129 | + | FC, MB (Hip, TL) | |
| miR-133b | − | Muscle | |
| miR-134 | + | MB, Hip, PG | + |
| miR-135a | + | PG | + |
| miR-138 | + | Hip, FC, MB | + |
| miR-146a | − | Inflammatory | |
| miR-155 | − | Inflammatory, MB | |
| miR-181a | + | MB, FC, Hip | |
| miR-181a-2* | + | FC | |
| miR-204 | + | Cer, MB, PG | + |
| miR-206 | − | Muscle, Cer | |
| miR-218 | + | Hip, PG, SC | + |
| miR-323-3p | + | FC, MB | + |
| miR-329 | + | PG, MB | + |
| miR-335-5p | + | PG, Hip | |
| miR-338 | + | MB, FC, Hip, Cer, SC | |
| miR-370 | + | FC, PG | + |
| miR-382 | + | Hip, FC, | + |
| miR-411 | + | PG, FC, Hip | + |
| miR-433 | + | PG, MB | |
| miR-451 | − | PG, MB, FC | |
| miR-487b | + | PG, MB, FC | + |
| miR-491-5p | + | MB, FC | + |
| miR-495 | + | Glia | |
| miR-539 | + | MB, FC | |
| miR-874 | + | Cer, Hip | + |

Cer—Cerebellum;
FC—Frontal Cortex;
Hip—Hippocampus;
HT—Hypothalamus;
MB—Midbrain;
PG—Pituitary Gland;
TL—Temporal lobe;
SC—Spinal cord.

The results obtained for each miRNA were normalized per potential normalizer miRNA, converted into Relative Concentration (RC) of miRNA according to the ABI protocol ($2^{-\Delta ct}$), and compared with miRNA profiles from age-matched controls (AMC). The biomarker pairs were selected as described above. Both approaches gave similar results. Tables 3-6 present miRNA pairs differentiating AD, FTD, PD and ALS from AMC, respectively. Then the ability of various miRNA pair combinations to differentiate these pathologies were tested (Tables 7-10). Interestingly, some combinations of miRNA pairs, which detect a pathology with not the highest accuracy demonstrate very high sensitivity and specificity, which most likely means that those pairs detect particular subgroups of NDs, which are heterogeneous by underlying processes and disease development stage.

TABLE 3

Biomarker miRNA pairs for differentiating AD patients from AMC

| miRNA pairs | SENS | SPEC | ACCUR | AUC | P |
|---|---|---|---|---|---|
| miR-329/miR-181a | 0.72 | 0.73 | 0.73 | 0.82 | 8.20E-08 |
| miR-99b/miR-181a | 0.78 | 0.72 | 0.75 | 0.86 | 2.10E-09 |
| miR-99b/let-7e | 0.74 | 0.74 | 0.74 | 0.84 | 1.90E-08 |
| miR-107/miR-146a | 0.7 | 0.76 | 0.73 | 0.81 | 2.90E-07 |
| miR-9*/miR-874 | 0.72 | 0.76 | 0.74 | 0.83 | 3.00E-08 |
| miR-7/miR-16 | 0.74 | 0.76 | 0.75 | 0.81 | 1.20E-07 |

TABLE 3-continued

Biomarker miRNA pairs for differentiating AD patients from AMC

| miRNA pairs | SENS | SPEC | ACCUR | AUC | P |
|---|---|---|---|---|---|
| miR-329/miR-874 | 0.8 | 0.63 | 0.72 | 0.75 | 1.60E-05 |
| miR-329/let-7e | 0.72 | 0.69 | 0.71 | 0.77 | 4.40E-06 |
| miR-329/miR-146a | 0.64 | 0.78 | 0.71 | 0.76 | 1.20E-05 |
| miR-433/miR-181a | 0.8 | 0.64 | 0.72 | 0.77 | 9.20E-06 |
| miR-107/miR-181a | 0.78 | 0.68 | 0.73 | 0.79 | 9.00E-07 |
| miR-99b/miR-874 | 0.9 | 0.54 | 0.72 | 0.76 | 8.60E-06 |
| miR-7/miR-874 | 0.66 | 0.82 | 0.74 | 0.75 | 2.30E-05 |
| miR-125b/miR-874 | 0.7 | 0.76 | 0.73 | 0.8 | 5.80E-07 |
| miR-107/let-7e | 1 | 0.84 | 0.92 | 0.97 | 1.00E-08 |
| miR-7/miR-451 | 0.8 | 0.88 | 0.84 | 0.93 | 4.60E-07 |
| miR-204/miR-874 | 0.8 | 0.84 | 0.82 | 0.89 | 4.80E-06 |
| miR-491/let-7e | 0.88 | 0.84 | 0.86 | 0.93 | 2.80E-07 |
| miR-29a/miR-874 | 0.88 | 0.84 | 0.86 | 0.9 | 3.10E-06 |
| miR-323-3p/let-7e | 0.84 | 0.72 | 0.78 | 0.87 | 1.10E-05 |
| miR-382/let-7e | 0.76 | 0.8 | 0.78 | 0.85 | 4.10E-05 |
| miR-127/miR-411 | 0.84 | 0.96 | 0.9 | 0.96 | 2.00E-09 |
| miR-335/miR-181a | 0.56 | 0.96 | 0.76 | 0.86 | 9.10E-06 |
| miR-9*/miR-146a | 0.92 | 0.64 | 0.78 | 0.87 | 5.30E-06 |
| miR-128a/miR-181a | 0.8 | 0.84 | 0.82 | 0.89 | 5.00E-07 |
| miR-128a/miR-146a | 0.96 | 0.76 | 0.86 | 0.88 | 1.70E-06 |

TABLE 4

Biomarker miRNA pairs for differentiating FTD patients from AMC

| miRNA pairs | SENS | SPEC | ACCUR | AUC | P |
|---|---|---|---|---|---|
| miR-9*/miR-181a | 0.54 | 0.84 | 0.69 | 0.76 | 2.20E-05 |
| miR-9*/miR-874 | 0.64 | 0.76 | 0.7 | 0.75 | 2.30E-05 |
| miR-9*/miR-125b | 0.54 | 0.86 | 0.7 | 0.75 | 2.20E-05 |
| miR-9*/let-7e | 0.82 | 0.68 | 0.75 | 0.79 | 2.00E-06 |
| miR-9*/miR-155 | 0.82 | 0.72 | 0.77 | 0.82 | 2.00E-07 |
| miR-99b/miR-181a | 0.52 | 0.86 | 0.69 | 0.77 | 6.60E-06 |
| miR-99b/let-7e | 0.74 | 0.74 | 0.74 | 0.77 | 4.00E-06 |
| miR-335/let-7e | 0.66 | 0.92 | 0.79 | 0.83 | 4.80E-08 |
| miR-128a/miR-181a | 0.74 | 0.74 | 0.74 | 0.8 | 6.20E-07 |
| miR-9*/miR-31 | 0.56 | 0.7 | 0.63 | 0.7 | 7.90E-04 |
| miR-9*/miR-146a | 0.62 | 0.68 | 0.65 | 0.72 | 2.60E-04 |
| miR-9*/miR-9 | 0.62 | 0.68 | 0.65 | 0.71 | 4.80E-04 |
| miR-323-3p/miR-134 | 0.72 | 0.62 | 0.67 | 0.73 | 1.00E-04 |
| miR-338-3p/miR-181a | 0.62 | 0.64 | 0.63 | 0.71 | 5.10E-04 |
| miR-491/let-7e | 0.64 | 0.66 | 0.65 | 0.72 | 2.20E-04 |
| miR-128a/miR-874 | 0.56 | 0.68 | 0.62 | 0.7 | 9.90E-04 |
| miR-128a/let-7e | 0.88 | 0.92 | 0.9 | 0.96 | 7.70E-08 |
| miR-7/miR-874 | 0.92 | 0.8 | 0.86 | 0.96 | 5.20E-10 |
| miR-7/miR-125b | 0.8 | 0.72 | 0.76 | 0.92 | 9.50E-07 |
| miR-338-3p/let-7e | 0.88 | 0.84 | 0.86 | 0.92 | 5.10E-07 |
| miR-335/miR-181a | 0.88 | 0.96 | 0.92 | 0.97 | 7.40E-11 |
| miR-335/miR-9 | 0.84 | 0.92 | 0.88 | 0.91 | 5.00E-07 |
| miR-335/miR-146a | 0.88 | 0.84 | 0.86 | 0.93 | 3.50E-08 |

TABLE 5

Biomarker miRNA pairs for differentiating PD patients from AMC

| miRNA pairs | SENS | SPEC | ACCUR | AUC | P |
|---|---|---|---|---|---|
| miR-9*/miR-31 | 0.82 | 0.74 | 0.78 | 0.85 | 2.00E-08 |
| miR-9*/miR-138 | 0.57 | 0.96 | 0.77 | 0.85 | 2.20E-08 |
| miR-9*/miR-218 | 0.59 | 0.92 | 0.76 | 0.83 | 1.50E-07 |
| miR-9*/miR-129-3p | 0.73 | 0.92 | 0.83 | 0.91 | 4.20E-11 |
| miR-9*/miR-874 | 0.51 | 1 | 0.76 | 0.84 | 4.20E-08 |
| miR-9*/miR-204 | 0.76 | 0.9 | 0.83 | 0.87 | 4.60E-09 |
| miR-9*/miR-29a | 0.53 | 0.98 | 0.76 | 0.82 | 2.50E-07 |
| miR-99b/miR-31 | 0.86 | 0.72 | 0.79 | 0.84 | 1.30E-08 |
| miR-99b/miR-138 | 0.84 | 0.86 | 0.85 | 0.9 | 2.30E-11 |
| miR-99b/miR-218 | 0.86 | 0.7 | 0.78 | 0.8 | 2.20E-06 |
| miR-99b/miR-129-3p | 0.98 | 0.73 | 0.86 | 0.86 | 6.90E-09 |
| miR-99b/miR-874 | 0.76 | 0.88 | 0.82 | 0.9 | 1.30E-11 |
| miR-99b/miR-125b | 0.86 | 0.72 | 0.79 | 0.85 | 3.10E-09 |
| miR-99b/miR-204 | 0.96 | 0.72 | 0.84 | 0.86 | 1.80E-09 |

TABLE 5-continued

Biomarker miRNA pairs for differentiating PD patients from AMC

| miRNA pairs | SENS | SPEC | ACCUR | AUC | P |
|---|---|---|---|---|---|
| miR-99b/miR-338-3p | 0.74 | 0.86 | 0.8 | 0.87 | 1.20E-09 |
| miR-99b/miR-29a | 0.78 | 0.76 | 0.77 | 0.81 | 2.80E-07 |
| miR-99b/let-7e | 0.7 | 0.98 | 0.84 | 0.89 | 4.00E-11 |
| miR-99b/miR-9 | 0.78 | 0.78 | 0.78 | 0.86 | 1.30E-09 |
| miR-99b/miR-146a | 0.76 | 0.7 | 0.73 | 0.82 | 6.70E-08 |
| miR-127/miR-411 | 0.76 | 0.74 | 0.75 | 0.81 | 1.30E-07 |
| miR-491/miR-138 | 0.92 | 0.6 | 0.76 | 0.81 | 1.10E-07 |
| miR-128a/miR-138 | 0.94 | 0.62 | 0.78 | 0.83 | 2.50E-08 |
| miR-128a/miR-874 | 0.76 | 0.72 | 0.74 | 0.81 | 1.10E-07 |
| miR-335/miR-138 | 0.78 | 0.7 | 0.74 | 0.81 | 2.20E-07 |
| miR-181a/miR-874 | 0.88 | 0.8 | 0.84 | 0.91 | 2.30E-07 |
| miR-155/miR-31 | 0.68 | 0.72 | 0.7 | 0.82 | 1.30E-04 |
| miR-155/miR-874 | 0.76 | 0.8 | 0.78 | 0.86 | 1.70E-05 |
| let-7e/miR-31 | 0.8 | 0.72 | 0.76 | 0.79 | 7.00E-04 |
| let-7e/miR-874 | 0.72 | 0.84 | 0.78 | 0.82 | 1.70E-04 |
| miR-491/miR-138 | 0.96 | 0.68 | 0.82 | 0.85 | 1.90E-05 |
| miR-491/miR-204 | 0.88 | 0.72 | 0.8 | 0.85 | 3.10E-05 |
| miR-491/miR-31 | 0.88 | 0.72 | 0.8 | 0.84 | 2.10E-05 |
| miR-491/miR-874 | 0.8 | 0.8 | 0.8 | 0.91 | 8.20E-07 |
| miR-7/miR-129-3p | 0.79 | 0.79 | 0.79 | 0.91 | 1.40E-05 |
| miR-7/miR-874 | 0.88 | 0.84 | 0.86 | 0.95 | 2.90E-06 |
| miR-127/miR-382 | 0.72 | 0.96 | 0.84 | 0.92 | 5.50E-08 |
| miR-495/miR-382 | 0.6 | 0.96 | 0.78 | 0.89 | 1.30E-06 |
| miR-323-3p/miR-411 | 0.72 | 0.88 | 0.8 | 0.89 | 6.00E-06 |
| miR-9*/miR-132 | 1 | 1 | 1 | 1 | 7.90E-15 |
| miR-99b/miR-132 | 0.96 | 1 | 0.98 | 1 | 3.20E-14 |

TABLE 6

Biomarker miRNA pairs for differentiating ALS patients from AMC

| miRNA pairs | SENS | SPEC | ACCUR | AUC | P |
|---|---|---|---|---|---|
| miR-206/miR-31 | 0.86 | 0.78 | 0.82 | 0.9 | 8.60E-12 |
| miR-206/miR-129-3p | 0.82 | 0.82 | 0.82 | 0.88 | 4.20E-10 |
| miR-206/miR-138 | 0.8 | 0.78 | 0.79 | 0.87 | 3.10E-10 |
| miR-206/miR-874 | 0.78 | 0.8 | 0.79 | 0.86 | 8.30E-10 |
| miR-206/miR-125b | 0.74 | 0.84 | 0.79 | 0.87 | 4.30E-10 |
| miR-206/miR-204 | 0.78 | 0.78 | 0.78 | 0.85 | 4.20E-09 |
| miR-206/miR-29a | 0.78 | 0.76 | 0.77 | 0.85 | 2.60E-09 |
| miR-206/miR-155 | 0.8 | 0.72 | 0.76 | 0.82 | 7.90E-08 |
| miR-206/miR-338-3p | 0.8 | 0.72 | 0.76 | 0.82 | 7.10E-08 |
| miR-206/miR-16 | 0.94 | 0.76 | 0.85 | 0.89 | 9.20E-11 |
| miR-206/miR-451 | 0.72 | 0.84 | 0.78 | 0.87 | 7.00E-10 |
| miR-206/miR-218 | 0.8 | 0.8 | 0.8 | 0.83 | 5.90E-08 |
| miR-99b/miR-9 | 0.78 | 0.7 | 0.74 | 0.81 | 2.40E-07 |
| miR-99b/miR-155 | 0.64 | 0.84 | 0.74 | 0.8 | 4.10E-07 |
| miR-99b/miR-338-3p | 0.74 | 0.76 | 0.75 | 0.81 | 4.00E-07 |
| miR-9*/miR-129-3p | 0.51 | 1 | 0.76 | 0.8 | 1.30E-06 |
| miR-99b/miR-155 | 0.64 | 0.84 | 0.74 | 0.8 | 4.10E-07 |
| miR-99b/let-7e | 0.73 | 0.72 | 0.73 | 0.79 | 6.90E-06 |
| miR-181a/miR-338-3p | 0.84 | 0.64 | 0.74 | 0.78 | 8.70E-04 |
| miR-335/miR-338-3p | 0.92 | 0.6 | 0.76 | 0.81 | 9.80E-04 |
| miR-7/miR-31 | 0.64 | 0.8 | 0.72 | 0.79 | 7.30E-04 |
| miR-7/miR-129-3p | 0.52 | 0.96 | 0.73 | 0.81 | 2.10E-04 |
| miR-9*/miR-129-3p | 0.88 | 1 | 0.94 | 0.96 | 4.70E-08 |
| miR-9*/miR-338-3p | 0.84 | 1 | 0.92 | 0.93 | 1.50E-07 |
| miR-99b/miR-338-3p | 0.8 | 1 | 0.9 | 0.96 | 1.80E-10 |
| miR-99b/miR-128a | 0.8 | 0.96 | 0.88 | 0.95 | 2.90E-09 |
| miR-335/let-7e | 0.8 | 0.8 | 0.8 | 0.87 | 4.30E-06 |

TABLE 7

Biomarker miRNA pair combinations for differentiating AD patients from AMC

| miRNA pairs | SENS | SPEC | ACCUR | AUC |
|---|---|---|---|---|
| miR-107/miR-146a + miR-9*/miR-155 | 0.98 | 0.68 | 0.83 | 0.9 |

TABLE 7-continued

Biomarker miRNA pair combinations for differentiating AD patients from AMC

| miRNA pairs | SENS | SPEC | ACCUR | AUC |
|---|---|---|---|---|
| miR-99b/miR-874 + miR-9*/miR-155 | 0.86 | 0.92 | 0.89 | 0.91 |
| miR-9*/miR-16 + miR-7/miR-874 | 0.86 | 0.94 | 0.9 | 0.96 |
| miR-329/miR-181a + miR-9*/miR-16 + miR-7/miR-874 | 0.92 | 0.78 | 0.85 | 0.95 |
| miR-107/miR-181a + miR-9*/miR-16 + miR-7/miR-874 | 0.92 | 0.78 | 0.85 | 0.95 |
| miR-107/miR-146a + miR-9*/miR-16 + miR-7/miR-874 | 0.86 | 0.88 | 0.87 | 0.95 |
| miR-99b/miR-181a + miR-9*/miR-874 + miR-7/miR-16 | 0.92 | 0.94 | 0.93 | 0.97 |
| miR-7/miR-451 + miR-204/miR-874 + miR-491/let-7e | 1 | 0.92 | 0.96 | 0.99 |

TABLE 8

Biomarker miRNA pair combinations for differentiating FTD patients from AMC

| miRNA pairs | SENS | SPEC | ACCUR | AUC |
|---|---|---|---|---|
| miR-9*/let-7e + miR-335/let-7e | 0.82 | 0.76 | 0.79 | 0.87 |
| miR-9*/miR-155 + miR-99b/let-7e | 0.74 | 0.86 | 0.8 | 0.87 |
| miR-7/miR-874 + miR-128a/let-7e | 0.88 | 1 | 0.94 | 0.99 |
| miR-99b/let-7e + miR-335/let-7e + miR-128a/miR-181a | 0.84 | 0.9 | 0.87 | 0.94 |
| miR-9*/let-7e + miR-128a/miR-874 | 0.74 | 0.94 | 0.84 | 0.91 |
| miR-9*/let-7e + miR-7/miR-451 + miR-335/let-7e | 0.84 | 0.94 | 0.89 | 0.94 |
| miR-9*/let-7e + miR-335/let-7e + miR-128a/miR-874 | 0.78 | 0.92 | 0.85 | 0.92 |
| miR-9*/miR-9 + miR-99b/let-7e + miR-335/let-7e | 0.84 | 0.88 | 0.86 | 0.93 |
| miR-335/miR-181a + miR-335/miR-146a + miR-335/miR-9 | 0.92 | 0.96 | 0.94 | 0.98 |

TABLE 9

Biomarker miRNA pair combinations for differentiating PD patients from AMC

| miRNA pairs | SENS | SPEC | ACCUR | AUC |
|---|---|---|---|---|
| miR-9*/miR-31 + miR-99b/miR-874 | 0.94 | 0.7 | 0.82 | 0.91 |
| miR-99b/miR-874 + miR-127/miR-411 | 0.88 | 0.84 | 0.86 | 0.92 |
| miR-491/miR-874 + miR-7/miR-129-3p | 0.92 | 0.92 | 0.92 | 0.98 |
| miR-127/miR-382 + miR-128a/let-7e | 0.96 | 0.88 | 0.92 | 0.96 |
| miR-9*/miR-874 + miR-99b/miR-874 + miR-127/miR-411 | 0.84 | 0.94 | 0.89 | 0.95 |

TABLE 9-continued

Biomarker miRNA pair combinations for differentiating PD patients from AMC

| miRNA pairs | SENS | SPEC | ACCUR | AUC |
|---|---|---|---|---|
| miR-9*/miR-31 + miR-99b/miR-874 + miR-127/miR-411 | 0.9 | 0.84 | 0.87 | 0.94 |
| miR-9*/miR-129-3p + miR-127/miR-411 + miR-491/miR-138 | 0.92 | 0.9 | 0.91 | 0.96 |
| miR-9*/miR-129-3p + miR-99b/miR-874 + miR-127/miR-411 | 0.82 | 0.96 | 0.89 | 0.96 |
| miR-9*/miR-874 + miR-127/miR-411 + miR-128a/miR-138 | 0.86 | 0.96 | 0.91 | 0.96 |

TABLE 10

Biomarker miRNA pair combinations for differentiating ALS patients from AMC

| miRNA pairs | SENS | SPEC | ACCUR | AUC |
|---|---|---|---|---|
| miR-206/miR-31 + miR-99b/miR-338-3p | 0.78 | 0.94 | 0.86 | 0.93 |
| miR-206/miR-138 + miR-9*/miR-129-3p | 0.9 | 0.84 | 0.87 | 0.93 |
| miR-206/miR-31 + miR-335/miR-338-3p | 0.84 | 0.92 | 0.88 | 0.96 |
| miR-206/miR-16 + miR-335/miR-338-3p | 0.72 | 0.88 | 0.8 | 0.91 |
| miR-9*/miR-129-3p + miR-99b/miR-338-3p | 0.84 | 1 | 0.92 | 0.98 |
| miR-206/miR-204 + miR-206/miR-218 + miR-335/miR-338-3p | 0.88 | 0.74 | 0.81 | 0.91 |
| miR-206/miR-204 + miR-206/miR-218 + miR-9*/miR-129-3p | 0.88 | 0.82 | 0.85 | 0.91 |
| miR-206/miR-338-3p + miR-99b/miR-129-3p + miR-335/miR-338-3p | 0.92 | 0.76 | 0.84 | 0.92 |
| miR-206/miR-338-3p + miR-99b/miR-155 + miR-335/miR-338-3p | 0.76 | 0.9 | 0.83 | 0.93 |
| miR-181a/miR-338-3p + miR-335/miR-338-3p + miR-7/miR-31 + miR-7/miR-129-3p | 0.92 | 0.76 | 0.84 | 0.91 |

The data obtained demonstrate that many biomarker miRNA pairs differentiate several NDs from AMC, which is explained that during disease progression NDs expand to new brain areas and synaptic miRNAs from these areas are released to extracellular space and bloodstream. In addition, involvement of new brain areas in pathology complicates selection of normalizers. Nevertheless, despite all these factors many miRNA pairs and their combinations differentiate each pathology from AMC with up to 80%-95% accuracy. The list of best numerators (biomarker miRNAs) and denominators (normalizer miRNAs) is presented in Table 11. Data below demonstrate also that due to different level of various brain areas involvement in each pathology NDs can be effectively differentiated from each other.

TABLE 11

The list of most common numerator and denominator miRNAs in biomarker miRNA pairs capable of differentiating various subject cohorts

| Compared cohorts | Numerators Name | Denominators Name |
|---|---|---|
| AD-CNTR | miR-7 | let-7e |
|  | miR-107 | miR-128a |
|  | miR-125b | miR-146a |
|  | miR-127 | miR-16 |
|  | miR-128a | miR-181a |
|  | miR-204 | miR-29a |
|  | miR-29a | miR-411 |
|  | miR-323-3p | miR-874 |
|  | miR-329 | miR-451 |
|  | miR-335 |  |
|  | miR-382 |  |
|  | miR-9* |  |
|  | miR-99b |  |
|  | miR-491 |  |
| FTD-CNTR | miR-7 | let-7e |
|  | miR-128a | miR-125b |
|  | miR-323-3p | miR-146a |
|  | miR-335 | miR-155 |
|  | miR-338-3p | miR-181a |
|  | miR-9* | miR-31 |
|  | miR-99b | miR-874 |
|  | miR-491 | miR-9 |
| PD-CNTR | miR-7 | let-7e |
|  | let-7e | miR-125b |
|  | miR-127 | miR-128a |
|  | miR-128a | miR-138 |
|  | miR-155 | miR-146a |
|  | miR-181a | miR-155 |
|  | miR-323-3p | miR-181a |
|  | miR-335 | miR-204 |
|  | miR-9* | miR-218 |
|  | miR-99b | miR-29a |
|  | miR-491 | miR-31 |
|  | miR-495 | miR-338-3p |
|  |  | miR-382 |
|  |  | miR-411 |
|  |  | miR-874 |
|  |  | miR-9 |
|  |  | miR-129-3p |
|  |  | miR-132 |
| ALS-CNTR | miR-7 | let-7e |
|  | miR-181a | miR-125b |
|  | miR-206 | miR-128a |
|  | miR-335 | miR-138 |
|  | miR-9* | miR-155 |
|  | miR-99b | miR-16 |
|  |  | miR-204 |
|  |  | miR-218 |
|  |  | miR-29a |
|  |  | miR-31 |
|  |  | miR-338-3p |
|  |  | miR-874 |
|  |  | miR-9 |
|  |  | miR-129-3p |
|  |  | miR-451 |

Example 4: Differentiation of Various NDs from Each Other

The samples, procedures, miRNA concentrations and their analysis described in Example 3 were also applied for searching biomarker miRNA pairs and their combination capable of differentiating various NDs from each other. The results for each pair of NDs are presented in Tables 12-23.

TABLE 12

Biomarker miRNA pairs for differentiating AD and FTD patients

| miRNA pairs | SENS | SPEC | ACCUR | AUC | P-value |
|---|---|---|---|---|---|
| miR-125b/miR-29a | 0.64 | 0.68 | 0.66 | 0.83 | 3.20E-06 |
| miR-125b/miR-874 | 0.68 | 0.68 | 0.68 | 0.82 | 3.10E-05 |
| miR-107/miR-335-5p | 0.72 | 0.68 | 0.7 | 0.72 | 8.00E-07 |
| miR-155/miR-29a | 0.76 | 0.64 | 0.7 | 0.77 | 2.90E-05 |
| miR-329/miR-874 | 0.76 | 0.71 | 0.73 | 0.85 | 2.50E-05 |
| miR-329/miR-181a | 0.8 | 0.79 | 0.8 | 0.9 | 1.70E-06 |
| miR-329/miR-411 | 0.76 | 0.79 | 0.78 | 0.88 | 4.00E-06 |
| miR-7/miR-16 | 0.68 | 0.68 | 0.68 | 0.85 | 2.50E-05 |
| miR-451/miR-16 | 0.8 | 0.72 | 0.76 | 0.87 | 6.00E-06 |
| miR-155/miR-335-5p | 0.84 | 0.84 | 0.84 | 0.87 | 1.00E-05 |
| let-7e/miR-335-5p | 0.84 | 0.8 | 0.82 | 0.93 | 1.10E-08 |

TABLE 13

Biomarker miRNA pair combinations for differentiating AD and FTD patients

| miRNA pairs | SENS | SPEC | ACCUR | AUC |
|---|---|---|---|---|
| miR-125b/miR-29a + miR-107/miR-335-5p + miR-155/miR-29a | 0.78 | 0.74 | 0.76 | 0.87 |
| miR-125b/miR-29a + miR-125b/miR-874 + miR-107/miR-335-5p | 0.78 | 0.76 | 0.77 | 0.87 |
| miR-125b/miR-874 + miR-107/miR-335-5p + miR-155/miR-29a | 0.76 | 0.76 | 0.76 | 0.87 |
| miR-329/miR-411 + miR-329/miR-16 | 0.8 | 0.75 | 0.78 | 0.91 |
| miR-329/miR-874 + miR-329/miR-411 | 0.84 | 0.79 | 0.82 | 0.92 |
| miR-329/miR-411 + miR-329/miR-16 + miR-7/miR-16 | 0.72 | 0.84 | 0.78 | 0.92 |
| miR-451/miR-16 + miR-155/miR-335-5p + let-7e/miR-335-5p | 0.88 | 0.88 | 0.88 | 0.97 |

TABLE 14

Biomarker miRNA pairs for differentiating AD and PD patients

| miRNA pairs | SENS | SPEC | ACCUR | AUC | P-value |
|---|---|---|---|---|---|
| miR-31/miR-9* | 0.72 | 0.71 | 0.72 | 0.8 | 3.80E-07 |
| miR-31/miR-99b | 0.76 | 0.68 | 0.72 | 0.77 | 4.70E-06 |
| miR-31/miR-16 | 0.68 | 0.76 | 0.72 | 0.77 | 5.80E-06 |
| miR-31/miR-29a | 0.8 | 0.66 | 0.73 | 0.81 | 4.20E-07 |
| miR-138/miR-9* | 0.7 | 0.65 | 0.68 | 0.76 | 7.80E-06 |
| miR-138/miR-99b | 0.74 | 0.68 | 0.71 | 0.82 | 1.10E-07 |
| miR-138/miR-181a | 0.64 | 0.72 | 0.68 | 0.78 | 2.60E-06 |
| miR-138/miR-491-5p | 0.7 | 0.7 | 0.7 | 0.77 | 4.30E-06 |
| miR-138/miR-335-5p | 0.64 | 0.74 | 0.69 | 0.79 | 7.70E-06 |
| miR-138/miR-128a | 0.7 | 0.7 | 0.7 | 0.78 | 1.90E-06 |
| miR-138/miR-146a | 0.6 | 0.74 | 0.67 | 0.77 | 4.80E-06 |
| miR-138/let-7e | 0.66 | 0.7 | 0.68 | 0.77 | 4.30E-06 |
| miR-138/miR-16 | 0.72 | 0.62 | 0.67 | 0.77 | 7.20E-06 |
| miR-138/miR-29a | 0.72 | 0.66 | 0.69 | 0.76 | 1.60E-05 |
| miR-129-3p/miR-9* | 0.7 | 0.73 | 0.72 | 0.85 | 2.90E-09 |
| miR-129-3p/miR-99b | 0.76 | 0.76 | 0.76 | 0.83 | 1.90E-08 |
| miR-129-3p/miR-335-5p | 0.68 | 0.63 | 0.66 | 0.78 | 2.30E-05 |
| miR-129-3p/miR-146a | 0.72 | 0.55 | 0.64 | 0.77 | 4.60E-06 |
| miR-129-3p/miR-16 | 0.74 | 0.67 | 0.71 | 0.78 | 2.00E-06 |
| miR-129-3p/miR-29a | 0.62 | 0.65 | 0.64 | 0.76 | 7.00E-06 |
| miR-125b/miR-9* | 0.74 | 0.61 | 0.68 | 0.75 | 2.10E-05 |
| miR-125b/miR-99b | 0.78 | 0.66 | 0.72 | 0.81 | 1.90E-07 |
| miR-125b/miR-181a | 0.66 | 0.76 | 0.71 | 0.78 | 2.60E-06 |
| miR-125b/miR-491-5p | 0.7 | 0.8 | 0.75 | 0.79 | 1.60E-06 |
| miR-125b/miR-335-5p | 0.68 | 0.72 | 0.7 | 0.8 | 8.90E-07 |
| miR-125b/miR-128a | 0.7 | 0.78 | 0.74 | 0.8 | 6.50E-07 |

TABLE 14-continued

Biomarker miRNA pairs for differentiating AD and PD patients

| miRNA pairs | SENS | SPEC | ACCUR | AUC | P-value |
|---|---|---|---|---|---|
| miR-125b/miR-146a | 0.7 | 0.68 | 0.69 | 0.78 | 4.00E-06 |
| miR-125b/let-7e | 0.74 | 0.78 | 0.76 | 0.79 | 3.00E-06 |
| miR-218/miR-9* | 0.62 | 0.73 | 0.68 | 0.77 | 4.00E-06 |
| miR-218/miR-16 | 0.7 | 0.71 | 0.71 | 0.76 | 1.10E-05 |
| miR-204/miR-9* | 0.72 | 0.76 | 0.74 | 0.82 | 5.20E-08 |
| miR-204/miR-99b | 0.68 | 0.66 | 0.67 | 0.8 | 6.60E-07 |
| miR-204/miR-146a | 0.76 | 0.64 | 0.7 | 0.78 | 2.40E-06 |
| miR-338-3p/miR-99b | 0.66 | 0.66 | 0.66 | 0.75 | 3.40E-05 |
| miR-107/miR-99b | 0.66 | 0.72 | 0.69 | 0.78 | 4.60E-06 |
| miR-107/miR-491-5p | 0.72 | 0.56 | 0.64 | 0.76 | 1.40E-05 |

TABLE 15

Biomarker miRNA pair combinations for differentiating AD and PD patients

| miRNA pairs | SENS | SPEC | ACCUR | AUC |
|---|---|---|---|---|
| miR-31/miR-16 + miR-129-3p/miR-9* + miR-204/miR-99b | 0.88 | 0.88 | 0.88 | 0.95 |
| miR-129-3p/miR-16 + miR-125b/miR-181a + miR-204/miR-9* | 0.84 | 0.86 | 0.85 | 0.95 |
| miR-31/miR-99b + miR-129-3p/miR-16 + miR-204/miR-9* | 0.9 | 0.88 | 0.89 | 0.96 |
| miR-31/miR-16 + miR-125b/miR-181a + miR-204/miR-9* | 0.82 | 0.88 | 0.85 | 0.95 |
| miR-31/miR-16 + miR-129-3p/miR-335-5p + miR-204/miR-9* | 0.86 | 0.9 | 0.88 | 0.96 |

TABLE 16

Biomarker miRNA pairs for differentiating AD and ALS patients

| miRNA pairs | SENS | SPEC | ACCUR | AUC | P-value |
|---|---|---|---|---|---|
| miR-329/miR-206 | 0.76 | 0.76 | 0.76 | 0.82 | 1.90E-07 |
| miR-329/miR-9* | 0.68 | 0.58 | 0.63 | 0.77 | 1.10E-05 |
| miR-329/miR-99b | 0.72 | 0.7 | 0.71 | 0.78 | 2.50E-06 |
| miR-329/miR-335-5p | 0.74 | 0.66 | 0.7 | 0.79 | 1.90E-06 |
| miR-329/miR-146a | 0.74 | 0.64 | 0.69 | 0.77 | 6.70E-06 |
| miR-329/miR-411 | 0.74 | 0.64 | 0.69 | 0.76 | 2.00E-05 |
| miR-31/miR-206 | 0.78 | 0.78 | 0.78 | 0.88 | 3.30E-10 |
| miR-31/miR-16 | 0.7 | 0.7 | 0.7 | 0.78 | 2.40E-06 |
| miR-129-3p/miR-206 | 0.8 | 0.82 | 0.81 | 0.87 | 4.50E-10 |
| miR-129-3p/miR-16 | 0.74 | 0.61 | 0.68 | 0.76 | 1.30E-05 |
| miR-433/miR-206 | 0.7 | 0.74 | 0.72 | 0.8 | 7.50E-07 |
| miR-433/miR-335-5p | 0.76 | 0.6 | 0.68 | 0.76 | 2.10E-05 |
| miR-125b/miR-206 | 0.76 | 0.78 | 0.77 | 0.87 | 9.40E-10 |
| miR-125b/miR-335-5p | 0.62 | 0.72 | 0.67 | 0.78 | 4.60E-06 |
| miR-125b/miR-874 | 0.7 | 0.7 | 0.7 | 0.75 | 2.10E-05 |
| miR-323-3p/miR-206 | 0.7 | 0.72 | 0.71 | 0.8 | 5.80E-07 |
| miR-495/miR-206 | 0.72 | 0.76 | 0.74 | 0.79 | 1.00E-06 |
| miR-204/miR-206 | 0.76 | 0.74 | 0.75 | 0.82 | 7.10E-08 |
| miR-127-3p/miR-206 | 0.7 | 0.72 | 0.71 | 0.78 | 4.60E-06 |
| miR-107/miR-206 | 0.74 | 0.68 | 0.71 | 0.79 | 1.10E-06 |
| miR-107/miR-99b | 0.68 | 0.74 | 0.71 | 0.77 | 5.50E-06 |
| miR-107/miR-335-5p | 0.74 | 0.62 | 0.68 | 0.82 | 4.20E-08 |
| miR-107/let-7e | 0.7 | 0.61 | 0.66 | 0.79 | 5.60E-07 |
| miR-107/miR-146a | 0.76 | 0.78 | 0.77 | 0.83 | 5.10E-08 |
| miR-107/miR-491-5p | 0.74 | 0.7 | 0.72 | 0.8 | 9.20E-07 |
| miR-138/miR-206 | 0.76 | 0.7 | 0.73 | 0.84 | 9.80E-09 |
| miR-134/miR-206 | 0.66 | 0.72 | 0.69 | 0.76 | 1.80E-06 |
| miR-9/miR-206 | 0.72 | 0.7 | 0.71 | 0.76 | 1.40E-05 |
| miR-155/miR-206 | 0.74 | 0.72 | 0.73 | 0.8 | 6.60E-07 |
| miR-7/miR-206 | 0.7 | 0.7 | 0.7 | 0.81 | 1.70E-07 |
| miR-338-3p/miR-206 | 0.76 | 0.66 | 0.71 | 0.8 | 7.60E-07 |

TABLE 16-continued

Biomarker miRNA pairs for differentiating AD and ALS patients

| miRNA pairs | SENS | SPEC | ACCUR | AUC | P-value |
|---|---|---|---|---|---|
| miR-29a/miR-206 | 0.76 | 0.78 | 0.77 | 0.82 | 8.80E−08 |
| miR-338-3p/let-7e | 0.84 | 0.79 | 0.82 | 0.95 | 1.30E−07 |
| miR-433/miR-411 | 0.84 | 0.84 | 0.84 | 0.91 | 1.70E−07 |
| miR-433/miR-382 | 0.76 | 0.72 | 0.74 | 0.88 | 4.80E−06 |
| miR-127-3p/miR-411 | 0.8 | 0.68 | 0.74 | 0.86 | 1.20E−05 |

TABLE 17

Biomarker miRNA pair combinations for differentiating AD and ALS patients

| miRNA pairs | SENS | SPEC | ACCUR | AUC |
|---|---|---|---|---|
| miR-31/miR-206 + miR-125b/miR-335-5p | 0.86 | 0.8 | 0.83 | 0.93 |
| miR-31/miR-206 + miR-125b/miR-335-5p + miR-107/miR-335-5p | 0.94 | 0.92 | 0.93 | 0.98 |
| miR-31/miR-206 + miR-125b/miR-335-5p + miR-107/miR-491-5p | 0.92 | 0.94 | 0.93 | 0.98 |
| miR-125b/miR-335-5p + miR-107/let-7e + miR-138/miR-206 | 0.9 | 0.9 | 0.9 | 0.98 |
| miR-125b/miR-335-5p + miR-107/miR-491-5p + miR-338-3p/miR-206 | 0.92 | 0.94 | 0.93 | 0.98 |
| miR-125b/miR-335-5p + miR-107/let-7e + miR-338-3p/miR-206 | 0.94 | 0.9 | 0.92 | 0.98 |
| miR-125b/miR-335-5p + miR-323-3p/miR-206 + miR-107/let-7e | 0.94 | 0.88 | 0.91 | 0.98 |
| miR-433/miR-382 + miR-127-3p/miR-411 | 0.92 | 0.8 | 0.86 | 0.94 |

TABLE 18

Biomarker miRNA pairs for differentiating FTD and PD patients

| miRNA pairs | SENS | SPEC | ACCUR | AUC | P-value |
|---|---|---|---|---|---|
| miR-218/miR-9* | 0.66 | 0.69 | 0.68 | 0.78 | 2.60E−06 |
| miR-218/miR-99b | 0.68 | 0.67 | 0.68 | 0.76 | 1.20E−05 |
| miR-138/miR-99b | 0.72 | 0.68 | 0.7 | 0.79 | 9.80E−07 |
| miR-138/miR-181a | 0.62 | 0.72 | 0.67 | 0.77 | 5.10E−06 |
| miR-138/miR-491-5p | 0.68 | 0.7 | 0.69 | 0.75 | 1.90E−05 |
| miR-31/miR-9* | 0.7 | 0.59 | 0.65 | 0.76 | 8.10E−06 |
| miR-31/miR-99b | 0.68 | 0.6 | 0.64 | 0.77 | 4.90E−06 |
| miR-129-3p/miR-9* | 0.68 | 0.67 | 0.68 | 0.8 | 4.80E−06 |
| miR-129-3p/miR-99b | 0.72 | 0.73 | 0.73 | 0.8 | 2.00E−07 |
| miR-204/miR-9* | 0.76 | 0.71 | 0.74 | 0.77 | 4.00E−06 |
| miR-204/miR-99b | 0.68 | 0.66 | 0.67 | 0.81 | 2.90E−07 |
| miR-338-3p/miR-99b | 0.74 | 0.78 | 0.76 | 0.86 | 1.30E−09 |
| miR-338-3p/miR-491-5p | 0.7 | 0.76 | 0.73 | 0.84 | 1.60E−08 |
| miR-338-3p/miR-107 | 0.68 | 0.74 | 0.71 | 0.78 | 1.90E−06 |
| miR-338-3p/let-7e | 0.58 | 0.68 | 0.63 | 0.76 | 7.80E−06 |
| miR-338-3p/miR-146a | 0.66 | 0.72 | 0.69 | 0.79 | 2.10E−06 |
| miR-874/miR-99b | 0.7 | 0.64 | 0.67 | 0.77 | 1.10E−05 |
| miR-125b/miR-99b | 0.68 | 0.62 | 0.65 | 0.77 | 5.90E−06 |
| miR-29a/miR-99b | 0.72 | 0.76 | 0.74 | 0.79 | 1.00E−06 |
| miR-323-3p/miR-127-3p | 0.68 | 0.74 | 0.71 | 0.78 | 2.70E−06 |
| miR-411/miR-127-3p | 0.6 | 0.76 | 0.68 | 0.8 | 6.00E−07 |
| miR-155/miR-99b | 0.76 | 0.66 | 0.71 | 0.76 | 1.80E−05 |
| miR-335-5p/miR-99b | 0.64 | 0.7 | 0.67 | 0.76 | 1.40E−05 |
| miR-382/miR-134 | 0.72 | 0.72 | 0.72 | 0.86 | 7.40E−06 |

TABLE 19

Biomarker miRNA pair combinations for differentiating FTD and PD patients

| miRNA pairs | SENS | SPEC | ACCUR | AUC |
|---|---|---|---|---|
| miR-129-3p/miR-9* + miR-338-3p/miR-491-5p | 0.86 | 0.8 | 0.83 | 0.93 |
| miR-129-3p/miR-9* + miR-338-3p/miR-99b + miR-323-3p/miR-127-3p | 0.84 | 0.9 | 0.87 | 0.93 |
| miR-129-3p/miR-9* + miR-338-3p/miR-491-5p + miR-411/miR-127-3p | 0.78 | 0.9 | 0.84 | 0.93 |
| miR-129-3p/miR-9* + miR-338-3p/miR-491-5p + miR-323-3p/miR-127-3p | 0.76 | 0.88 | 0.82 | 0.93 |
| miR-204/miR-9* + miR-338-3p/miR-491-5p + miR-323-3p/miR-127-3p | 0.74 | 0.88 | 0.81 | 0.92 |
| miR-129-3p/miR-9* + miR-29a/miR-99b + miR-323-3p/miR-127-3p | 0.74 | 0.84 | 0.79 | 0.93 |
| miR-138/miR-181a + miR-129-3p/miR-9* + miR-411/miR-127-3p | 0.74 | 0.94 | 0.84 | 0.92 |

TABLE 20

Biomarker miRNA pairs for differentiating FTD and ALS patients

| miRNA pairs | SENS | SPEC | ACCUR | AUC | P-value |
|---|---|---|---|---|---|
| miR-31/miR-206 | 0.8 | 0.76 | 0.78 | 0.87 | 2.40E−10 |
| miR-138/miR-206 | 0.78 | 0.7 | 0.74 | 0.85 | 2.80E−09 |
| miR-29a/miR-206 | 0.78 | 0.78 | 0.78 | 0.87 | 3.60E−10 |
| miR-129-3p/miR-206 | 0.8 | 0.8 | 0.8 | 0.86 | 7.00E−10 |
| miR-204/miR-206 | 0.74 | 0.74 | 0.74 | 0.85 | 3.10E−09 |
| miR-338-3p/miR-206 | 0.74 | 0.72 | 0.73 | 0.84 | 1.60E−08 |
| miR-338-3p/let-7e | 0.58 | 0.76 | 0.67 | 0.81 | 1.70E−07 |
| miR-7/miR-206 | 0.76 | 0.68 | 0.72 | 0.85 | 6.60E−09 |
| miR-128a/miR-206 | 0.76 | 0.72 | 0.74 | 0.82 | 1.40E−07 |
| miR-16/miR-206 | 0.76 | 0.76 | 0.76 | 0.88 | 9.20E−11 |
| miR-125b/miR-206 | 0.78 | 0.74 | 0.76 | 0.85 | 6.20E−08 |
| miR-874/miR-206 | 0.72 | 0.78 | 0.75 | 0.84 | 1.50E−08 |
| miR-218/miR-206 | 0.76 | 0.8 | 0.78 | 0.83 | 2.40E−08 |
| miR-29a/miR-155 | 0.8 | 0.64 | 0.72 | 0.86 | 2.50E−05 |
| miR-338-3p/miR-181a | 0.84 | 0.84 | 0.84 | 0.92 | 7.10E−07 |
| miR-338-3p/miR-335-5p | 0.88 | 0.84 | 0.86 | 0.94 | 1.50E−07 |
| miR-338-3p/miR-491-5p | 0.8 | 0.8 | 0.8 | 0.89 | 3.40E−06 |
| miR-338-3p/miR-146a | 0.72 | 0.84 | 0.78 | 0.87 | 1.90E−05 |
| miR-323-3p/miR-127-3p | 0.76 | 0.76 | 0.76 | 0.89 | 6.90E−06 |
| miR-129-3p/miR-9* | 0.84 | 0.88 | 0.86 | 0.88 | 6.00E−06 |

TABLE 21

Biomarker miRNA pair combinations for differentiating FTD and ALS patients

| miRNA pairs | SENS | SPEC | ACCUR | AUC |
|---|---|---|---|---|
| miR-29a/miR-206 + miR-338-3p/let-7e | 0.8 | 0.84 | 0.82 | 0.93 |
| miR-129-3p/miR-206 + miR-338-3p/let-7e | 0.84 | 0.86 | 0.85 | 0.94 |
| miR-204/miR-206 + miR-338-3p/let-7e | 0.8 | 0.88 | 0.84 | 0.94 |
| miR-138/miR-206 + miR-338-3p/let-7e | 0.78 | 0.9 | 0.84 | 0.93 |
| miR-129-3p/miR-206 + miR-338-3p/let-7e + miR-125b/miR-206 | 0.84 | 0.82 | 0.83 | 0.93 |

TABLE 21-continued

Biomarker miRNA pair combinations for differentiating FTD and ALS patients

| miRNA pairs | SENS | SPEC | ACCUR | AUC |
|---|---|---|---|---|
| miR-129-3p/miR-206 + miR-338-3p/let-7e + miR-874/miR-206 | 0.84 | 0.82 | 0.83 | 0.93 |
| miR-129-3p/miR-206 + miR-338-3p/let-7e + miR-7/miR-206 | 0.8 | 0.82 | 0.81 | 0.93 |
| miR-338-3p/miR-181a + miR-338-3p/miR-335-5p + miR-323-3p/miR-127-3p | 0.84 | 0.96 | 0.9 | 0.98 |

TABLE 22

Biomarker miRNA pairs for differentiating PD and ALS patients

| miRNA pairs | SENS | SPEC | ACCUR | AUC | P-value |
|---|---|---|---|---|---|
| miR-329/miR-206 | 0.78 | 0.76 | 0.77 | 0.84 | 7.70E−09 |
| miR-9*/miR-206 | 0.78 | 0.78 | 0.78 | 0.87 | 3.90E−10 |
| miR-433/miR-206 | 0.74 | 0.76 | 0.75 | 0.85 | 3.40E−09 |
| miR-370/miR-206 | 0.68 | 0.72 | 0.7 | 0.81 | 1.80E−07 |
| miR-134/miR-206 | 0.72 | 0.74 | 0.73 | 0.84 | 7.70E−09 |
| miR-323-3p/miR-206 | 0.76 | 0.76 | 0.76 | 0.85 | 3.20E−09 |
| miR-9/miR-206 | 0.7 | 0.78 | 0.74 | 0.85 | 2.90E−09 |
| miR-99b/miR-206 | 0.74 | 0.8 | 0.77 | 0.86 | 7.90E−10 |
| miR-495/miR-206 | 0.76 | 0.76 | 0.76 | 0.84 | 1.00E−08 |
| miR-382/miR-206 | 0.72 | 0.72 | 0.72 | 0.84 | 1.40E−08 |
| miR-491-5p/miR-206 | 0.76 | 0.76 | 0.76 | 0.87 | 4.70E−10 |
| miR-29a/miR-206 | 0.76 | 0.78 | 0.77 | 0.89 | 4.70E−11 |
| miR-411/miR-206 | 0.7 | 0.74 | 0.72 | 0.84 | 1.20E−08 |
| miR-181a/miR-206 | 0.76 | 0.72 | 0.74 | 0.84 | 1.80E−08 |
| miR-155/miR-206 | 0.8 | 0.74 | 0.77 | 0.87 | 3.80E−10 |
| miR-146a/miR-206 | 0.76 | 0.68 | 0.72 | 0.86 | 9.80E−10 |
| miR-7/miR-206 | 0.8 | 0.76 | 0.78 | 0.89 | 5.50E−11 |
| miR-107/miR-204 | 0.72 | 0.76 | 0.74 | 0.86 | 3.20E−05 |
| miR-107/let-7e | 0.84 | 0.83 | 0.84 | 0.93 | 3.70E−07 |
| miR-107/miR-335-5p | 0.68 | 0.8 | 0.74 | 0.85 | 3.30E−05 |
| miR-107/miR-146a | 0.84 | 0.8 | 0.82 | 0.86 | 2.50E−05 |
| miR-128a/miR-874 | 0.76 | 0.72 | 0.74 | 0.88 | 7.20E−06 |
| miR-128a/let-7e | 0.68 | 0.79 | 0.73 | 0.86 | 1.40E−04 |
| miR-329/miR-382 | 0.76 | 0.64 | 0.7 | 0.81 | 1.30E−04 |
| miR-433/miR-382 | 0.88 | 0.68 | 0.78 | 0.88 | 3.80E−06 |
| miR-433/miR-411 | 0.8 | 0.76 | 0.78 | 0.86 | 9.10E−06 |

TABLE 23

Biomarker miRNA pair combinations for differentiating PD and ALS patients

| miRNA pairs | SENS | SPEC | ACCUR | AUC |
|---|---|---|---|---|
| miR-29a/miR-206 + miR-7/miR-206 | 0.78 | 0.76 | 0.77 | 0.9 |
| miR-9*/miR-206 + miR-7/miR-206 | 0.78 | 0.8 | 0.79 | 0.91 |
| miR-9*/miR-206 + miR-155/miR-206 + miR-7/miR-206 | 0.82 | 0.8 | 0.81 | 0.9 |
| miR-107/miR-204 + miR-107/miR-146a + miR-128a/miR-874 | 0.96 | 0.8 | 0.88 | 0.94 |
| miR-107/miR-204 + miR-128a/miR-874 + miR-128a/let-7e | 0.88 | 0.88 | 0.88 | 0.97 |
| miR-107/miR-335-5p + miR-128a/miR-874 + miR-128a/let-7e | 0.88 | 0.8 | 0.84 | 0.95 |
| miR-107/miR-204 + miR-107/miR-146a + miR-128a/let-7e | 0.88 | 0.84 | 0.86 | 0.95 |
| miR-329/miR-382 + miR-433/miR-382 + miR-433/miR-411 | 0.84 | 0.8 | 0.82 | 0.9 |

Example 5: Early Detection of AD and Prediction of Disease Progression

Plasma samples were obtained from 59 subjects (30 subjects with CDR 0, 24 subjects with CDR 0.5 and 5 subjects with CDR 1.0). All CDR 0.5 and CDR 1 subjects had lower than normal levels of Aβ in CSF, indicating that they were on early (pre-MCI or MCI) stage of AD. 14 subjects with CDR>0 had normal MMSE (27-30)-pre-MCI, and 15 subjects had MMSE<27-MCI.

TABLE 24 miRNAs tested in the study on early (pre-MCI/MCI) AD detection.

| miRNA | Brain enrichment | Enriched in | Present in synapses |
|---|---|---|---|
| miR-128a | + | Hip, FC, HT | + |
| miR-132 | + | PG, Hip | + |
| miR-874 | + | Cer, Hip | + |
| miR-491-5p | + | MB, FC | + |
| miR-134 | + | MB, Hip, PG | + |
| miR-323-3p | + | FC, Hip, MB | + |
| miR-382 | + | Hip, FC, | + |
| miR-370 | + | FC, PG | + |
| miR-7 | + | PG, FC, Hip | + |
| miR-9 | + | FC, MB, Hip, Cer | |
| miR-16 | Ubiquitous | PG, MB (low) | |
| miR-451 | Ubiquitous | PG, MB, FC | |
| miR-125b | + | FC, MB, PG, Hip | + |
| miR-135a | + | PG, Hip | + |
| miR-335-5p | + | PG, Hip | |
| miR-127-3p | + | PG, MB, FC | + |
| miR-410 | + | PG, MB | |
| miR-433 | + | PG, MB | |

Cer—Cerebellum;
FC—Frontal Cortex;
Hip—Hippocampus;
HT—Hypothalamus;
MB—Midbrain;
PG—Pituitary Gland.

RNA extraction, measurement of concentrations of 18 pre-selected miRNA (Table 23) in each sample by single target RT-qPCR and data analysis were performed as described above. Tables 24 and 25 present lists of miRNA pairs and their combinations capable of differentiating CDR 0.5 and CDR 1 subjects (combined pre-MCI and MCI cohort) from CDR 0 controls.

TABLE 25

Biomarker miRNA pairs for early (pre-MCI/MCI) AD detection

| miRNA pairs | Accuracy | AUC | P-value |
|---|---|---|---|
| miR-134/miR-370 | 0.74 | 083 | <2.00E−5 |
| miR-323-3p/miR-127-3p | 0.78 | 0.83 | <3.00E−5 |
| miR-323-3p/miR-433 | 0.81 | 0.88 | <2.00E−6 |

TABLE 23-continued

Biomarker miRNA pair combinations for differentiating PD and ALS patients

| miRNA pairs | SENS | SPEC | ACCUR | AUC |
|---|---|---|---|---|
| miR-107/miR-204 + miR-107/miR-146a + miR-128a/let-7e | 0.88 | 0.84 | 0.86 | 0.95 |
| miR-329/miR-382 + miR-433/miR-382 + miR-433/miR-411 | 0.84 | 0.8 | 0.82 | 0.9 |

TABLE 25-continued

Biomarker miRNA pairs for early (pre-MCI/MCI) AD detection

| miRNA pairs | Accuracy | AUC | P-value |
|---|---|---|---|
| miR-134/miR-127-3p | 0.76 | 0.79 | <3.00E−4 |
| miR-323-3p/miR-370 | 0.78 | 0.85 | <1.00E−5 |
| miR-335-5p/miR-9 | 0.74 | 0.79 | <5.00E−4 |
| miR-132/miR-9 | 0.76 | 0.78 | <1.00E−3 |
| miR-132/miR-451 | 0.71 | 0.72 | <1.00E−2 |
| miR-335-5p/miR-7 | 0.78 | 0.80 | <2.00E−3 |
| miR-134/miR-410 | 0.86 | 0.88 | <1.00E−4 |

TABLE 26

Biomarker miRNA pair combinations for early (pre-MCI/MCI) AD detection

| miRNA pairs | Accuracy | AUC |
|---|---|---|
| miR-134/miR-127 + miR-323-3p/miR-433 + miR-323-3p/miR-127 + miR-323-3p/miR-370 | 0.85 | 0.89 |
| miR-323-3p/miR-370 + miR-323-3p/miR-433 + miR-134/miR-370 + miR-323-3p/miR-127 | 0.85 | 0.89 |
| miR-323-3p/miR-370 + miR-323-3p/miR-433 + miR-134/miR-370 + miR-335-5p/miR-9 | 0.86 | 0.91 |
| miR-132/miR-9 + miR-132/miR-451 + miR-335-5p/miR-7 | 0.78 | 0.8 |

Pairs: miR-323-3p/miR-127-3p, miR-323-3p/miR-433, miR134/miR-370, miR-335-5p/miR-7, miR-134/miR-410, miR-134/miR-127-3p, miR-335-5p/miR-9, miP-132/miR-451, miR-323-3p/miR-370; miR-132/miR-9, miR-135a/miR-9.

Combinations of miRNA pairs: miR-323-3p/miR-433+miR-323-3p/miR-127-3p; miR-134/miR-127-3p+miR-323-3p/miR-433+miR-323-3p/miR-127-3p+miR-323-3p/miR-370; miR-134/miR-370+miR-323-3p/miR-433+miR-323-3p/miR-127+miR-323-3p/370; miR-323-3p/370+miR-323-3p/miR-433+miR-134/miR-370+miR-335-5p/miR-9; miR-132/miR-9+miP-132/miR-451+miR-335-5p/miR-7; miR-132/miR-9+miR-135a/miR-9+miR-335-5p/miR-7; miR-134/miR-410+miR-323-3p/miR-127-3p; miR-134/miR-410+miR-323-3p/miR-127-3p.

Example 6. Pathology Detection in a Pre-Symptomatic Stage and Differentiation of Future AD from Other MCI/NDs Plasma samples were obtained from 84 subjects (42 males and 42 females) collected between 1988 and 2012 with CDR 0 at the time of blood collection. Later 42 subjects progressed to CDR>0 (progressors), and 42 subjects remained cognitively normal (non-progressors). Information on CSF Aβ$_{42}$ levels at the time of blood collection was available for 77 subjects.

TABLE 27 miRNAs tested for differentiation of progressors from non-progressors.

|  | miRNA | Brain enrichment | Present in synapses |
|---|---|---|---|
| 1 | Let-7e | Cer, MB, PG | + |
| 2 | miR-7 | PG, FC, Hip | + |
| 3 | miR-9 | FC, MB, Hip, Cer |  |
| 4 | miR-107 | FC, PG, Hip, MB |  |
| 5 | miR-127-3p | PG, MB, FC | + |
| 6 | miR-128a | Hip, FC, HT | + |
| 7 | miR-132 | PG, Hip | + |
| 8 | miR-134 | MB, Hip, PG | + |
| 9 | miR-135a | PG, Hip | + |
| 10 | miR-153 | Hip, FC |  |
| 11 | miR-181a | MB, FC |  |
| 12 | miR-184 | Hip, PG |  |
| 13 | miR-323-3p | FC, Hip, MB | + |
| 14 | miR-335-5p | PG, Hip |  |
| 15 | miR-370 | FC, PG | + |
| 16 | miR-382 | Hip, FC | + |
| 17 | miR-410 | PG, MB |  |
| 18 | miR-411 | PG, Hip, FC |  |
| 19 | miR-433 | PG, MB | + |
| 20 | miR-451 | Ubiquitous/PG, MB, |  |
| 21 | miR-485-5p | Hip | + |
| 22 | miR-488 | Hip, Cer |  |
| 23 | miR-491-5p | MB, FC | + |
| 24 | miR-874 | Cer, Hip | + |

Cer—Cerebellum;
FC—Frontal Cortex;
Hip—Hippocampus;
HT—Hypothalamus;
MB—Midbrain;
PG—Pituitary Gland.

RNA extraction, measurement of concentrations of 24 pre-selected miRNA (Table 27) in each sample by single target RT-qPCR and data analysis were performed as described above. Tables 28 and 29A-B present lists of miRNA pairs and their combinations capable of differentiating future progressors from non-progressors.

TABLE 28 miRNA pairs differentiating all progressors from all non-progressors

| miRNA pairs | Accuracy | AUC | P-Value |
|---|---|---|---|
| miR-181a/miR-370 | 0.63 | 0.68 | <4.80E−03 |
| miR-335/miR-370 | 0.57 | 0.65 | <2.30E−02 |
| miR-335/let-7e | 0.58 | 0.65 | <2.10E−02 |
| miR-135a/miR-370 | 0.6 | 0.64 | <3.00E−02 |
| miR-132/miR-370 | 0.6 | 0.64 | <2.60E−02 |
| miR-128a/miR-370 | 0.63 | 0.66 | <1.20E−02 |
| miR-128a/let-7e | 0.6 | 0.67 | <1.20E−02 |
| miR-107/miR-370 | 0.62 | 0.65 | <1.50E−02 |
| miR-410/miR-370 | 0.63 | 0.73 | <5.50E−04 |
| miR-410/miR-433 | 0.63 | 0.68 | <6.10E−03 |
| miR-411/miR-370 | 0.64 | 0.69 | <3.70E−03 |
| miR-382/miR-370 | 0.67 | 0.7 | <2.40E−03 |
| miR-323-3p/miR-370 | 0.64 | 0.7 | <1.70E−03 |
| miR-127/miR-370 | 0.67 | 0.68 | <6.60E−03 |
| miR-134/miR-370 | 0.61 | 0.69 | <4.70E−03 |
| miR-433/miR-370 | 0.6 | 0.66 | <1.50E−02 |

TABLE 29A

Combinations of 4 miRNA pairs differentiating all progressors from all non-progressors.

| miRNA pairs | Accuracy | AUC |
|---|---|---|
| miR-410/miR-370 + miR-181a/miR-370 + miR-127/miR-370 + miR-128a/let-7e | 0.73 | 0.8 |
| miR-323-3p/miR-370 + miR-127/miR-370 + miR-128a/let-7e | 0.75 | 0.79 |
| miR-323-3p/miR-370 + miR-181a/miR-370 + miR-127/miR-370 + miR-128a/let-7e | 0.76 | 0.8 |
| miR-323-3p/miR-370 + miR-127/miR-370 + miR-107/miR-370 + miR-335/let-7e | 0.71 | 0.79 |

TABLE 29A-continued

Combinations of 4 miRNA pairs differentiating all progressors from all non-progressors.

| miRNA pairs | Accuracy | AUC |
|---|---|---|
| miR-411/miR-370 + miR-181a/miR-370 + miR-127/miR-370 + miR-128a/let-7e | 0.75 | 0.79 |
| miR-410/miR-433 + miR-127/miR-370 + miR-128a/let-7e + miR-433/miR-370 | 0.7 | 0.8 |

TABLE 29B

Combinations of 3 miRNA pairs differentiating all progressors from all non-progressors.

| miRNA pairs | Accuracy | AUC |
|---|---|---|
| miR-410/miR-370 + miR-181a/miR-370 + miR-128a/let-7e | 0.69 | 0.78 |
| miR-410/miR-370 + miR-127/miR-370 + miR-128a/let-7e | 0.71 | 0.78 |
| miR-323-3p/miR-370 + miR-181a/miR-370 + miR-128a/let-7e | 0.69 | 0.78 |
| miR-323-3p/miR-370 + miR-127/miR-370 + miR-128a/let-7e | 0.75 | 0.79 |
| miR-323-3p/miR-370 + miR-127/miR-370 + miR-335/let-7e | 0.71 | 0.78 |
| miR-382/miR-370 + miR-127/miR-370 + miR-128a/let-7e | 0.73 | 0.77 |
| miR-411/miR-370 + miR-127/miR-370 + miR-128a/let-7e | 0.74 | 0.77 |
| miR-411/miR-370 + miR-127/miR-370 + miR-335/let-7e | 0.74 | 0.78 |
| miR-181a/miR-370 + miR-127/miR-370 + miR-128a/let-7e | 0.76 | 0.78 |
| miR-410/miR-433 + miR-127/miR-370 + miR-128a/let-7e | 0.69 | 0.77 |

Pairs: miR-181a/miR-370, miR-335-5p/miR-370, miR-335-5p/let-7e, miR-135a/miR-370, miR-132/miR-370, miR-128a/miR-370, miR-128a/let-7e, miR-107/miR-370, miR-410/miR-370, miR-410/miR-433, miR-411/miR-370, miR-382/miR-370, miR-323-3p/miR-370, miR-127/miR-370, miR-134/miR-370, miR-433/miR-370.

Combinations of miRNA pairs: miR-410/miR-370+miR-181a/miR-370+miR-127/miR-370+miR-128a/let-7e; miR-323-3p/miR-370+miR-127/miR-370+miR-128a/let-7e; miR-323-3p/miR-370+miR-181a/miR-370+miR-127/miR-370+miR-128a/let-7e; miR-323-3p/miR-370+miR-127/miR-370+miR-107/miR-370+miR-335-5p/let-7e; miR-411/miR-370+miR-181a/miR-370+miR-127/miR-370+miR-128a/let-7e; miR-410/miR-433+miR-127/miR-370+miR-128a/let-7e+miR-433/miR-370; miR-410/miR-370+miR-181a/miR-370+miR-128a/let-7e; miR-410/miR-370+miR-127/miR-370+miR-128a/let-7e; miR-323-3p/miR-370+miR-181a/miR-370+miR-128a/let-7e; miR-323-3p/miR-370+miR-127/miR-370+miR-128a/let-7e; miR-323-3p/miR-370+miR-12 miR-370+miR-335-5p/let-7e; miR-382/miR-370+miR-127/miR-370+miR-128a/let-7e; miR-411/miR-370+miR-127/miR-370+miR-128a/let-7e; miR-411/miR-370+miR-127/miR-370+miR-335-5p/let-7e; miR-181a/miR-370+miR-127/miR-370+miR-128a let-7e; miR-410/miR-433+miR-127/miR-370+miR-128a/let-7e.

In addition, ability of biomarker miRNA pairs to differentiate future $A\beta_{42}$ positive progressors (potential AD) from $A\beta_{42}$ negative progressors (potentially other NDs) was analyzed. Tables 30 and 31A,B present lists miRNA pairs and their combinations capable of differentiating future $A\beta_{42}$ positive and $A\beta_{42}$ negative progressors from each other.

TABLE 30 miRNA pairs differentiating future $A\beta_{42}$ positive progressors (potential AD) from $A\beta_{42}$ negative progressors (potentially other NDs).

| miRNA pairs | Accuracy | AUC | P-Value |
|---|---|---|---|
| miR-382/miR-134 | 0.73 | 0.74 | <3.30E−02 |
| miR-135a/miR-181a | 0.7 | 0.71 | <4.00E−02 |
| miR-323-3p/miR-410 | 0.68 | 0.71 | <9.60E−02 |
| miR-135a/let-7e | 0.68 | 0.7 | <4.30E−02 |
| miR-135a/miR-433 | 0.68 | 0.7 | <6.70E−02 |
| miR-335/let-7e | 0.65 | 0.7 | <5.20E−02 |
| miR-335/miR-107 | 0.65 | 0.7 | <9.60E−02 |
| miR-323-3p/miR-433 | 0.65 | 0.7 | <8.10E−02 |
| miR-128a/let-7e | 0.7 | 0.7 | <7.20E−02 |
| miR-135a/miR-874 | 0.68 | 0.69 | <8.10E−02 |
| miR-135a/miR-132 | 0.68 | 0.69 | <6.70E−02 |
| miR-323-3p/miR-134 | 0.73 | 0.69 | <6.00E−02 |
| miR-370/miR-433 | 0.68 | 0.69 | <7.20E−02 |
| miR-411/miR-433 | 0.65 | 0.69 | <6.30E−02 |
| miR-135a/miR-127 | 0.65 | 0.68 | <9.00E−02 |
| miR-135a/miR-134 | 0.68 | 0.68 | <9.00E−02 |
| miR-135a/miR-410 | 0.68 | 0.68 | <8.50E−02 |

TABLE 31A

Combinations of 4 miRNA pairs differentiating future $A\beta_{42}$ positive progressors (potential AD) from $A\beta_{42}$ negative progressors (potentially other NDs).

| miRNA pairs | Accuracy | AUC |
|---|---|---|
| miR-382/miR-134 + miR-135a/miR-181a + miR-128a/let-7e + miR-335/miR-107 | 0.81 | 0.88 |
| miR-382/miR-134 + miR-128a/let-7e + miR-135a/miR-874 | 0.78 | 0.86 |
| miR-382/miR-134 + miR-135a/miR-181a + miR-128a/let-7e + miR-135/miR-874 | 0.81 | 0.87 |
| miR-382/miR-134 + miR-128a/let-7e + miR-335/miR-107 + miR-135a/miR-874 | 0.84 | 0.88 |
| miR-382/miR-134 + miR-135a/miR-181a + miR-335/let-7e + miR-370/miR-433 | 0.84 | 0.88 |
| miR-382/miR-134 + miR-135a/miR-181a + miR-128a/let-7e + miR-370/miR-433 | 0.84 | 0.87 |
| miR-382/miR-134 + miR-135a/let-7e + miR-128a/let-7e + miR-370/miR-433 | 0.84 | 0.88 |
| miR-382/miR-134 + miR-335/let-7e + miR-135a/miR-433 + miR-370/miR-433 | 0.84 | 0.88 |
| miR-382/miR-134 + miR-135a/miR-181a + miR-370/miR-433 + miR-135a/miR-134 | 0.76 | 0.88 |
| miR-382/miR-134 + miR-335/let-7e + miR-370/miR-433 + miR-135a/miR-134 | 0.84 | 0.9 |
| miR-382/miR-134 + miR-128a/let-7e + miR-370/miR-433 + miR-135a/miR-134 | 0.84 | 0.9 |
| miR-382/miR-134 + miR-335/let-7e + miR-370/miR-433 + miR-135a/miR-127 | 0.84 | 0.88 |
| miR-382/miR-134 + miR-335/let-7e + miR-370/miR-433 + miR-135a/miR-410 | 0.81 | 0.88 |
| miR-382/miR-134 + miR-128a/let-7e + miR-370/miR-433 + miR-135a/miR-410 | 0.78 | 0.89 |

TABLE 31B

Combinations of 3 miRNA pairs differentiating future $A\beta_{42}$ positive progressors (potential AD) from $A\beta_{42}$ negative progressors (potentially other NDs).

| miRNA pairs | Accuracy | AUC |
|---|---|---|
| miR-382/miR-134 + miR-135a/miR-181a + miR-323-3p/miR-410 | 0.81 | 0.84 |
| miR-382/miR-134 + miR-335/let-7e | 0.78 | 0.84 |
| miR-382/miR-134 + miR-135a/miR-181a + miR-335/let-7e | 0.76 | 0.85 |
| miR-382/miR-134 + miR-135a/miR-181a + miR-128a/let-7e | 0.73 | 0.85 |

TABLE 31B-continued

Combinations of 3 miRNA pairs differentiating future Aβ42 positive progressors (potential AD) from Aβ42 negative progressors (potentially other NDs).

| miRNA pairs | Accuracy | AUC |
|---|---|---|
| miR-382/miR-134 + miR-135a/let-7e + miR-128a/let-7e | 0.81 | 0.85 |
| miR-382/miR-134 + miR-335/let-7e + miR-135a/miR-433 | 0.81 | 0.84 |
| miR-382/miR-134 + miR-128a/let-7e + miR-135a/miR-874 | 0.78 | 0.86 |
| miR-382/miR-134 + miR-135a/miR-181a + miR-370/miR-433 | 0.81 | 0.86 |
| miR-382/miR-134 + miR-335/let-7e + miR-370/miR-433 | 0.78 | 0.86 |
| miR-382/miR-134 + miR-323-3p/miR-410 + miR-135a/miR-132 | 0.84 | 0.84 |
| miR-135a/let-7e + miR-128a/let-7e + miR-370/miR-433 | 0.78 | 0.84 |
| miR-128a/let-7e + miR-370/miR-433 + miR-135a/miR-134 | 0.78 | 0.84 |

Pairs: miR-382/miR-134, miR-135a/miR-181a, miR-323-3p/miR-410, miR-135a/let-7e, miR-135a/miR-433, miR-335-5p/let-7e, miR-335-5p/miR-107, miR-323-3p/miR-433, miR-128a/let-7e, miR-135a/miR-874, miR-135a/miR-132, miR-323-3p/miR-134, miR-370/miR-433, miR-411/miR-433, miR-135a/miR-127, miR-135a/miR-134, miR-135a/miR-410.

Combinations of miRNA pairs: miR-382/miR-134+miR-135a/miR-181a+miR-128a/let-7e+miR-335-5p/miR-107, miR-382/miR-134+miR-128a/let-7e+miR-135a/miR-874, miR-382/miR-134+miR-135a/miR-181a+miR-128a/let-7e+miR-135a/miR-874, miR-382/miR-134+miR-128a/let-7e+miR-335-5p/miR-107+miR-135a/miR-874, miR-382/miR-134+miR-135a/miR-181a+miR-335-5p/let-7e+miR-370/miR-433, miR-382/miR-134+miR-135a/miR-181a+miR-128a/let-7e+miR-370/miR-433, miR-382/miR-134+miR-135a/let-7e+miR-128a/let-7e+miR-370/miR-433, miR-382/miR-134+miR-335-5p/let-7e+miR-135a/miR-433+miR-370/miR-433, miR-382/miR-134+miR-135a/miR-181a+miR-370/miR-433+miR-135a/miR-134, miR-382/miR-134+miR-335-5p/let-7e+miR-370/miR-433+miR-135a/miR-134, miR-382/miR-134+miR-128a/let-7e+miR-370/miR-433+miR-135a/miR-134, miR-382/miR-134+miR-335-5p/let-7e+miR-370/miR-433+miR-135a/miR-127, miR-382/miR-134+miR-335-5p/let-7e+miR-370/miR-433+miR-135a/miR-410, miR-382/miR-134+miR-128a/let-7e+miR-370/miR-433+miR-135a/miR-410; miR-382/miR-134+miR-135a/miR-181a+miR-323-3p/miR-410, miR-382/miR-134+miR-135a/miR-181a+miR-335-5p/let-7e, miR-382/miR-134+miR-135a/miR-181a+miR-128a/let-7e, miR-382/miR-134+miR-135a/let-7e+miR-128a/let-7e, miR-382/miR-134+miR-335-5p/let-7e+miR-135a/miR-433, miR-382/miR-134+miR-128a/let-7e+miR-135a/miR-874, miR-382/miR-134+miR-135a/miR-181a+miR-370/miR-433, miR-382/miR-134+miR-335-5p/let-7e+miR-370/miR-433, miR-382/miR-134+miR-323-3p/miR-410+miR-135a/miR-132, miR-135a/let-7e+miR-128a/let-7e+miR-370/miR-433, miR-128a/let-7e+miR-370/miR-433+miR-135a/miR-134.

Interestingly, some miRNA pairs and their combinations (Table 32 and Table 33A,B) effectively distinguished future Aβ42 positive progressors from Aβ42 positive non-progressors.

TABLE 32 miRNA pairs differentiating future Aβ42 positive progressors from Aβ42 positive non-progressors.

| miRNA pairs | Accuracy | AUC | P-Value |
|---|---|---|---|
| miR-128a/let-7e | 0.74 | 0.74 | <1.40E-02 |
| miR-411/miR-485-5p | 0.67 | 0.72 | <2.10E-02 |
| miR-135a/miR-485-5p | 0.71 | 0.72 | <2.40E-02 |
| miR-874/let-7e | 0.69 | 0.7 | <3.40E-02 |
| miR-135a/let-7e | 0.64 | 0.69 | <4.20E-02 |
| miR-410/miR-433 | 0.69 | 0.69 | <4.70E-02 |
| miR-382/miR-370 | 0.76 | 0.7 | <5.00E-02 |
| miR-411/miR-370 | 0.69 | 0.69 | <5.50E-02 |
| miR-132/let-7e | 0.69 | 0.7 | <5.80E-02 |
| miR-323-3p/miR-485-5p | 0.69 | 0.69 | <6.10E-02 |
| miR-135a/miR-134 | 0.67 | 0.67 | <6.40E-02 |
| miR-382/miR-485-5p | 0.67 | 0.69 | <6.40E-02 |

TABLE 33A

Combinations of 4 miRNA pairs differentiating future Aβ42 positive progressors from Aβ42 positive non-progressors.

| miRNA pairs | Accuracy | AUC |
|---|---|---|
| miR-128a/let-7e + miR-135a/miR-485-5p + miR-411/miR-485-5p + miR-382/miR-370 | 0.76 | 0.85 |
| miR-128a/let-7e + miR-135a/miR-485-5p + miR-411/miR-485-5p + miR-410/miR-433 | 0.76 | 0.84 |
| miR-128a/let-7e + miR-135a/miR-485-5p + miR-410/miR-433 + miR-323-3p/miR-485-5p | 0.76 | 0.83 |
| miR-128a/let-7e + miR-411/miR-485-5p + miR-382/miR-370 + miR-135a/miR-134 | 0.79 | 0.84 |
| miR-128a/let-7e + miR-411/miR-485-5p + miR-410/miR-433 + miR-135a/miR-134 | 0.74 | 0.86 |
| miR-128a/let-7e + miR-410/miR-433 + miR-323-3p/miR-485-5p + miR-135a/miR-134 | 0.79 | 0.84 |
| miR-135a/miR-485-5p + miR-411/miR-485-5p + miR-410/miR-433 | 0.79 | 0.84 |
| miR-135a/miR-485-5p + miR-411/miR-485-5p + miR-410/miR-433 + miR-135a/miR-134 | 0.79 | 0.85 |
| miR-411/miR-485-5p + miR-382/miR-370 + miR-135a/let-7e + miR-323-3p/miR-485-5p | 0.81 | 0.83 |

TABLE 33B

Combinations of 3 miRNA pairs differentiating future Aβ42 positive progressors from Aβ42 positive non-progressors.

| miRNA pairs | Accuracy | AUC |
|---|---|---|
| miR-128a/let-7e + miR-135a/miR-485-5p + miR-411/miR-485-5p | 0.79 | 0.82 |
| miR-128a/let-7e + miR-411/miR-485-5p + miR-410/miR-433 | 0.74 | 0.81 |
| miR-128a/let-7e + miR-382/miR-370 + miR-323-3p/miR-485-5p | 0.76 | 0.82 |
| miR-128a let-7e + miR-410/miR-433 + miR-323-3p/miR-485-5p | 0.76 | 0.82 |
| miR-128a/let-7e + miR-411/miR-485-5p + miR-135a/miR-134 | 0.76 | 0.81 |
| miR-135a/miR-485-5p + miR-411/miR-485-5p + miR-410/miR-433 | 0.79 | 0.84 |
| miR-135a/miR-485-5p + miR-411/miR-485-5p + miR-135a/let-7e | 0.74 | 0.83 |
| miR-135a/miR-485-5p + miR-382/miR-370 + miR-323-3p/miR-485-5p | 0.71 | 0.81 |
| miR-411/miR-485-5p + miR-410/miR-433 + miR-135a/miR-134 | 0.81 | 0.86 |
| miR-411/miR-485-5p + miR-135a/let-7e + miR-135a/miR-134 | 0.74 | 0.82 |
| miR-410/miR-433 + miR-323-3p/miR-485-5p + miR-135a/miR-134 | 0.74 | 0.82 |

Pairs: miR-128a/let-7e, miR-411/miR-485-5p, miR-135a/miR-485-5p, miR-874/let-7e, miR-135a/let-7e, miR-410/miR-433, miR-382/miR-370, miR-411/miR-370, miR-132/let-7e, miR-323-3p/miR-485-5p, miR-135a/miR-134, miR-382/miR-485-5p.

Combinations of miRNA pairs: miR-128a/let-7e+miR-135a/miR-485-5p+miR-411/miR-485-5p+miR-382/miR-370, miR-128a/let-7e+miR-135a/miR-485-5p+miR-411/miR-485-5p+miR-410/miR-433, miR-128a/let-7e+miR-135a/miR-485-5p+miR-410/miR-433+miR-323-3p/miR-485-5p, miR-128a/let-7e+miR-411/miR-485-5p+miR-382/miR-370+miR-135a/miR-134, miR-128a/let-7e+miR-411/miR-485-5p+miR-410/miR-433+miR-135a/miR-134, miR-128a/let-7e+miR-410/miR-433+miR-323-3p/miR-485-5p+miR-135a/miR-134, miR-135a/miR-485-5p+miR-411/miR-485-5p+miR-410/miR-433, miR-135a/miR-485-5p+miR-411/miR-485-5p+miR-410/miR-433+miR-135a/miR-134, miR-411/miR-485-5p+miR-382/miR-370+miR-135a/let-7e+miR-323-3p/miR-485-5p; miR-128a/let-7e+miR-135a/miR-485-5p+miR-411/miR-485-5p, miR-128a/let-7e+miR-411/miR-485-5p+miR-410/miR-433, miR-128a/let-7e+miR-382/miR-370+miR-323-3p/miR-485-5p, miR-128a let-7e+miR-410/miR-433+miR-323-3p/miR-485-5p, miR-128a/let-7e+miR-411/miR-485-5p+miR-135a/miR-134, miR-135a/miR-485-5p+miR-411/miR-485-5p+miR-410/miR-433, miR-135a/miR-485-5p+miR-411/miR-485-5p+miR-135a/let-7e, miR-135a/miR-485-5p+miR-382/miR-370+miR-323-3p/miR-485-5p, miR-411/miR-485-5p+miR-410/miR-433+miR-135a/miR-134, miR-411/miR-485-5p+miR-135a/let-7e+miR-135a/miR-134, miR-410/miR-433+miR-323-3p/miR-485-5p+miR-135a/miR-134.

Example 7: Gender-Dependence of Neurodegenerative Disease Biomarkers

Three studies were performed to find out if miRNA biomarkers for detection of neurodegenerative diseases (ND) are gender-dependent and if the assay accuracy can be increased by comparison of ND and control cohorts for male and female subjects separately.

In the first study, early Alzheimer's disease (AD) CDR>0 Aβ42 positive subjects were compared with CDR 0, Aβ negative controls.

In the second study, a primary objective was to test circulating brain-enriched miRNA biomarkers for their ability to recognize those cognitively normal subjects who will progress to AD or other dementia with and without amyloid pathology at clinically asymptomatic stage.

The present inventors also tested if there is a gender specificity component in the ability of miRNA pairs to differentiate early AD from control (the first study) and 'progressors' from 'non-progressors' (the second study). Table 34 demonstrates that separate comparison of male and female subjects in both cases differentiates these cohorts with higher accuracy. This is a very important observation, indicating that gender-specific testing significantly increases assay sensitivity. These results also indicate that some AD-related (and, maybe other processes) in the brain are gender-specific, which can be registered by analysis of brain-enriched miRNAs in plasma.

TABLE 34

Gender dependence of biomarker miRNA pair ability to differentiate early AD from control

| Study | Cohorts | Sample Path size | Sample Ctrl size | miRNA pairs | AUC | Accuracy % |
|---|---|---|---|---|---|---|
| CDR > 0 (Path) Versus CDR 0 (Ctrl) | Male and Female Combined | 29 | 30 | miR-134/miR-433 + miR-323/miR-370 + miR-323/miR-127 | 0.89 | 83 |
| | Male | 16 | 14 | miR-132/miR-433 + miR-132/miR-7 + miR-874/miR-9 | 1 | 100 |
| | Female | 13 | 16 | miR-135a/miR-433 + miR-323/miR-433 + miR-323/miR-127 | 0.97 | 90 |
| Progressors (Path) Versus Non-Progressors (Ctrl) | Male and Female Combined | 38 | 40 | miR-323/miR-485 + miR-410/miR-370 + miR-323/miR-7 | 0.88 | 78 |
| | Male | 17 | 20 | miR-323/miR-485 + miR-410/miR-485 | 0.88 | 84 |
| | Female | 21 | 20 | miR-323/miR-433 + miR-323/miR-411 + miR-128a/miR-7 | 0.98 | 95 |

In the third study, the present inventors tested whether separate analysis of male and female subjects could affect the accuracy of differentiation of various NDs from age-matched controls. Three cohort pairs (ND versus control) were compared for AD, FTD, PD and ALS:

1. Combined male and female ND versus combined controls;

2. Male ND versus male control;

3. Female ND versus female control.

Table 35A compares one of the best biomarker miRNA combinations for differentiating each ND from Control in three cohort pairs: all ND vs all Controls, male ND vs male Controls, and female ND vs female Controls. There are no significant differences of AUC and Accuracy between these groups for each ND, which means that these miRNAs behave similarly in Controls and ND of males and females. Table 35B shows the best biomarker miRNA combinations for ND vs. control gender-specific cohort pairs. In this case, both AUC and Accuracy are significantly higher when compared to best panels for combined (male and female) cohorts. Interestingly, only some miRNAs (numerators, denominators or both depending on ND) are different in these biomarker miRNA combinations of gender-specific cohorts.

TABLE 35

Gender-dependence of NDs differentiation from Controls by various miRNA pair combinations A. Biomarker miRNA pairs most, which effectively differentiated ND from Control in mixed (male + female) combined training and confirmation sets.

| Gender | miRNA pairs | AD-CNTR miR-99b/miR-181a + miR-9*/miR-874 + miR-7/miR-16 | FTD-CNTR miR-335/let-7e + miR-99b/let-7e + miR-9*/miR-181a | PD-CNTR miR-9*/miR-129-3p + miR-99b/miR-874 + miR-9*/miR-411 | ALS-CNTR miR-206/miR-31 + miR-206/miR-125b + miR-99/miR-338-3p |
|---|---|---|---|---|---|
| Male + Female | AUC | 0.97 | 0.94 | 0.96 | 0.95 |
| | Accuracy | 0.91 | 0.91 | 0.86 | 0.83 |
| Male | AUC | 0.98 | 0.98 | 0.96 | 0.94 |
| | Accuracy | 0.92 | 0.94 | 0.88 | 0.9 |
| Female | AUC | 0.97 | 0.91 | 0.96 | 0.95 |
| | Accuracy | 0.9 | 0.88 | 0.85 | 0.83 |

B. Biomarker miRNA pairs, which most effectively differentiated ND from Control in male or female cohorts.

| | miRNA pairs | AD-CNTR miR-99b/miR-181a + miR-125/miR-874 + miR-9*/miR-29a | FTD-CNTR miR-335/let-7e + miR-99b/let-7e + miR-9*/miR-181a | PD-CNTR miR-9*/miR-129-3p + miR-99b/miR-146a + miR-9*/miR-204 | ALS-CNTR miR-206/miR-155 + miR-9*/miR-129-3p + miR-335/miR-338-3p |
|---|---|---|---|---|---|
| Male | AUC | 0.99 | 0.98 | 0.98 | 0.99 |
| | Accuracy | 0.94 | 0.94 | 0.92 | 0.92 |

| | miRNA pairs | miR-99b/miR-181a + miR-9*/miR-874 + miR-7/miR-451 | miR-491/let-7e + miR-107/miR-9 + miR-28/miR-181a | miR-9*/miR-29a + miR-99b/miR-874 + miR-491/let-7e | miR-206/miR-7 + miR-9*/miR-125b + miR-491/miR-204 |
|---|---|---|---|---|---|
| Female | AUC | 0.99 | 0.98 | 0.99 | 0.99 |
| | Accuracy | 0.96 | 0.92 | 0.95 | 0.98 |

Taken together, these data indicate that gender-specific assays can be used for diagnosis of NDs both in early, even asymptomatic stage, and in developed late stage with higher accuracy and demonstrate gender-specific differences in brain-enriched miRNA expression.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for detecting a neurodegenerative disorder (ND) in a subject, which method comprises:
    a) measuring the level of a first miRNA in a bodily fluid sample collected from the subject;
    b) measuring the level of a second miRNA in the same bodily fluid sample collected from the subject;
    c) calculating the ratio of the level of the first miRNA (numerator) measured in step (a) to the level of the second miRNA (denominator) measured in step (b);
    d) comparing the numerator/denominator miRNA ratio calculated in step (c) with a control ratio, wherein the control ratio (i) is a predetermined value which represents a statistically validated threshold ratio of the levels of said first and second miRNAs equal to the highest possible value within the range of values in matched healthy subjects, or is (ii) the ratio of the levels of said first and second miRNAs in a bodily fluid sample from the same subject collected in the past,
    e) identifying the subject as being afflicted with the ND based on the detection of a higher numerator/denominator miRNA ratio calculated in step (c) as compared to the control ratio, and
    f) administering a therapeutic agent to the subject identified as afflicted with ND,
    wherein
    the ND is frontotemporal dementia (FTD) and the first miRNA is miR-335-5p and the second miRNA is let-7e, and the therapeutic agent is selected from an anti-psychotic, an anti-depressant, *Gingko biloba*, vitamin B12, folic acid, and any combinations thereof, or
    the ND is amyotrophic lateral sclerosis (ALS) and the first miRNA is miR-99b and the second miRNA is miR-338-3p, and the therapeutic agent is selected from riluzole, omigapil, creatine, Vitamin E, and any combinations thereof.

2. The method of claim 1, wherein the anti-psychotic is selected from olanzepine, quetiapine, risperidone, ziprasidone, aripiprazole, and paliperidone.

3. The method of claim 1, further comprising recruiting the subject in a clinical trial.

4. The method of claim 1, wherein the neurodegenerative disorder (ND) is frontotemporal dementia (FTD), and the method comprises measuring one or more additional numerator/denominator miRNA ratios selected from miR- 9*/miR-181a, miR-9*/miR-874, miR-9*/miR-125b, miR-9*/let-7e, miR-9*/miR-155, miR-99b/miR-181a, miR-99b/let-7e, miR-128a/miR-181a, miR-9*/miR-31, miR-9*/miR-146a, miR-9*/miR-9, miR-323-3p/miR-134, miR-338-3p/miR-181a, miR-491-5p/let-7e, miR-128a/miR-874, miR-128a/let-7e, miR-7/miR-874, miR-7/miR-125b, miR-338-3p/let-7e, miR-335-5p/miR-181a, miR-335-5p/miR-9, miR-107/miR-9, and miR-335-5p/miR-146a.

5. The method of claim 4, wherein the subject is a male, and the method comprises measuring a combination of numerator/denominator miRNA ratios miR-335-5p/let-7e+miR-99b/let-7e+miR-9*/miR-181a.

6. The method of claim 4, wherein the subject is a female, and the method comprises measuring a combination of numerator/denominator miRNA ratios miR-491-5p/let-7e+miR-107/miR-9+miR-128a/miR-181a.

7. The method of claim 1, wherein the neurodegenerative disorder (ND) is amyotrophic lateral sclerosis (ALS), and the method comprises measuring one or more additional numerator/denominator miRNA ratios selected from miR-206/miR-31, miR-206/miR-129-3p, miR-206/miR-138, miR-206/miR-874, miR-206/miR-125b, miR-206/miR-204, miR-206/miR-29a, miR-206/miR-155, miR-206/miR-338-3p, miR-206/miR-16, miR-206/miR-451, miR-206/miR-218, miR-99b/miR-9, miR-99b/miR-155, miR-9*/miR-129-3p, miR-99b/miR-155, miR-99b/let-7e, miR-181a/miR-338-3p, miR-335-5p/miR-338-3p, miR-7/miR-31, miR-7/miR-129-3p, miR-9*/miR-129-3p, miR-9*/miR-338-3p, miR-99b/miR-338-3p, miR-99b/miR-128a, miR-206/miR-7, miR-9*/miR-125b, miR-491-5p/miR-204, and miR-335-5p/let-7e.

8. The method of claim 7, wherein the subject is a male, and the method comprises measuring a combination of numerator/denominator miRNA ratios miR-206/miR-155+miR-9*/miR-129-3p+miR-335-5p/miR-338-3p.

9. The method of claim 7, wherein the subject is a female, and the method comprises measuring a combination of numerator/denominator miRNA ratios miR-206/miR-7+miR-9*/miR-125b+miR-491-5p/miR-204.

10. The method of claim 1, further comprising differentiation between frontotemporal dementia (FTD) or amyotrophic lateral sclerosis (ALS) (first ND) and another neurodegenerative disorder selected from Alzheimer's disease (AD), Parkinson's disease (PD), FTD, and ALS (second ND), which differentiation comprises:
g) measuring the level of a third miRNA in a bodily fluid sample collected from the subject;
h) measuring the level of a fourth miRNA in the same bodily fluid sample collected from the subject;
i) calculating the ratio of the level of the third miRNA (numerator) measured in step (g) to the level of the fourth miRNA (denominator) measured in step (h);
j) comparing the numerator/denominator miRNA ratio calculated in step (i) with (1) the standard range of said numerator/denominator miRNA ratios characteristic of the first ND and with (2) the standard range of said numerator/denominator miRNA ratios characteristic of the second ND, wherein the standard range of said numerator/denominator miRNA ratios characteristic of said first or second ND is a statistically validated predetermined range of values established by determining the ratios of the levels of the same miRNAs in a large cohort of subjects diagnosed with said first or second ND;
k) (1) identifying the subject as being afflicted with the first ND if based on the comparison in step (j) the numerator/denominator miRNA ratio calculated in step (i) falls within the standard range of said numerator/denominator miRNA ratios characteristic of the first ND, or (2) identifying the subject as being afflicted with the second ND if based on the comparison in step (j) the numerator/denominator miRNA ratio calculated in step (i) falls within the standard range of said numerator/denominator miRNA ratios characteristic of the second ND,
wherein:
(1) the first ND is frontotemporal dementia (FTD) and the second ND is Parkinson's disease (PD), and the numerator/denominator miRNA ratio calculated in step (i) is selected from miR-218/miR-9*, miR-218/miR-99b, miR-138/miR-99b, miR-138/miR-181a, miR-138/miR-491-5p, miR-31/miR-9*, miR-31/miR-99b, miR-129-3p/miR-9*, miR-129-3p/miR-99b, miR-204/miR-9*, miR-204/miR-99b, miR-338-3p/miR-99b, miR-338-3p/miR-491-5p, miR-338-3p/miR-107, miR-338-3p/let-7e, miR-338-3p/miR-146a, miR-874/miR-99b, miR-125b/miR-99b, miR-29a/miR-99b, miR-323-3p/miR-127-3p, miR-411/miR-127-3p, miR-155/miR-99b, miR-335-5p/miR-99b, and miR-382/miR-134, or
(2) the first ND is frontotemporal dementia (FTD) and the second ND is amyotrophic lateral sclerosis (ALS), and the numerator/denominator miRNA ratio calculated in step (i) is selected from miR-31/miR-206, miR-138/miR-206, miR-29a/miR-206, miR-129-3p/miR-206, miR-204/miR-206, miR-338-3p/miR-206, miR-338-3p/let-7e, miR-7/miR-206, miR-128a/miR-206, miR-16/miR-206, miR-125b/miR-206, miR-874/miR-206, miR-218/miR-206, miR-29a/miR-155, miR-338-3p/miR-181a, miR-338-3p/miR-335-5p, miR-338-3p/miR-491-5p, miR-338-3p/miR-146a, miR-323-3p/miR-127-3p, and miR-129-3p/miR-9*, or
(3) the first ND is frontotemporal dementia (FTD) and the second ND is Alzheimer's disease (AD), and the numerator/denominator miRNA ratio calculated in step (i) is selected from miR-29a/miR-125b, miR-874/miR-125b, miR-335-5p/miR-107, miR-29a/miR-155, miR-874/miR-329, miR-181a/miR-329, miR-411/miR-329, miR-16/miR-7, miR-16/miR-451, miR-335-5p/miR-155, and miR-335-5p/let-7e, or
(4) the first ND is amyotrophic lateral sclerosis (ALS) and the second ND is Parkinson's disease (PD), and the numerator/denominator miRNA ratio calculated in step (i) is selected from miR-206/miR-329, miR-206/miR-9*, miR-206/miR-433, miR-206/miR-370, miR-206/miR-134, miR-206/miR-323-3p, miR-206/miR-9, miR-206/miR-99b, miR-206/miR-495, miR-206/miR-382, miR-206/miR-491-5p, miR-206/miR-29a, miR-206/miR-411, miR-206/miR-181a, miR-206/miR-155, miR-206/miR-146a, miR-206/miR-7, miR-204/miR-107, let-7e/miR-107, miR-335-5p/miR-107, miR-146a/miR-107, miR-874/miR-128a, let-7e/miR-128a, miR-382/miR-329, miR-382/miR-433, and miR-411/miR-433, or
(5) the first ND is amyotrophic lateral sclerosis (ALS) and the second ND is Alzheimer's disease (AD), and the numerator/denominator miRNA ratio calculated in step (i) is selected from miR-206/miR-329, miR-9*/miR-329, miR-99b/miR-329, miR-335-5p/miR-329, miR-146a/miR-329, miR-411/miR-329, miR-206/miR-31, miR-16/miR-31, miR-206/miR-129-3p, miR-16/miR-129-3p, miR-206/miR-433, miR-335-5p/miR-433, miR-206/miR-125b, miR-335-5p/miR-125b, miR-874/miR-125b, miR-206/miR-323-3p, miR-206/miR-495, miR-206/miR-204, miR-206/miR-127-3p, miR-206/ miR-107, miR-99b/miR-107, miR-335-5p/miR-107, let-7e/miR-107, miR-146a/miR-107, miR-491-5p/miR-107, miR-206/miR-138, miR-206/miR-134, miR-206/miR-9, miR-206/miR-155, miR-206/miR-7, miR-206/miR-338-3p, miR-206/miR-29a, let-7e/miR-338-3p, miR-411/miR-433, miR-382/miR-433, and miR-411/miR-127-3p, or (6) the first ND is amyotrophic lateral sclerosis (ALS) and the second ND is frontotemporal dementia (FTD), and the numerator/denominator miRNA ratio calculated in step (i) is selected from miR-206/miR-31, miR-206/miR-138, miR-206/miR-29a, miR-206/miR-129-3p, miR-206/miR-204, miR-206/miR-338-3p, let-7e/miR-338-3p, miR-206/miR-7, miR-206/miR-128a, miR-206/miR-16, miR-206/miR-125b, miR-206/miR-874, miR-206/miR-218, miR-155/miR-29a, miR-181a/miR-338-3p, miR-335-5p/miR-338-3p, miR-491-5p/miR-338-3p, miR-146a/miR-338-3p, miR-127-3p/miR-323-3p, and miR-9*/miR-129-3p.

11. A method for monitoring changes in development of a neurodegenerative disorder (ND) in a subject diagnosed with the ND, which method comprises:
   a) measuring the level of a first miRNA in two or more bodily fluid samples collected from the subject at spaced apart time points;
   b) measuring the level of a second miRNA in the same bodily fluid samples as in step (a);
   c) calculating the ratio of the level of the first miRNA (numerator) measured in step (a) to the level of the second miRNA (denominator) measured in step (b) for each bodily fluid sample;
   d) comparing the numerator/denominator miRNA ratios calculated in step (c) between the earlier collected and later collected bodily fluid sample(s),
   e) determining that the ND in the subject has progressed based on the detection of a higher numerator/denominator miRNA ratio determined in step (c) in the later collected bodily fluid sample(s) as compared to the earlier collected sample(s), and
   f) administering to the subject identified as having a progression of the ND a therapeutic agent to alleviate one or more of the symptoms of the ND or inhibit further development of the ND,
   wherein
   the ND is frontotemporal dementia (FTD) and the first miRNA is miR-335-5p and the second miRNA is let-7e, or
   the ND is amyotrophic lateral sclerosis (ALS) and the first miRNA is miR-99b and the second miRNA is miR-338-3p.

12. A method for monitoring the effect of a therapeutic agent on development of a neurodegenerative disorder (ND) in a subject diagnosed with the ND, which method comprises:
   a) collecting one or more bodily fluid sample(s) from the subject prior to the administration of the therapeutic agent,
   b) administering the therapeutic agent to the subject,
   c) collecting one or more bodily fluid sample(s) from the subject in the course of or following the administration of the therapeutic agent,
   d) measuring the level of a first miRNA and a second miRNA in the bodily fluid samples collected from the subject in steps (a) and (c);
   e) calculating the ratio of the level of the first miRNA (numerator) to the level of the second miRNA (denominator) measured in step (d);
   f) comparing the numerator/denominator miRNA ratio calculated in step (e) between the sample(s) obtained before the administration of the therapeutic agent and sample(s) obtained in the course of or following the administration of the therapeutic agent,
   g) determining that the therapeutic agent is effective for alleviating one or more symptoms of said ND or is effective for inhibition of further development of said ND based on the detection of an unchanged or decreased numerator/denominator miRNA ratio calculated in step (e) in the sample(s) obtained in the course of or following the administration of the therapeutic agent as compared to the sample(s) obtained before the administration of the therapeutic agent, and continuing to administer the therapeutic agent to the subject in which the therapeutic agent was determined to be effective,
   wherein
   the ND is frontotemporal dementia (FTD) and the first miRNA is miR-335-5p and the second miRNA is let-7e, or
   the ND is amyotrophic lateral sclerosis (ALS) and the first miRNA is miR-99b and the second miRNA is miR-338-3p.

13. The method of claim 11, wherein the neurodegenerative disorder (ND) is frontotemporal dementia (FTD), and the method comprises measuring one or more additional numerator/denominator miRNA ratios selected from miR-9*/miR-181a, miR-9*/miR-874, miR-9*/miR-125b, miR-9*/let-7e, miR-9*/miR-155, miR-99b/miR-181a, miR-99b/let-7e, miR-128a/miR-181a, miR-9*/miR-31, miR-9*/miR-146a, miR-9*/miR-9, miR-323-3p/miR-134, miR-338-3p/miR-181a, miR-491-5p/let-7e, miR-128a/miR-874, miR-128a/let-7e, miR-7/miR-874, miR-7/miR-125b, miR-338-3p/let-7e, miR-335-5p/miR-181a, miR-335-5p/miR-9, miR-107/miR-9, and miR-335-5p/miR-146a.

14. The method of claim 13, wherein the subject is a male, and the method comprises measuring a combination of numerator/denominator miRNA ratios miR-335-5p/let-7e+miR-99b/let-7e+miR-9*/miR-181a.

15. The method of claim 13, wherein the subject is a female, and the method comprises measuring a combination of numerator/denominator miRNA ratios miR-491-5p/let-7e+miR-107/miR-9+miR-128a/miR-181a.

16. The method of claim 12, wherein the neurodegenerative disorder (ND) is frontotemporal dementia (FTD), and the method comprises measuring one or more additional numerator/denominator miRNA ratios selected from miR-9*/miR-181a, miR-9*/miR-874, miR-9*/miR-125b, miR-9*/let-7e, miR-9*/miR-155, miR-99b/miR-181a, miR-99b/let-7e, miR-128a/miR-181a, miR-9*/miR-31, miR-9*/miR-146a, miR-9*/miR-9, miR-323-3p/miR-134, miR-338-3p/miR-181a, miR-491-5p/let-7e, miR-128a/miR-874, miR-128a/let-7e, miR-7/miR-874, miR-7/miR-125b, miR-338-3p/let-7e, miR-335-5p/miR-181a, miR-335-5p/miR-9, miR-107/miR-9, and miR-335-5p/miR-146a.

17. The method of claim 16, wherein the subject is a male, and the method comprises measuring a combination of numerator/denominator miRNA ratios miR-335-5p/let-7e+miR-99b/let-7e+miR-9*/miR-181a.

18. The method of claim 16, wherein the subject is a female, and the method comprises measuring a combination of numerator/denominator miRNA ratios miR-491-5p/let-7e+miR-107/miR-9+miR-128a/miR-181a.

19. The method of claim 11, wherein the neurodegenerative disorder (ND) is amyotrophic lateral sclerosis (ALS), and the method comprises measuring one or more additional numerator/denominator miRNA ratios selected from miR-206/miR-31, miR-206/miR-129-3p, miR-206/miR-138, miR-206/miR-874, miR-206/miR-125b, miR-206/miR-204, miR-206/miR-29a, miR-206/miR-155, miR-206/miR-338-3p, miR-206/miR-16, miR-206/miR-451, miR-206/miR-218, miR-99b/miR-9, miR-99b/miR-155, miR-99b/miR-338-3p, miR-9*/miR-129-3p, miR-99b/miR-155, miR-99b/let-7e, miR-181a/miR-338-3p, miR-335-5p/miR-338-3p, miR-7/miR-31, miR-7/miR-129-3p, miR-9*/miR-129-3p, miR-9*/miR-338-3p, miR-99b/miR-128a, miR-206/miR-7, miR-9*/miR-125b, miR-491-5p/miR-204, and miR-335-5p/let-7e.

20. The method of claim 19, wherein the subject is a male, and the method comprises measuring a combination of numerator/denominator miRNA ratios miR-206/miR-155+miR-9*/miR-129-3p+miR-335-5p/miR-338-3p.

21. The method of claim 19, wherein the subject is a female, and the method comprises measuring a combination of numerator/denominator miRNA ratios miR-206/miR-7+miR-9*/miR-125b+miR-491-5p/miR-204.

22. The method of claim 12, wherein the neurodegenerative disorder (ND) is amyotrophic lateral sclerosis (ALS), and the method comprises measuring one or more additional numerator/denominator miRNA ratios selected from miR-206/miR-31, miR-206/miR-129-3p, miR-206/miR-138, miR-206/miR-874, miR-206/miR-125b, miR-206/miR-204, miR-206/miR-29a, miR-206/miR-155, miR-206/miR-338-3p, miR-206/miR-16, miR-206/miR-451, miR-206/miR-218, miR-99b/miR-9, miR-99b/miR-155, miR-9*/miR-129-3p, miR-99b/miR-155, miR-99b/let-7e, miR-181a/miR-338-3p, miR-335-5p/miR-338-3p, miR-7/miR-31, miR-7/miR-129-3p, miR-9*/miR-129-3p, miR-9*/miR-338-3p, miR-99b/miR-338-3p, miR-99b/miR-128a, miR-206/miR-7, miR-9*/miR-125b, miR-491-5p/miR-204, and miR-335-5p/let-7e.

23. The method of claim 22, wherein the subject is a male, and the method comprises measuring a combination of numerator/denominator miRNA ratios miR-206/miR-155+miR-9*/miR-129-3p+miR-335-5p/miR-338-3p.

24. The method of claim 22, wherein the subject is a female, and the method comprises measuring a combination of numerator/denominator miRNA ratios miR-206/miR-7+miR-9*/miR-125b+miR-491-5p/miR-204.

25. The method of claim 11, wherein the neurodegenerative disorder (ND) is frontotemporal dementia (FTD) and the therapeutic agent is selected from an anti-psychotic, an anti-depressant, *Gingko biloba*, vitamin B12, folic acid, and any combinations thereof.

26. The method of claim 11, wherein the neurodegenerative disorder (ND) is amyotrophic lateral sclerosis (ALS) and the therapeutic agent is selected from riluzole, omigapil, creatine, Vitamin E, and any combinations thereof.

27. The method of claim 4, wherein the method comprises measuring a combination of the numerator/denominator miRNA ratios selected from miR-9*/let-7e+miR-335-5p/let-7e, miR-9*/miR-155+miR-99b/let-7e, miR-7/miR-874+miR-128a/let-7e, miR-99b/let-7e+miR-335-5p/let-7e+miR-128a/miR-181a, miR-9*/let-7e+miR-128a/miR-874, miR-9*/let-7e+miR-7/miR-451+miR-335-5p/let-7e, miR-9*/let-7e+miR-335-5p/let-7e+miR-128a/miR-874, miR-9*/miR-9+miR-99b/let-7e+miR-335-5p/let-7e, and miR-335-5p/miR-181a+miR-335-5p/miR-146a+miR-335-5p/miR-9.

28. The method of claim 7, wherein the method comprises measuring a combination of the numerator/denominator miRNA ratios selected from miR-206/miR-31+miR-99b/miR-338-3p, miR-206/miR-138+miR-9*/miR-129-3p, miR-206/miR-31+miR-335-5p/miR-338-3p, miR-206/miR-16+miR-335-5p/miR-338-3p, miR-9*/miR-129-3p+miR-99b/miR-338-3p, miR-206/miR-204+miR-206/miR-218+miR-335-5p/miR-338-3p, miR-206/miR-204+miR-206/miR-218+miR-9*/miR-129-3p, miR-206/miR-338-3p+miR-99b/miR-129-3p+miR-335-5p/miR-338-3p, miR-206/miR-338-3p+miR-99b/miR-155+miR-335-5p/miR-338-3p, and miR-181a/miR-338-3p+miR-335-5p/miR-338-3p+miR-7/miR-31+miR-7/miR-129-3p.

29. The method of claim 1, further comprising determining one or more additional numerator/denominator miRNA ratios,
wherein the ND is frontotemporal dementia (FTD) and the first miRNA in said one or more additional numerator/denominator miRNA ratios is selected from miR-7, miR-128a, miR-323-3p, miR-335-5p, miR-338-3p, miR-9*, miR-99b, and miR-491-5p, and the second miRNA is selected from let-7e, miR-125b, miR-146a, miR-155, miR-181a, miR-31, miR-874, and miR-9, or
the ND is amyotrophic lateral sclerosis (ALS) and the first miRNA in said one or more additional numerator/denominator miRNA ratios is selected from miR-7, miR-181a, miR-206, miR-335-5p, miR-9*, and miR-99b, and the second miRNA is selected from let-7e, miR-125b, miR-128a, miR-138, miR-155, miR-16, miR-204, miR-218, miR-29a, miR-31, miR-338-3p, miR-874, miR-9, miR-129-3p, and miR-451.

30. The method of claim 11, further comprising determining one or more additional numerator/denominator miRNA ratios,
wherein the ND is frontotemporal dementia (FTD) and the first miRNA in said one or more additional numerator/denominator miRNA ratios is selected from miR-7, miR-128a, miR-323-3p, miR-335-5p, miR-338-3p, miR-9*, miR-99b, and miR-491-5p, and the second miRNA is selected from let-7e, miR-125b, miR-146a, miR-155, miR-181a, miR-31, miR-874, and miR-9, or
the ND is amyotrophic lateral sclerosis (ALS) and the first miRNA in said one or more additional numerator/denominator miRNA ratios is selected from miR-7, miR-181a, miR-206, miR-335-5p, miR-9*, and miR-99b, and the second miRNA is selected from let-7e, miR-125b, miR-128a, miR-138, miR-155, miR-16, miR-204, miR-218, miR-29a, miR-31, miR-338-3p, miR-874, miR-9, miR-129-3p, and miR-451.

31. The method of claim 12, further comprising determining one or more additional numerator/denominator miRNA ratios,
wherein the ND is frontotemporal dementia (FTD) and the first miRNA in said one or more additional numerator/denominator miRNA ratios is selected from miR-7, miR-128a, miR-323-3p, miR-335-5p, miR-338-3p, miR-9*, miR-99b, and miR-491-5p, and the second miRNA is selected from let-7e, miR-125b, miR-146a, miR-155, miR-181a, miR-31, miR-874, and miR-9, or
the ND is amyotrophic lateral sclerosis (ALS) and the first miRNA in said one or more additional numerator/denominator miRNA ratios is selected from miR-7, miR-181a, miR-206, miR-335-5p, miR-9*, and miR-99b, and the second miRNA is selected from let-7e, miR-125b, miR-128a, miR-138, miR-155, miR-16, miR-204, miR-218, miR-29a, miR-31, miR-338-3p, miR-874, miR-9, miR-129-3p, and miR-451.

* * * * *